(12) United States Patent
Han et al.

(10) Patent No.: US 12,139,518 B2
(45) Date of Patent: Nov. 12, 2024

(54) COMPOSITIONS AND METHODS FOR TREATING OR PREVENTING FIBROSIS

(71) Applicant: Nexel Co., Ltd., Seoul (KR)

(72) Inventors: Choongseong Han, Seoul (KR); Dong-Hun Woo, Seoul (KR); Xiong Jin, Seoul (KR); Jaehun Lee, Seoul (KR); Geun Ho An, Seoul (KR); Tack Jin Yoo, Seoul (KR); Jinwoo Chung, Seoul (KR)

(73) Assignee: Nexel Co., Ltd., Seoul (KR)

( * ) Notice: Subject to any disclaimer, the term of this patent is extended or adjusted under 35 U.S.C. 154(b) by 371 days.

(21) Appl. No.: 17/285,040

(22) PCT Filed: Oct. 24, 2019

(86) PCT No.: PCT/IB2019/001136
§ 371 (c)(1),
(2) Date: Apr. 13, 2021

(87) PCT Pub. No.: WO2020/084344
PCT Pub. Date: Apr. 30, 2020

(65) Prior Publication Data
US 2021/0388041 A1    Dec. 16, 2021

(30) Foreign Application Priority Data

Oct. 25, 2018 (KR) .................. 10-2018-0128033
Oct. 25, 2018 (KR) .................. 10-2018-0128204
Oct. 26, 2018 (KR) .................. 10-2018-0128625

(51) Int. Cl.
*C07K 14/47* (2006.01)
*A61K 38/00* (2006.01)
*A61P 1/16* (2006.01)
*A61P 9/00* (2006.01)
*A61P 11/00* (2006.01)
*A61P 25/28* (2006.01)
*C12N 15/81* (2006.01)

(52) U.S. Cl.
CPC .............. *C07K 14/47* (2013.01); *A61P 1/16* (2018.01); *A61P 9/00* (2018.01); *A61P 11/00* (2018.01); *A61P 25/28* (2018.01); *C12N 15/815* (2013.01); *A61K 38/00* (2013.01); *C07K 2319/21* (2013.01); *C07K 2319/43* (2013.01)

(58) Field of Classification Search
None
See application file for complete search history.

(56) References Cited

U.S. PATENT DOCUMENTS 11,028,139 B2 * 6/2021 Han .................. A61P 1/16
2006/0233806 A1 10/2006 Nagata
2012/0004133 A1 * 1/2012 Wang ............... G01N 33/6893
435/7.1
2018/0334486 A1 * 11/2018 Han .................. A61K 38/1709
2023/0265160 A1 8/2023 Irigaray et al.

FOREIGN PATENT DOCUMENTS

| CN | 105288592 A | 2/2016 |
|---|---|---|
| EP | 4326307 A1 | 2/2024 |
| KR | 10-2017-0013621 A | 2/2017 |
| KR | 10-2023-0066169 A | 5/2023 |
| WO | WO-95/15171 A1 | 6/1995 |
| WO | WO-00/30667 A2 | 6/2000 |
| WO | WO-2012/099576 A1 | 7/2012 |
| WO | WO-2015/009948 A1 | 1/2015 |
| WO | WO-2015/025956 A1 | 2/2015 |
| WO | WO-2016/182660 A1 | 11/2016 |
| WO | WO-2017/018698 A1 | 2/2017 |
| WO | WO-2018/212372 A1 | 11/2018 |
| WO | WO-2020/084344 A2 | 4/2020 |
| WO | WO-2020/085545 A1 | 4/2020 |
| WO | WO-2020/085547 A1 | 4/2020 |
| WO | WO-2020/085548 A1 | 4/2020 |
| WO | WO-2020/084344 A3 | 7/2020 |

OTHER PUBLICATIONS

Venegas V and Zhou Z "Two alternative mechanisms that regulate the presentation of apoptotic cell engulfment signal in Caenorhabditis elegans" Molecular Biology of the Cell 18:3180-3192. (Year: 2009).*
NCBI Reference Sequence NP_005919.2 (Year: 2023).*
GenBank AAC50549.1 (Year: 1996).*
Borisenko et al. "Milk fat globule epidermal growth factor 8 (MFG-E*) binds to oxidized phosphatidylserine: implications for macrophage clearance of apoptotic cells" Cell Death and Differentiation 11:943-945. (Year: 2004).*
Kajikawa et al. "MFG-E8 inhibits periodontitis in non-human primates and its gingival crevicular fluid levels can differentiate periodontal health from disease in humans" J Clin Periodontol. 44:472-483. (Year: 2017).*
Kim et al., "Human pluripotent stem-cell-derived alveolar organoids for modeling pulmonary fibrosis and drug testing," Cell Death Discovery, 7(48): 12 pages (2021).
An et al., "Milk Fat Globule-EGF Factor 8, Secreted by Mesenchymal Stem Cells, Protest against Fibrosis in Mice," Gastroenterology, 152(5):1174-1186 (2016).

(Continued)

*Primary Examiner* — Sudhakar Katakam
*Assistant Examiner* — Zachary J Miknis
(74) *Attorney, Agent, or Firm* — Foley Hoag LLP; David P. Halstead

(57) ABSTRACT

The present application relates to compositions and methods comprising polypeptides derived from MFG-E8 for treating and preventing fibrosis and other diseases.

21 Claims, 39 Drawing Sheets

Specification includes a Sequence Listing.

(56) References Cited

OTHER PUBLICATIONS

Atabai et al., "Mfge8 Diminishes the Severity of Tissue Fibrosis in Mice by Binding and Targeting Collagen for Uptake by Macrophages," The Journal of Clinical Investigation, 119(12):3713-3722 (2009).
D'Haese et al., "The Impact of MFG-E8 in Chronic Pancreatitis: Potential for Future Immunotherapy?" BMC Gastroenterology, 13(14):1-9 (2013).
Haggqvist et al., "Medlin: An integral fragment of aortic smooth muscle cell-produced lactadherin forms the most common human amyloid," Proc. Natl. Acad. Sci., 96:8669-8674 (1999).
Huang et al., "Milk fat globule-EGF factor 8 suppresses the aberrant immune response of systemic lupus erythematosus-derived neutrophils and associated tissue damage," Cell Death and Differentiation, 24:263-275 (2017).
International Search Report and Written Opinion for International Application No. PCT/IB2019/001136 dated Jun. 15, 2020.
International Search Report for International Application No. PCT/KR2017/005150 dated Aug. 3, 2018.
Venegas et al., "Two Alternative Mechanisms That Regulate the Presentation of Apoptotic Cell Engulfment Signal in Caenorhabditis elegans," Molecular Biology of the Cell, 18:3180-3192 (2007).
An et al., "Milk Fat Globule-EGF Factor 8, Secreted by Mesenchymal Stem Cells, Protects Against Liver Fibrosis in Mice", Gastroenterology, 152(5): 1174-1186 (2016).
Boddaert et al., "Evidence of a Role for Lactadherin in Alzheimer's Disease", The American Journal of Pathology, 170(3): 921-929 (2007).
Couto et al., "Cloning and sequence analysis of human breast epithelial antigen BA46 reveals an RGD cell adhesion sequence presented on an epidermal growth factor-like domain", DNA and Cell Biology, 15(4): 281-286 (1996).
Database UniProt Accesion No. Q08431 (RecName: Full=Lactadherin; AltName: Full=Breast epithelial antigen BA46; AltName: Full=HMFG; AltName: Full=MFGM; AltName: Full=Milk fat globule-EGF factor 8; Short=MFG-E8; AltName: Full=SED1;) (Oct. 10, 2018).
Database UniProt Accesion No. Q08431-3 "Protein isoforms Q08431-3," (Sep. 12, 2018).
Extended European Search Report for EP Application No. 19875681.9 dated Sep. 15, 2022.
Raymond et al., "SED1/MFG-E8: A Bi-Motif protein that orchestrates diverse cellular interactions", Journal of Cellular Biochemistry, 106(6): 957-966 (2009).
Albert et al., "alphavbeta5 integrin recruits the Crkll-Dock180-Rac1 complex for phagocytosis of apoptotic cells", Nature Cell Biology, vol. 3, Dec. 2000, pp. 899-905.
An et al. "Truncated Milk Fat Globule-EGF-like Factor 8 Ameliorates Liver Fibrosis via Inhibition of Integrin-TGFβ Receptor Interaction", Biomedicines 2021, 9, 1529, 15 pages.
Developing Novel Recombinant Protein Drug Based on Advanced iPSC Technologies, Bio International Convention presentation (2023).
Jin et al. "Anti-fibrotic recombinant protein (NP-011)." LGC life science forum poster (2019).
Lee et al. "NP-011 Biotherapeutic Candidate." Bio International Convention presentation (2019).
Motegi et al., "Pericyte-Derived MFG-E8 Regulates Pathologic Angiogenesis", Asterioscler Thromb Vasc Biol, Sep. 2011, pp. 2024-2034.
Nandrot et al., "Essential role for MFG-E8 as ligand for alphavbeta5 integrin in diurnal retinal phagosytosis", PNAS, Jul. 17, 2007, vol. 104, No. 29, pp. 12005-12010.
Nexel Investigational Brochure, NP-011, May 30, 2022.
NP-011 Introduction, Bio International Convention presentation (2022).
NP-011 Introduction, Bio International Convention presentation (2021).
Aziz et al., "Role of MFG-E8 in the Brain." MFG-E8 and Inflammation (2014): 173-187.
Barallobre-Barreiro et al., "Proteomics analysis of cardiac extracellular matrix remodeling in a porcine model of ischemia/reperfusion injury." Circulation 125 (2012): 789-802.
Castellanos et al., "Expression, purification, and characterization of recombinant human and murine milk fat globule-epidermal growth factor-factor 8." Protein expression and purification 124 (2016): 10-22.
Deng et al., "Restoration of circulating MFGE8 (milk fat globule-EGF factor 8) attenuates cardiac hypertrophy through inhibition of Akt pathway." Hypertension 70 (2017): 770-779.
Genbank, AAP36434.1, *Homo sapiens* milk fat globule-EGF factor 8 protein, partial [synthetic construct], (Jul. 25, 2016.).
Kurz, "Development of tools for detection of phosphatidylserine exposure in vitro and in vivo." PhD Dissertation. Imu, 2020.
Li et al., "The neuroprotective effects of milk fat globule-EGF factor 8 against oligomeric amyloid beta toxicity." Journal of Neuroinflammation 9 (2012): 1-11.
NCBI, Reference Sequence: XP_016877695.1, lactadherin isoform X2 [*Homo sapiens*], (May 26, 2018.).
Neutzner et al., "MFG-E8/lactadherin promotes tumor growth in an angiogenesis-dependent transgenic mouse model of multistage carcinogenesis." Cancer Research 67:(14) (2007): 6777-6785.
Ooishi et al., "Extracellular vesicle-mediated MFG?E8 localization in the extracellular matrix is required for its integrin-dependent function in mouse mammary epithelial cells." Genes to Cells 22 (2017): 885-899.
Oshima et al., "Secretion of a peripheral membrane protein, MFG-E8, as a complex with membrane vesicles: A possible role in membrane secretion." European Journal of Biochemistry 269 (2002): 1209-1218.
Otzen et al., "Lactadherin binds to phosphatidylserine-containing vesicles in a two-step mechanism sensitive to vesicle size and composition." Biochimica et Biophysica Acta (BBA)—Biomembranes 1818 (2012): 1019-1027.
Strausberg et al., "MFGE8 protein [*Homo sapiens*]" GenBank Accession: AAH03610.1 (2003).
Uchiyama et al., "MFG-E8 regulates angiogenesis in cutaneous wound healing." The American Journal of Pathology 184(7) (2014): 1981-1990.
Wagner et al., "Medin co-aggregates with vascular amyloid-β in Alzheimer's disease." Nature 612 (2022): 123-131.
Ye et al., "NMR solution structure of C2 domain of MFG-E8 and insights into its molecular recognition with phosphatidylserine." Biochimica et Biophysica Acta (BBA)—Biomembranes 1828 (2013): 1083-1093.

\* cited by examiner

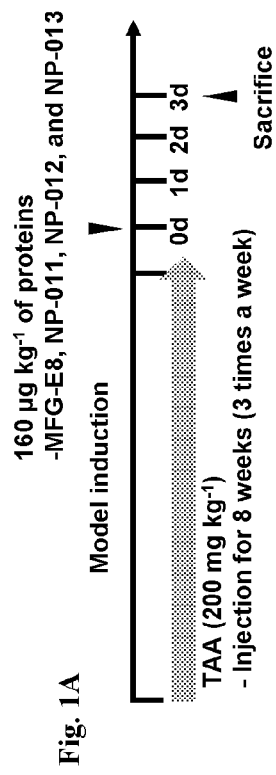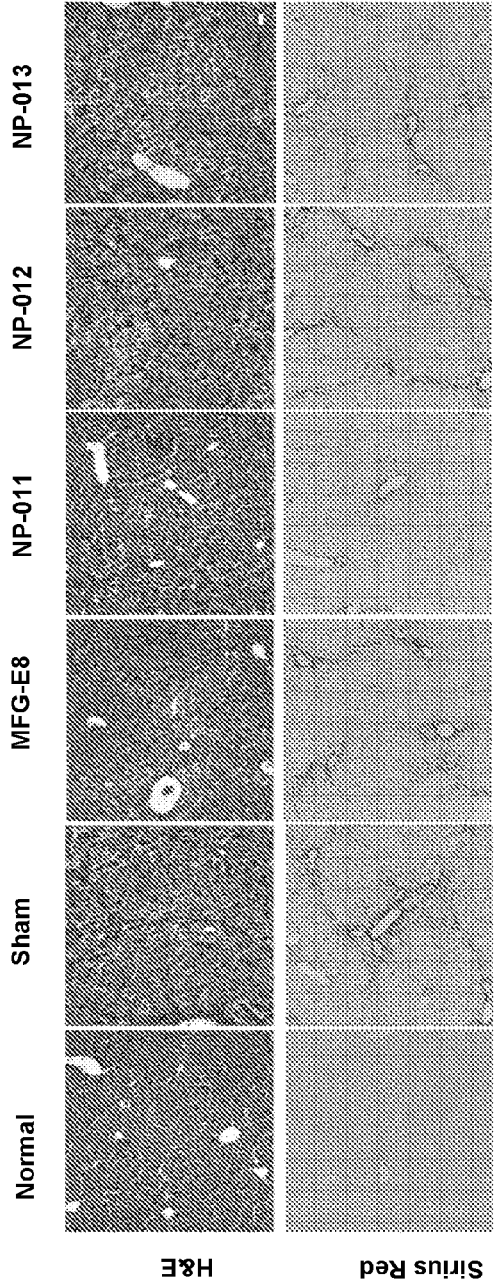
Fig. 1A
Fig. 1B

Fibrosis genes

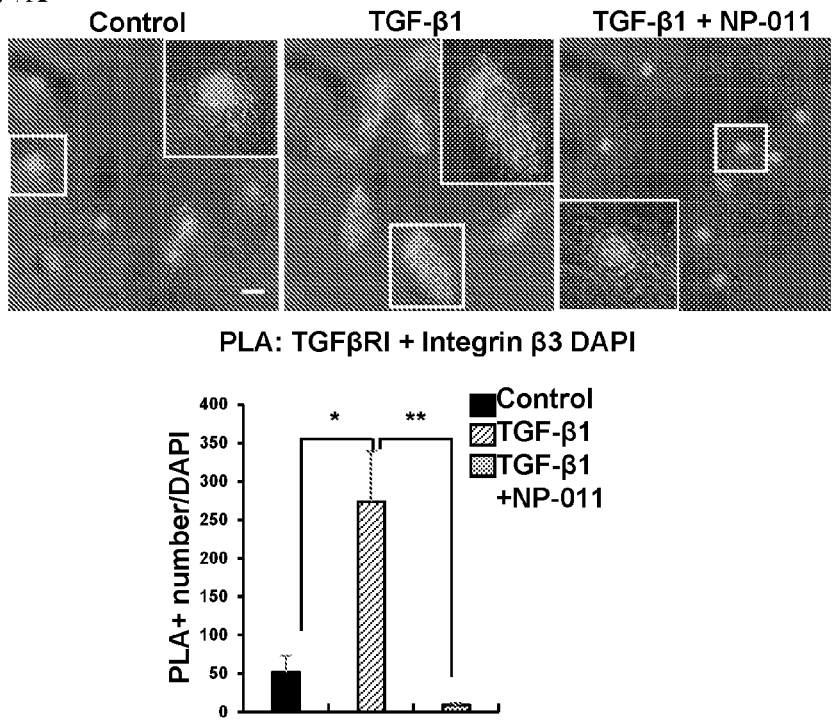
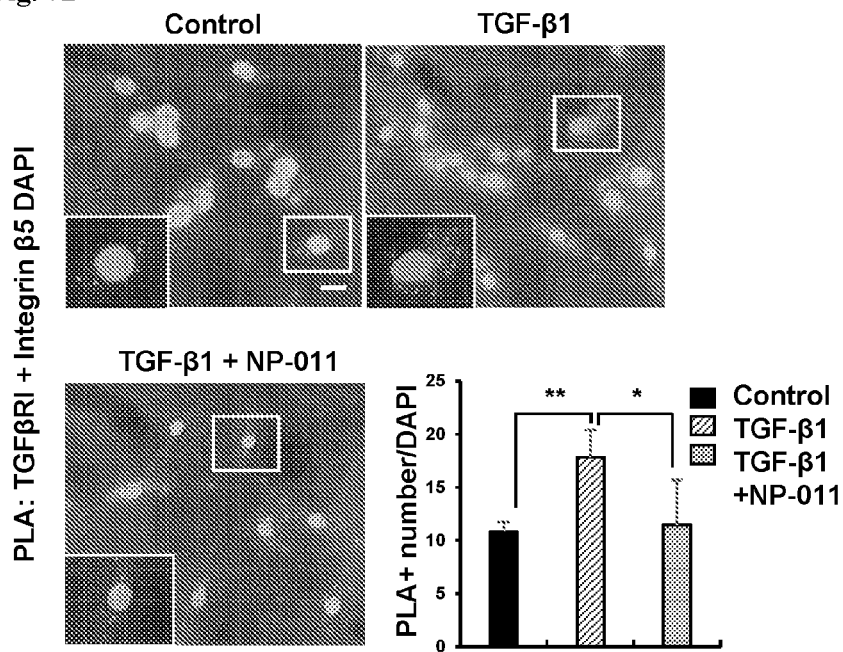

● Control: FITC-collagen + vehicle
● NP-011: FITC-collagen + NP-011

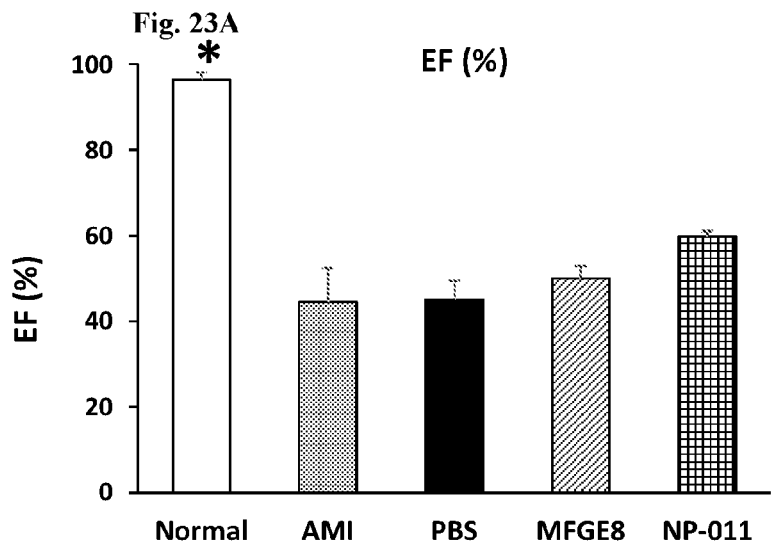
Fig. 23A
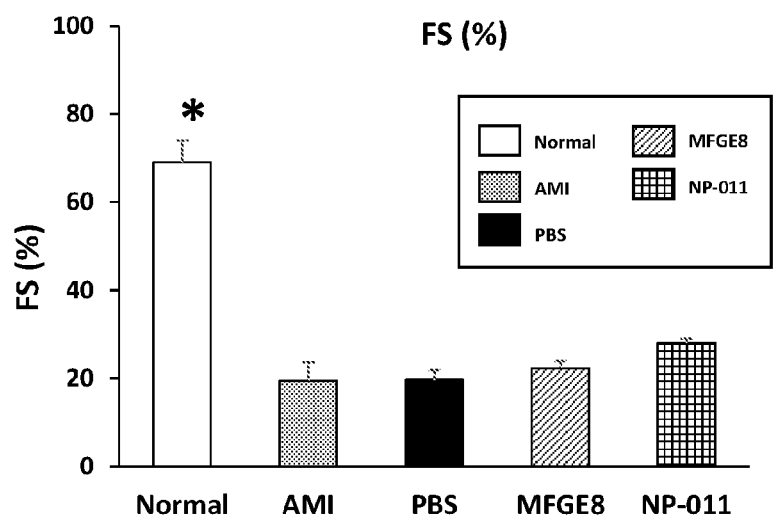
*P<0.05 Compared with MFGE8

*P<0.05 Compared with MFGE8

*P<0.05 Compared with MFGE8

Normal AMI PBS

MFGE8 NP-011

*$P<0.01$ compared with MFGE8

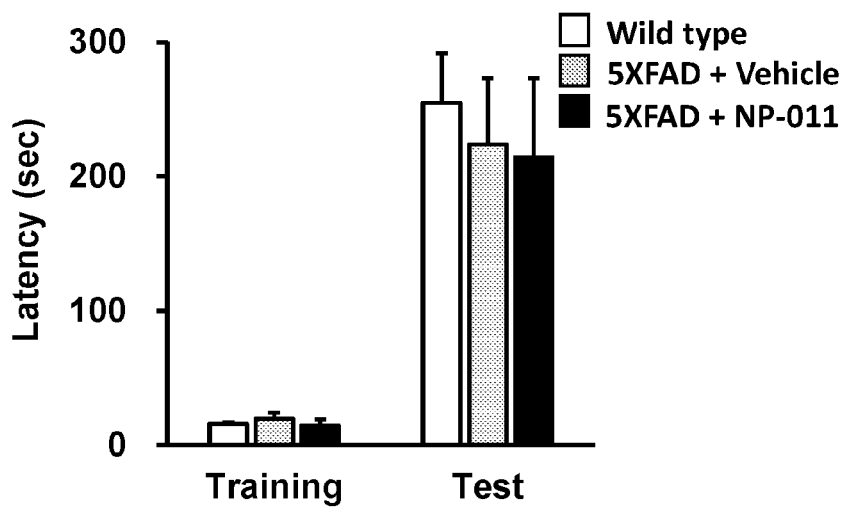
Fig. 27D Passive avoidance test
Memory recovery of mice right after NP-011 injection (3.5 month)
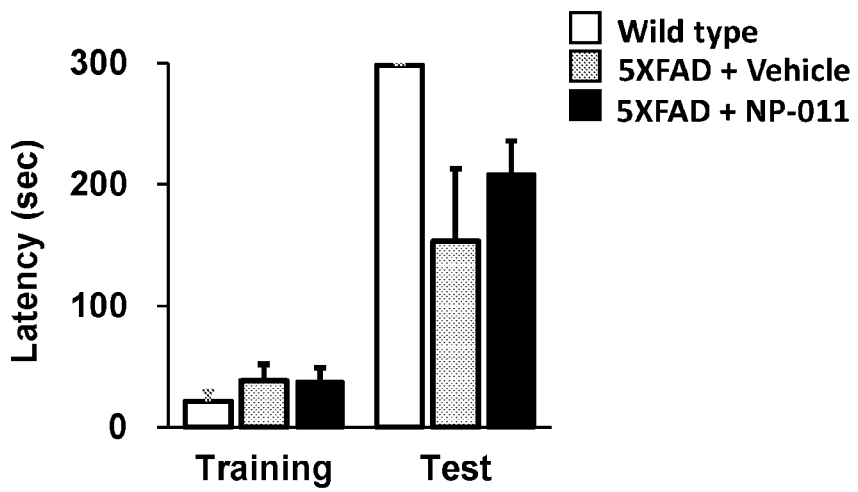
Fig. 27E Passive avoidance test
Memory recovery of mice 3 month after NP-011 injection (6.5 month)

Thioflavin S

SEQUENCE LISTING

<160> NUMBER OF SEQ ID NOS: 41

<210> SEQ ID NO 1
<211> LENGTH: 1780
<212> TYPE: DNA
<213> ORGANISM: Homo sapiens

<400> SEQUENCE: 1

| | | | | | | |
|---|---|---|---|---|---|---|
| agaacccgc | ggggtctgag | cagcccagcg | tgcccattcc | agcgcccgcg | tccccgcagc | 60 |
| atgccgcgcc | cccgcctgct | ggccgcgctg | tgcggcgcgc | tgctctgcgc | cccagcctc | 120 |
| ctcgtcgccc | tggatatctg | ttccaaaaac | ccctgccaca | acggtggttt | atgcgaggag | 180 |
| atttcccaag | aagtgcgagg | agatgtcttc | ccctcgtaca | cctgcacgtg | ccttaagggc | 240 |
| tacgcgggca | accactgtga | gacgaaatgt | gtcgagccac | tgggcctgga | gaatgggaac | 300 |
| attgccaact | cacagatcgc | cgcctcgtct | gtgcgtgtga | ccttcttggg | tttgcagcat | 360 |
| tgggtcccgg | agctggcccg | cctgaaccgc | gcaggcatgg | tcaatgcctg | gacacccagc | 420 |
| agcaatgacg | ataaccctg | gatccaggtg | aacctgctgc | ggaggatgtg | ggtaacaggt | 480 |
| gtggtgacgc | agggtgccag | ccgcttggcc | agtcatgagt | acctgaaggc | cttcaaggtg | 540 |
| gcctacagcc | ttaatggaca | cgaattcgat | ttcatccatg | atgttaataa | aaaacacaag | 600 |
| gagtttgtgg | gtaactggaa | caaaaacgcg | gtgcatgtca | acctgtttga | gacccctgtg | 660 |
| gaggctcagt | acgtgagatt | gtaccccacg | agctgccaca | cggcctgcac | tctgcgcttt | 720 |
| gagctactgg | gctgtgagct | gaacggatgc | gccaatcccc | tgggcctgaa | gaataacagc | 780 |
| atccctgaca | gcagatcac | ggcctccagc | agctacaaga | cctggggctt | gcatctcttc | 840 |
| agctggaacc | cctcctatgc | acggctggac | aagcagggca | acttcaacgc | ctgggttgcg | 900 |
| gggagctacg | gtaacgatca | gtggctgcag | atcttccctg | gcaactggga | caaccactcc | 960 |
| cacaagaaga | acttgtttga | gacgcccatc | ctggctcgct | atgtgcgcat | cctgcctgta | 1020 |
| gcctggcaca | accgcatcgc | cctgcgcctg | gagctgctgg | gctgttagtg | ccacctgcc | 1080 |
| acccccaggt | cttcctgctt | tccatgggcc | cgctgcctct | tggcttctca | gccccttta | 1140 |
| atcaccatag | ggctggggac | tggggaaggg | gagggtgttc | agaggcagca | ccaccacaca | 1200 |
| gtcacccctc | cctccctctt | tcccaccctc | cacctctcac | gggccctgcc | ccagccccta | 1260 |
| agccccgtcc | cctaaccccc | agtcctcact | gtcctgtttt | cttaggcact | gagggatctg | 1320 |
| agtaggtctg | ggatggacag | gaaagggcaa | agtagggcgt | gtggtttccc | tgcccctgtc | 1380 |
| cggaccgccg | atcccaggtg | cgtgtgtctc | tgtctctcct | agccctctc | tcacacatca | 1440 |
| cattcccatg | gtggcctcaa | gaaaggcccg | gaagcgccag | gctggagata | acagcctctt | 1500 |
| gcccgtcggc | cctgcgtcgg | ccctggggta | ccatgtggcc | acaactgctg | tggccccctg | 1560 |
| tccccaagac | acttcccctt | gtctccctgg | ttgcctctct | tgccccttgt | cctgaagccc | 1620 |
| agcgacacag | aaggggggtgg | ggcgggtcta | tggggagaaa | gggagcgagg | tcagaggagg | 1680 |
| gcatggggttg | gcagggtggg | cgtttggggc | cctctatgct | ggcttttcac | cccagaggac | 1740 |
| acaggcagct | tccaaaatat | atttatcttc | ttcacgggaa | | | 1780 |

<210> SEQ ID NO 2
<211> LENGTH: 335
<212> TYPE: PRT
<213> ORGANISM: Homo sapiens

<400> SEQUENCE: 2

Met Pro Arg Pro Arg Leu Leu Ala Ala Leu Cys Gly Ala Leu Leu Cys

```
              1               5                   10                  15
        Ala Pro Ser Leu Leu Val Ala Leu Asp Ile Cys Ser Lys Asn Pro Cys
                        20                  25                  30
        His Asn Gly Gly Leu Cys Glu Glu Ile Ser Gln Glu Val Arg Gly Asp
                        35                  40                  45
        Val Phe Pro Ser Tyr Thr Cys Thr Cys Leu Lys Gly Tyr Ala Gly Asn
                50                      55                  60
        His Cys Glu Thr Lys Cys Val Glu Pro Leu Gly Leu Glu Asn Gly Asn
        65                      70                  75                  80
        Ile Ala Asn Ser Gln Ile Ala Ala Ser Ser Val Arg Val Thr Phe Leu
                                85                  90                  95
        Gly Leu Gln His Trp Val Pro Glu Leu Ala Arg Leu Asn Arg Ala Gly
                        100                 105                 110
        Met Val Asn Ala Trp Thr Pro Ser Ser Asn Asp Asp Asn Pro Trp Ile
                        115                 120                 125
        Gln Val Asn Leu Leu Arg Arg Met Trp Val Thr Gly Val Val Thr Gln
                130                     135                 140
        Gly Ala Ser Arg Leu Ala Ser His Glu Tyr Leu Lys Ala Phe Lys Val
        145                     150                 155                 160
        Ala Tyr Ser Leu Asn Gly His Glu Phe Asp Phe Ile His Asp Val Asn
                                165                 170                 175
        Lys Lys His Lys Glu Phe Val Gly Asn Trp Asn Lys Asn Ala Val His
                        180                 185                 190
        Val Asn Leu Phe Glu Thr Pro Val Glu Ala Gln Tyr Val Arg Leu Tyr
                        195                 200                 205
        Pro Thr Ser Cys His Thr Ala Cys Thr Leu Arg Phe Glu Leu Leu Gly
                210                     215                 220
        Cys Glu Leu Asn Gly Cys Ala Asn Pro Leu Gly Leu Lys Asn Asn Ser
        225                     230                 235                 240
        Ile Pro Asp Lys Gln Ile Thr Ala Ser Ser Tyr Lys Thr Trp Gly
                                245                 250                 255
        Leu His Leu Phe Ser Trp Asn Pro Ser Tyr Ala Arg Leu Asp Lys Gln
                        260                 265                 270
        Gly Asn Phe Asn Ala Trp Val Ala Gly Ser Tyr Gly Asn Asp Gln Trp
                        275                 280                 285
        Leu Gln Ile Phe Pro Gly Asn Trp Asp Asn His Ser His Lys Lys Asn
                290                     295                 300
        Leu Phe Glu Thr Pro Ile Leu Ala Arg Tyr Val Arg Ile Leu Pro Val
        305                     310                 315                 320
        Ala Trp His Asn Arg Ile Ala Leu Arg Leu Glu Leu Leu Gly Cys
                                325                 330                 335

<210> SEQ ID NO 3
<211> LENGTH: 1804
<212> TYPE: DNA
<213> ORGANISM: Homo sapiens

<400> SEQUENCE: 3 agaacccgc ggggtctgag cagcccagcg tgcccattcc agcgcccgcg tccccgcagc    60
atgccgcgcc ccgcctgct ggccgcgctg tgcggcgcgc tgctctgcgc cccagcctc   120 ctcgtcgccc tggaatgtgt cgagccactg ggcctggaga tgggaacat tgccaactca   180 cagatcgccg cctcgtctgt gcgtgtgacc ttcttgggtt tgcagcattg ggtcccggag   240
ctggcccgcc tgaaccgcgc aggcatggtc aatgcctgga cacccagcag caatgacgat   300
```

```
aacccctgga tccaggtgaa cctgctgcgg aggatgtggg taacaggtgt ggtgacgcag    360
ggtgccagcc gcttggccag tcatgagtac ctgaaggcct tcaaggtggc ctacagcctt    420
aatggacacg aattcgattt catccatgat gttaataaaa aacacaagga gtttgtgggt    480
aactggaaca aaaacgcggt gcatgtcaac ctgtttgaga cccctgtgga ggctcagtac    540
gtgagattgt accccacgag ctgccacacg gcctgcactc tgcgctttga gctactgggc    600
tgtgagctga acgatgcgc caatccctg ggcctgaaga taacagcat ccctgacaag    660 cagatcacgg cctccagcag ctacaagacc tggggcttgc atctcttcag ctggaacccc    720
tcctatgcac ggctggacaa gcagggcaac ttcaacgcct gggttgcggg gagctacggt    780
aacgatcagt ggctgcaggt ggacctgggc tcctcgaagg aggtgacagg catcatcacc    840
cagggggccc gtaactttgg ctctgtccag tttgtggcat cctacaaggt tgcctacagt    900
aatgacagtg cgaactggac tgagtaccag gaccccagga ctggcagcag taagatcttc    960
cctggcaact gggacaacca ctcccacaag aagaacttgt ttgagacgcc catcctggct   1020
cgctatgtgc gcatcctgcc tgtagcctgg cacaaccgca tcgccctgcg cctggagctg   1080
ctgggctgtt agtggccacc tgccaccccc aggtcttcct gctttccatg ggcccgctgc   1140
ctcttggctt ctcagcccct ttaaatcacc atagggctgg ggactgggga aggggagggt   1200
gttcagaggc agcaccacca cacagtcacc cctccctccc tctttcccac cctccacctc   1260
tcacgggccc tgccccagcc cctaagcccc gtcccctaac ccccagtcct cactgtcctg   1320
ttttcttagg cactgaggga tctgagtagg tctgggatgg acaggaaagg gcaaagtagg   1380
gcgtgtggtt tccctgcccc tgtccggacc gccgatccca ggtgcgtgtg tctctgtctc   1440
tcctagcccc tctctcacac atcacattcc catggtggcc tcaagaaagg cccggaagcg   1500
ccaggctgga gataacagcc tcttgcccgt cggccctgcg tcggccctgg ggtaccatgt   1560
ggccacaact gctgtggccc cctgtcccca agacacttcc ccttgtctcc ctggttgcct   1620
ctcttgcccc ttgtcctgaa gcccagcgac acagaagggg gtgggcggg tctatgggga   1680 gaaagggagc gaggtcagag gagggcatgg gttggcaggg tgggcgtttg gggccctcta   1740
tgctggcttt tcaccccaga ggacacaggc agcttccaaa atatatttat cttcttcacg   1800
ggaa                                                                 1804
```

<210> SEQ ID NO 4
<211> LENGTH: 343
<212> TYPE: PRT
<213> ORGANISM: Homo sapiens

<400> SEQUENCE: 4

Met Pro Arg Pro Arg Leu Leu Ala Ala Leu Cys Gly Ala Leu Leu Cys
1               5                   10                  15

Ala Pro Ser Leu Leu Val Ala Leu Glu Cys Val Glu Pro Leu Gly Leu
            20                  25                  30

Glu Asn Gly Asn Ile Ala Asn Ser Gln Ile Ala Ala Ser Ser Val Arg
        35                  40                  45

Val Thr Phe Leu Gly Leu Gln His Trp Val Pro Glu Leu Ala Arg Leu
    50                  55                  60

Asn Arg Ala Gly Met Val Asn Ala Trp Thr Pro Ser Ser Asn Asp Asp
65                  70                  75                  80

Asn Pro Trp Ile Gln Val Asn Leu Leu Arg Arg Met Trp Val Thr Gly
                85                  90                  95

```
Val Val Thr Gln Gly Ala Ser Arg Leu Ala Ser His Glu Tyr Leu Lys
            100                 105                 110

Ala Phe Lys Val Ala Tyr Ser Leu Asn Gly His Glu Phe Asp Phe Ile
        115                 120                 125

His Asp Val Asn Lys Lys His Lys Glu Phe Val Gly Asn Trp Asn Lys
130                 135                 140

Asn Ala Val His Val Asn Leu Phe Glu Thr Pro Val Glu Ala Gln Tyr
145                 150                 155                 160

Val Arg Leu Tyr Pro Thr Ser Cys His Thr Ala Cys Thr Leu Arg Phe
                165                 170                 175

Glu Leu Leu Gly Cys Glu Leu Asn Gly Cys Ala Asn Pro Leu Gly Leu
            180                 185                 190

Lys Asn Asn Ser Ile Pro Asp Lys Gln Ile Thr Ala Ser Ser Ser Tyr
        195                 200                 205

Lys Thr Trp Gly Leu His Leu Phe Ser Trp Asn Pro Ser Tyr Ala Arg
210                 215                 220

Leu Asp Lys Gln Gly Asn Phe Asn Ala Trp Val Ala Gly Ser Tyr Gly
225                 230                 235                 240

Asn Asp Gln Trp Leu Gln Val Asp Leu Gly Ser Ser Lys Glu Val Thr
                245                 250                 255

Gly Ile Ile Thr Gln Gly Ala Arg Asn Phe Gly Ser Val Gln Phe Val
            260                 265                 270

Ala Ser Tyr Lys Val Ala Tyr Ser Asn Asp Ser Ala Asn Trp Thr Glu
        275                 280                 285

Tyr Gln Asp Pro Arg Thr Gly Ser Ser Lys Ile Phe Pro Gly Asn Trp
290                 295                 300

Asp Asn His Ser His Lys Lys Asn Leu Phe Glu Thr Pro Ile Leu Ala
305                 310                 315                 320

Arg Tyr Val Arg Ile Leu Pro Val Ala Trp His Asn Arg Ile Ala Leu
                325                 330                 335

Arg Leu Glu Leu Leu Gly Cys
            340

<210> SEQ ID NO 5
<211> LENGTH: 1989
<212> TYPE: DNA
<213> ORGANISM: Homo sapiens

<400> SEQUENCE: 5
agaaccccgc ggggtctgag cagcccagcg tgcccattcc agcgcccgcg tccccgcagc      60
atgccgcgcc ccgcctgctg gccgcgctg tgcggcgcgc tgctctgcgc ccccagcctc     120
ctcgtcgccc tggggtgatg tggccttttc cagaaggagg aaacaccata cctatcttac     180
acacagatat ctgttccaaa aaccccctgcc acaacggtgg tttatgcgag agatttccc     240 aagaagtgcg aggagatgtc ttcccctcgt cacctgcac gtgccttaag ggctacgcgg     300
gcaaccactg tgagacgaaa tgtgtcgagc cactgggcct ggagaatggg aacattgcca     360
actcacagat cgccgcctcg tctgtgcgtg tgaccttctt gggtttgcag cattgggtcc     420
cggagctggc ccgcctgaac cgcgcaggca tggtcaatgc ctggacaccc agcagcaatg     480
acgataaccc ctggatccag gtgaacctgc tgcggaggat gtgggtaaca ggtgtggtga     540
cgcagggtgc cagccgcttg gccagtcatg agtacctgaa ggccttcaag gtggcctaca     600
gccttaatgg acacgaattc gatttcatcc atgatgttaa taaaaaacac aaggagtttg     660
tgggtaactg gaacaaaaac gcggtgcatg tcaacctgtt tgagacccct gtggaggctc     720
```

```
agtacgtgag attgtacccc acgagctgcc acacggcctg cactctgcgc tttgagctac    780
tgggctgtga gctgaacgga tgcgccaatc ccctgggcct gaagaataac agcatccctg    840
acaagcagat cacggcctcc agcagctaca agacctgggg cttgcatctc ttcagctgga    900
acccctccta tgcacggctg gacaagcagg gcaacttcaa cgcctgggtt gcggggagct    960
acggtaacga tcagtggctg caggtggacc tgggctcctc gaaggaggtg acaggcatca   1020
tcacccaggg ggcccgtaac tttggctctg tccagtttgt ggcatcctac aaggttgcct   1080
acagtaatga cagtgcgaac tggactgagt accaggaccc caggactggc agcagtaaga   1140
tcttccctgg caactgggac aaccactccc acaagaagaa cttgtttgag cgcccatcc    1200
tggctcgcta tgtgcgcatc ctgcctgtag cctggcacaa ccgcatcgcc ctgcgcctgg   1260
agctgctggg ctgttagtgg ccacctgcca ccccaggtc ttcctgcttt ccatgggccc    1320
gctgcctctt ggcttctcag ccccttaaaa tcaccatagg gctggggact ggggaagggg    1380
agggtgttca gaggcagcac caccacacag tcacccctcc ctccctcttt cccaccctcc   1440
acctctcacg ggccctgccc cagcccctaa gccccgtccc ctaaccccca gtcctcactg   1500
tcctgttttc ttaggcactg agggatctga gtaggtctgg gatggacagg aaagggcaaa   1560
gtagggcgtg tggtttccct gccctgtcc ggaccgccga tcccaggtgc gtgtgtctct    1620
gtctctccta gcccctctct cacacatcac attcccatgg tggcctcaag aaaggcccgg   1680
aagcgccagg ctggagataa cagcctcttg cccgtcggcc ctgcgtcggc cctggggtac   1740
catgtggcca caactgctgt ggccccctgt ccccaagaca cttccccttg tctccctggt   1800
tgcctctctt gccccttgtc ctgaagccca gcgacacaga agggggtggg gcgggtctat   1860
ggggagaaag ggagcgaggt cagaggaggg catgggttgg cagggtgggc gtttggggcc   1920
ctctatgctg gcttttcacc ccagaggaca caggcagctt ccaaaatata tttatcttct   1980
tcacgggaa                                                          1989

<210> SEQ ID NO 6
<211> LENGTH: 379
<212> TYPE: PRT
<213> ORGANISM: Homo sapiens

<400> SEQUENCE: 6

Met Trp Pro Phe Pro Glu Gly Gly Asn Thr Ile Pro Ile Leu His Thr
1               5                   10                  15

Asp Ile Cys Ser Lys Asn Pro Cys His Asn Gly Gly Leu Cys Glu Glu
            20                  25                  30

Ile Ser Gln Glu Val Arg Gly Asp Val Phe Pro Ser Tyr Thr Cys Thr
        35                  40                  45

Cys Leu Lys Gly Tyr Ala Gly Asn His Cys Glu Thr Lys Cys Val Glu
    50                  55                  60

Pro Leu Gly Leu Glu Asn Gly Asn Ile Ala Asn Ser Gln Ile Ala Ala
65                  70                  75                  80

Ser Ser Val Arg Val Thr Phe Leu Gly Leu Gln His Trp Val Pro Glu
                85                  90                  95

Leu Ala Arg Leu Asn Arg Ala Gly Met Val Asn Ala Trp Thr Pro Ser
            100                 105                 110

Ser Asn Asp Asp Asn Pro Trp Ile Gln Val Asn Leu Leu Arg Arg Met
        115                 120                 125

Trp Val Thr Gly Val Val Thr Gln Gly Ala Ser Arg Leu Ala Ser His
    130                 135                 140
```

```
Glu Tyr Leu Lys Ala Phe Lys Val Ala Tyr Ser Leu Asn Gly His Glu
145                 150                 155                 160

Phe Asp Phe Ile His Asp Val Asn Lys Lys His Lys Glu Phe Val Gly
                165                 170                 175

Asn Trp Asn Lys Asn Ala Val His Val Asn Leu Phe Thr Pro Val
            180                 185                 190

Glu Ala Gln Tyr Val Arg Leu Tyr Pro Thr Ser Cys His Thr Ala Cys
            195                 200                 205

Thr Leu Arg Phe Glu Leu Leu Gly Cys Glu Leu Asn Gly Cys Ala Asn
210                 215                 220

Pro Leu Gly Leu Lys Asn Asn Ser Ile Pro Asp Lys Gln Ile Thr Ala
225                 230                 235                 240

Ser Ser Ser Tyr Lys Thr Trp Gly Leu His Leu Phe Ser Trp Asn Pro
                245                 250                 255

Ser Tyr Ala Arg Leu Asp Lys Gln Gly Asn Phe Asn Ala Trp Val Ala
            260                 265                 270

Gly Ser Tyr Gly Asn Asp Gln Trp Leu Gln Val Asp Leu Gly Ser Ser
            275                 280                 285

Lys Glu Val Thr Gly Ile Ile Thr Gln Gly Ala Arg Asn Phe Gly Ser
290                 295                 300

Val Gln Phe Val Ala Ser Tyr Lys Val Ala Tyr Ser Asn Asp Ser Ala
305                 310                 315                 320

Asn Trp Thr Glu Tyr Gln Asp Pro Arg Thr Gly Ser Ser Lys Ile Phe
                325                 330                 335

Pro Gly Asn Trp Asp Asn His Ser His Lys Lys Asn Leu Phe Glu Thr
            340                 345                 350

Pro Ile Leu Ala Arg Tyr Val Arg Ile Leu Pro Val Ala Trp His Asn
            355                 360                 365

Arg Ile Ala Leu Arg Leu Glu Leu Leu Gly Cys
370                 375

<210> SEQ ID NO 7
<211> LENGTH: 2544
<212> TYPE: DNA
<213> ORGANISM: Homo sapiens

<400> SEQUENCE: 7
acctccactg ttgacaaact tagacaaagc cccggggacc gggctgggca gagggggcggc    60 ttcttccgct gcgccctggc gggacagggg gatgcggccc tgctgtctct gcgctggggc   120
ttttgggctg ggactcggga catcgggtga cagccctgcc gccccaggg atgcggctta    180 cagataatga caaaggaatc cgctgtgtcg ggcctctctt ttccctggtg aaaaatgagg   240
ccagggaact gcgtttgact ttcgaacccc ttccacctgg gagattctag gactctagta   300
tggataagtc ttgtctggat aactttgtcc tggccatctc cctgccaact ccagttggct   360
ggacagttca ttggatttttt gcgctcccaa ttgtccgtgc ctggtcacat aagggaaggg   420
ccggggagtc ggtgcaatgg acgcaggccg taagtgggc ccgggagggg acccagaggc    480
ttcgaggagc ttgaagagg gctgcctgct gatgggagtc tcctgactcc ctccctcccg    540
cggccttggc cggctgctgt atcttccccg gtcctcctcc gcctcccagg aggcctccgg   600
aggccagctg ggcccttgc aggctggact tgcggatgcc ccgtgccatt caccgtggag    660
cgctgggagg gagtcagggc caggactctt taggtggccc ctccatcatt ttctcataga   720
aatgggattg actgaagcaa gatatctgtt ccaaaaaccc ctgccacaac ggtggtttat   780
```

```
gcgaggagat tcccaagaa gtgcgaggag atgtcttccc ctcgtacacc tgcacgtgcc      840
ttaagggcta cgcgggcaac cactgtgaga cgaaatgtgt cgagccactg ggcctggaga      900
atgggaacat tgccaactca cagatcgccg cctcgtctgt gcgtgtgacc ttcttgggtt      960
tgcagcattg ggtcccggag ctggcccgcc tgaaccgcgc aggcatggtc aatgcctgga     1020
cacccagcag caatgacgat aaccccctgga tccaggtgaa cctgctgcgg aggatgtggg    1080
taacaggtgt ggtgacgcag ggtgccagcc gcttggccag tcatgagtac ctgaaggcct     1140
tcaaggtggc ctacagcctt aatggacacg aattcgattt catccatgat gttaataaaa     1200
aacacaagga gtttgtgggt aactggaaca aaaacgcggt gcatgtcaac ctgtttgaga     1260
ccccctgtgga ggctcagtac gtgagattgt accccacgag ctgccacacg gcctgcactc    1320
tgcgctttga gctactgggc tgtgagctga acggatgcgc caatcccctg ggcctgaaga     1380
ataacagcat ccctgacaag cagatcacgg cctccagcag ctacaagacc tggggcttgc     1440
atctcttcag ctggaacccc tcctatgcac ggctggacaa gcagggcaac ttcaacgcct     1500
gggttgcggg gagctacggt aacgatcagt ggctgcaggt ggacctgggc tcctcgaagg     1560
aggtgacagg catcatcacc cagggggccc gtaactttgg ctctgtccag tttgtggcat     1620
cctacaaggt tgcctacagt aatgacagtg cgaactggac tgagtaccag gaccccagga     1680
ctggcagcag taagatcttc cctggcaact gggacaacca ctcccacaag aagaacttgt     1740
ttgagacgcc catcctggct cgctatgtgc gcatcctgcc tgtagcctgg cacaaccgca     1800
tcgccctgcg cctggagctg ctgggctgtt agtggccacc tgccacccc aggtcttcct      1860
gctttccatg ggcccgctgc ctcttggctt ctcagcccct ttaaatcacc atagggctgg    1920
ggactgggga aggggagggt gttcagagc agcaccacca cacagtcacc ctccctccc      1980
tctttcccac cctccacctc tcacgggccc tgccccagcc cctaagcccc gtcccctaac    2040
ccccagtcct cactgtcctg ttttcttagg cactgaggga tctgagtagg tctgggatgg    2100
acaggaaagg gcaaagtagg gcgtgtggtt tccctgcccc tgtccggacc gccgatccca    2160
ggtgcgtgtg tctctgtctc tcctagcccc tctctcacac atcacattcc catggtggcc   2220
tcaagaaagg cccggaagcg ccaggctgga gataacagcc tcttgcccgt cggccctgcg    2280
tcggccctgg ggtaccatgt ggccacaact gctgtggccc cctgtcccca agacacttcc    2340
ccttgtctcc ctggttgcct ctcttgcccc ttgtcctgaa gcccagcgac acagaagggg    2400
gtggggcggg tctatgggga gaagggagc gaggtcagag gagggcatgg gttggcaggg     2460
tgggcgtttg ggccctcta tgctggcttt tcacccagga ggacacaggc agcttccaaa     2520
atatatttat cttcttcacg ggaa                                           2544
```

<210> SEQ ID NO 8
<211> LENGTH: 275
<212> TYPE: PRT
<213> ORGANISM: Homo sapiens

<400> SEQUENCE: 8

```
Met Val Asn Ala Trp Thr Pro Ser Ser Asn Asp Asp Asn Pro Trp Ile
1               5                   10                  15

Gln Val Asn Leu Leu Arg Arg Met Trp Val Thr Gly Val Val Thr Gln
            20                  25                  30

Gly Ala Ser Arg Leu Ala Ser His Glu Tyr Leu Lys Ala Phe Lys Val
        35                  40                  45

Ala Tyr Ser Leu Asn Gly His Glu Phe Asp Phe Ile His Asp Val Asn
```

```
                50                  55                  60
Lys Lys His Lys Glu Phe Val Gly Asn Trp Asn Lys Asn Ala Val His
 65                  70                  75                  80

Val Asn Leu Phe Glu Thr Pro Val Glu Ala Gln Tyr Val Arg Leu Tyr
                 85                  90                  95

Pro Thr Ser Cys His Thr Ala Cys Thr Leu Arg Phe Glu Leu Leu Gly
                100                 105                 110

Cys Glu Leu Asn Gly Cys Ala Asn Pro Leu Gly Leu Lys Asn Asn Ser
                115                 120                 125

Ile Pro Asp Lys Gln Ile Thr Ala Ser Ser Tyr Lys Thr Trp Gly
                130                 135                 140

Leu His Leu Phe Ser Trp Asn Pro Ser Tyr Ala Arg Leu Asp Lys Gln
145                 150                 155                 160

Gly Asn Phe Asn Ala Trp Val Ala Gly Ser Tyr Gly Asn Asp Gln Trp
                165                 170                 175

Leu Gln Val Asp Leu Gly Ser Ser Lys Glu Val Thr Gly Ile Ile Thr
                180                 185                 190

Gln Gly Ala Arg Asn Phe Gly Ser Val Gln Phe Val Ala Ser Tyr Lys
                195                 200                 205

Val Ala Tyr Ser Asn Asp Ser Ala Asn Trp Thr Glu Tyr Gln Asp Pro
210                 215                 220

Arg Thr Gly Ser Ser Lys Ile Phe Pro Gly Asn Trp Asp Asn His Ser
225                 230                 235                 240

His Lys Lys Asn Leu Phe Glu Thr Pro Ile Leu Ala Arg Tyr Val Arg
                245                 250                 255

Ile Leu Pro Val Ala Trp His Asn Arg Ile Ala Leu Arg Leu Glu Leu
                260                 265                 270

Leu Gly Cys
        275

<210> SEQ ID NO 9
<211> LENGTH: 1936
<212> TYPE: DNA
<213> ORGANISM: Homo sapiens

<400> SEQUENCE: 9
agaaccccgc ggggtctgag cagcccagcg tgcccattcc agcgcccgcg tccccgcagc      60
atgccgcgcc cccgcctgct ggccgcgctg tgcggcgcgc tgctctgcgc ccccagcctc     120
ctcgtcgccc tggatatctg ttccaaaaac ccctgccaca cggtggtttt atgcgaggag     180
atttcccaag aagtgcgagg agatgtcttc ccctcgtaca cctgcacgtg ccttaagggc     240
tacgcgggca accactgtga gacgaaatgt gtcgagccac tgggcctgga gaatgggaac     300
attgccaact cacagatcgc cgcctcgtct gtgcgtgtga ccttcttggg tttgcagcat     360
tgggtcccgg agctggcccg cctgaaccgc gcaggcatgg tcaatgcctg gacacccagc     420
agcaatgacg ataaccctg gatccaggtg aacctgctgc ggaggatgtg ggtaacaggt     480
gtggtgacgc agggtgccag ccgcttggcc agtcatgagt acctgaaggc cttcaaggtg     540
gcctacagcc ttaatggaca cgaattcgat ttcatccatg atgttaataa aaaacacaag     600
gagtttgtgg gtaactggaa caaaaacgcg gtgcatgtca acctgtttga daccctgtg     660 gaggctcagt acgtgagatt gtaccccacg agctgccaca cggcctgcac tctgcgcttt     720
gagctactgg gctgtgagct gaacggatgc gccaatcccc tgggcctgaa gaataacagc     780 atcccctgaca agcagatcac ggcctccagc agctacaaga cctggggctt gcatctcttc     840
```

-continued

```
agctggaacc cctcctatgc acggctggac aagcagggca acttcaacgc ctgggttgcg      900
gggagctacg gtaacgatca gtggctgcag gtggacctgg gctcctcgaa ggaggtgaca      960
ggcatcatca cccagggggc ccgtaacttt ggctctgtcc agtttgtggc atcctacaag     1020
gttgcctaca gtaatgacag tgcgaactgg actgagtacc aggaccccag gactggcagc     1080
agtaagatct ccctggcaa ctgggacaac cactcccaca gaagaactt gtttgagacg      1140
cccatcctgg ctcgctatgt gcgcatcctg cctgtagcct ggcacaaccg catcgccctg     1200
cgcctggagc tgctgggctg ttagtggcca cctgccaccc ccaggtcttc ctgctttcca     1260
tgggcccgct gcctcttggc ttctcagccc ctttaaatca ccatagggct ggggactggg     1320
gaagggagg gtgttcagag gcagcaccac cacacagtca ccctccctc cctctttccc      1380
accctccacc tctcacgggc cctgcccag ccctaagcc ccgtcccta accccagtc      1440
ctcactgtcc tgttttctta ggcactgagg atctgagta ggtctgggat ggacaggaaa     1500
gggcaaagta gggcgtgtgg tttccctgcc cctgtccgga ccgccgatcc caggtgcgtg     1560
tgtctctgtc tctcctagcc cctctctcac acatcacatt cccatggtgg cctcaagaaa     1620
ggcccggaag cgccaggctg gagataacag cctcttgccc gtcggccctg cgtcggccct     1680
ggggtaccat gtggccacaa ctgctgtggc ccctgtccc caagacactt ccccttgtct      1740
ccctggttgc ctctcttgcc ccttgtcctg aagcccagcg acacagaagg gggtggggcg     1800
ggtctatggg gagaaaggga gcgaggtcag aggagggcat gggttggcag ggtgggcgtt     1860
tggggccctc tatgctggct tttcacccca gaggacacag gcagcttcca aaatatattt     1920
atcttcttca cgggaa                                                     1936
```

<210> SEQ ID NO 10
<211> LENGTH: 387
<212> TYPE: PRT
<213> ORGANISM: Homo sapiens

<400> SEQUENCE: 10

```
Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175
```

```
Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
            195                 200                 205

Pro Thr Ser Cys His Thr Ala Cys Thr Leu Arg Phe Glu Leu Leu Gly
            210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
            275                 280                 285

Leu Gln Val Asp Leu Gly Ser Ser Lys Glu Val Thr Gly Ile Ile Thr
            290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
            355                 360                 365

Ile Leu Pro Val Ala Trp His Asn Arg Ile Ala Leu Arg Leu Glu Leu
            370                 375                 380

Leu Gly Cys
385

<210> SEQ ID NO 11
<211> LENGTH: 1936
<212> TYPE: DNA
<213> ORGANISM: Homo sapiens

<400> SEQUENCE: 11
agaaccccgc ggggtctgag cagcccagcg tgcccattcc agcgcccgcg tccccgcagc      60
atgccgcgcc cccgcctgct ggccgcgctg tgcggcgcgc tgctctgcgc ccccagcctc     120
ctcgtcgccc tggatatctg ttccaaaaac ccctgccaca acggtggttt atgcgaggag     180
atttcccaag aagtgcgagg agatgtcttc ccctcgtaca cctgcacgtg ccttaagggc     240
tacgcgggca accactgtga cgaaatgtgt cgagccactg ggcatggaga atgggaac      300 attgccaact cacagatcgc cgcctcgtct gtgcgtgtga ccttcttggg tttgcagcat     360
tgggtcccgg agctggcccg cctgaaccgc gcaggcatgg tcaatgcctg acacccagc     420 agcaatgacg ataaccctg gatccaggtg aacctgctgc ggaggatgtg ggtaacaggt     480
gtggtgacgc agggtgccag ccgcttggcc agtcatgagt acctgaaggc cttcaaggtg     540
gcctacagcc ttaatggaca cgaattcgat tcatccatg atgttaataa aaaacacaag     600
gagtttgtgg gtaactggaa caaaaacgcg gtgcatgtca acctgtttga ccccctgtg     660 gaggctcagt acgtgagatt gtaccccacg agctgccaca cggcctgcac tctgcgcttt     720
gagctactgg gctgtgagct gaacggatgc gccaatcccc tgggcctgaa gaataacagc     780
atccctgaca gcagatcac ggcctccagc agctacaaga cctggggctt gcatctcttc     840
```

```
agctggaacc cctcctatgc acggctggac aagcagggca acttcaacgc ctgggttgcg      900
gggagctacg gtaacgatca gtggctgcag gtggacctgg gctcctcgaa ggaggtgaca      960
ggcatcatca cccagggggc ccgtaacttt ggctctgtcc agtttgtggc atcctacaag     1020
gttgcctaca gtaatgacag tgcgaactgg actgagtacc aggacccag gactggcagc     1080
agtaagatct tccctggcaa ctgggacaac cactcccaca agaagaactt gtttgagacg     1140
cccatcctgg ctcgctatgt gcgcatcctg cctgtagcct ggcacaaccg catcgccctg     1200
cgcctggagc tgctgggctg ttagtggcca cctgccaccc ccaggtcttc ctgctttcca     1260
tgggcccgct gcctcttggc ttctcagccc ctttaaatca ccatagggct ggggactggg     1320
gaagggagg gtgttcagag gcagcaccac cacacagtca cccctccctc cctctttccc     1380
accctccacc tctcacgggc cctgcccag cccctaagcc ccgtcccta acccccagtc     1440
ctcactgtcc tgttttctta ggcactgagg gatctgagta ggtctgggat ggacaggaaa     1500
gggcaaagta gggcgtgtgg tttccctgcc cctgtccgga ccgccgatcc caggtgcgtg     1560
tgtctctgtc tctcctagcc cctctctcac acatcacatt cccatggtgg cctcaagaaa     1620
ggcccggaag cgccaggctg gagataacag cctcttgccc gtcggccctg cgtcggccct     1680
ggggtaccat gtgccacaa ctgctgtggc ccctgtccc caagacactt ccccttgtct     1740
ccctggttgc ctctcttgcc ccttgtcctg aagcccagcg acacagaagg gggtggggcg     1800
ggtctatggg gagaaaggga gcgaggtcag aggagggcat gggttggcag ggtgggcgtt     1860
tggggccctc tatgctggct tttcacccca gaggacacag gcagcttcca aaatatattt     1920
atcttcttca cgggaa                                                    1936
```

<210> SEQ ID NO 12
<211> LENGTH: 387
<212> TYPE: PRT
<213> ORGANISM: Homo sapiens

<400> SEQUENCE: 12

```
Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Met Glu Asn Gly Asn
65                  70                  75                  80

Ile Ala Asn Ser Gln Ile Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175
```

| Lys | Lys | His | Lys<br>180 | Glu | Phe | Val | Gly | Asn<br>185 | Trp | Asn | Lys | Asn | Ala<br>190 | Val | His |

| Val | Asn | Leu<br>195 | Phe | Glu | Thr | Pro | Val<br>200 | Glu | Ala | Gln | Tyr | Val<br>205 | Arg | Leu | Tyr |

| Pro | Thr<br>210 | Ser | Cys | His | Thr | Ala<br>215 | Cys | Thr | Leu | Arg | Phe<br>220 | Glu | Leu | Leu | Gly |

| Cys<br>225 | Glu | Leu | Asn | Gly<br>230 | Cys | Ala | Asn | Pro | Leu<br>235 | Gly | Leu | Lys | Asn | Asn<br>240 | Ser |

| Ile | Pro | Asp | Lys | Gln<br>245 | Ile | Thr | Ala | Ser | Ser<br>250 | Tyr | Lys | Thr | Trp | Gly<br>255 |

| Leu | His | Leu | Phe<br>260 | Ser | Trp | Asn | Pro | Ser<br>265 | Tyr | Ala | Arg | Leu | Asp<br>270 | Lys | Gln |

| Gly | Asn | Phe<br>275 | Asn | Ala | Trp | Val | Ala<br>280 | Gly | Ser | Tyr | Gly | Asn<br>285 | Asp | Gln | Trp |

| Leu | Gln<br>290 | Val | Asp | Leu | Gly | Ser<br>295 | Ser | Lys | Glu | Val | Thr<br>300 | Gly | Ile | Ile | Thr |

| Gln<br>305 | Gly | Ala | Arg | Asn | Phe<br>310 | Gly | Ser | Val | Gln | Phe<br>315 | Val | Ala | Ser | Tyr | Lys<br>320 |

| Val | Ala | Tyr | Ser | Asn<br>325 | Asp | Ser | Ala | Asn | Trp<br>330 | Thr | Glu | Tyr | Gln | Asp<br>335 | Pro |

| Arg | Thr | Gly | Ser<br>340 | Ser | Lys | Ile | Phe | Pro<br>345 | Gly | Asn | Trp | Asp | Asn<br>350 | His | Ser |

| His | Lys | Lys<br>355 | Asn | Leu | Phe | Glu | Thr<br>360 | Pro | Ile | Leu | Ala | Arg<br>365 | Tyr | Val | Arg |

| Ile | Leu<br>370 | Pro | Val | Ala | Trp | His<br>375 | Asn | Arg | Ile | Ala | Leu<br>380 | Arg | Leu | Glu | Leu |

| Leu | Gly | Cys |
| 385 | | |

<210> SEQ ID NO 13
<211> LENGTH: 2188
<212> TYPE: DNA
<213> ORGANISM: Rattus norvegicus

<400> SEQUENCE: 13

```
attcccctgt gagaggagcg gacgcaggaa ctctccggtc ccagcatcgg agcttgtgga      60
ccatttcccg cgtcccgcag catgcagttc cccgtgtgc tggccgcgct gtgcggtgtg      120
ctgctctgcg cctccggcct cttcgctgcg tccggtgact tctgtgactc cagcctgtgc     180
ctgaatggtg ggacctgctt gatgggccaa gacaatgaca tctactgcct ctgccctgaa     240
ggcttcacag gccttgtgtg caacgagact gagaaggac cgtgttcccc aaacccttgc     300
ttccacgatg ccaaatgcct ggtgactgag gacacacagc gagggacat cttcactgag     360
tacatctgcc agtgccctgt gggctactcg ggcatccact gtgaactcga gaccacctcc     420
tacctggatg gagagtacct gtccagccca gccgtcccta ccacagccgt cccccaccac     480
gccatcccca ccacagccgt ccccaccaca gccgtcccca cagccgt ccccaccccg       540
gccccaaccc ccgatctttc aaccacctag gcctcccgct gttccacaaa gctgggcttg     600
gaaggggggcg ccattgccga ttcacagatt tctgcctcgt ctgtgtatat ggcttcatg     660
ggcttgcagc gctgggccc ggagctggct cgcctgtatc gcacagggat tgtcaatgca    720
tggacagcca gcagctatga tagcaagccc tggatccagg tggactttct gcggaagatg   780
cgggtatcag gtgtgatgac acaggtgcc agccgtgccg ggagggcgga taccctgaag   840
accttcaagg tggcttacag cctcgatgga cgcaggttcg agttcatcca ggatgaaagc  900
```

```
ggaaccggag acaaggagtt tatgggtaac caggacaaca acagcctgaa gattaacatg    960
ttcaacccca ctctggaggc acagtacata aggctgtacc ctgtctcgtg ccaccgcggc   1020
tgcaccctcc gcttcgagct cctgggctgc gagttgcatg gatgctctga gccctgggc    1080 ctgaagaata acacgattcc tgacagccaa ataacagcct ccagcagcta caagacgtgg   1140
aacctgcgtg cctttggctg gtaccccac ttggggcggc tggacaatca gggcaagatc    1200
aatgcctgga cagctcagag caacagtgcc aaggaatggc tgcaggttga cctgggcact   1260
cagaaaaaag tgacaggaat tatcacccag ggggcccgtg actttggcca catccagtat   1320
gtggcatcct ataaggtagc ccacagtgat gatggtgtgc agtggaccgt atatgaggaa   1380
caaggaacca gcaaggtctt ccagggcaac ttggacaaca actcccacaa gaagaacatc   1440
tttgagaaac ctttcatggc tcgctatgtg cgtgtccttc cactgtcctg cataaccgt    1500 atcaccctgc gcctggagct gctgggctgt tagtgcccag tccttccagc ccaagtgacg   1560
aggacggcca gaggctgagg ggcctcctgg ccctgcctcc caggcccgc tgccttctgt    1620 ggctgacacc ttctcaatcc tccctcttga ttgcactggg actacaggca ggaagggcaa   1680
gggggtttca gagttgcccc tcacccttcc cctcaccctg cagcccccac aggcctcctg   1740 ctagccccttt ctctcaggca ttctggggga gttggacagg tctgagatga atagagaaga  1800
agagtgaagt tggggtatgt gggctgctgt accaaccacc ccaagtccta aactttctcc   1860 agggggttgac tcaagactaa agggaacctc tggttgccca cccgtctctg cacaccgcac  1920
atccctccat gttccattcc tggaaggaga ggcccacgtc cgcttgctgc cccttgggtc   1980
accagatcct gcctcttatc tcctgagacc cctcttgacc ctcgctctgg agcctcggtt   2040
gacaagagga ctgtcgggtc tggagagata atgggctct gggtggttgg cgagctggct    2100
atgggacctc tgctggcttg ctacccaagc taacaagcag attccaaaat acatttgtgc   2160
tctccactgg aaaaaaaaaa aaaaaaaa                                      2188
```

<210> SEQ ID NO 14
<211> LENGTH: 483
<212> TYPE: PRT
<213> ORGANISM: Rattus norvegicus

<400> SEQUENCE: 14

```
Met Gln Phe Ser Arg Val Leu Ala Ala Leu Cys Gly Val Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Met Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Lys Gly Pro Cys Ser Pro Asn Pro Cys Phe His Asp Ala Lys Cys Leu
65                  70                  75                  80

Val Thr Glu Asp Thr Gln Arg Gly Asp Ile Phe Thr Glu Tyr Ile Cys
                85                  90                  95

Gln Cys Pro Val Gly Tyr Ser Gly Ile His Cys Glu Leu Glu Thr Thr
            100                 105                 110

Ser Tyr Leu Asp Gly Glu Tyr Leu Ser Ser Pro Ala Val Pro Thr Thr
        115                 120                 125

Ala Val Pro Thr Thr Ala Ile Pro Thr Thr Ala Val Pro Thr Thr Ala
    130                 135                 140
```

Val Pro Thr Thr Ala Val Pro Thr Pro Ala Pro Asn Pro Asp Leu Ser
145                 150                 155                 160

Asn His Leu Ala Ser Arg Cys Ser Thr Lys Leu Gly Leu Glu Gly Gly
                165                 170                 175

Ala Ile Ala Asp Ser Gln Ile Ser Ala Ser Ser Val Tyr Met Gly Phe
            180                 185                 190

Met Gly Leu Gln Arg Trp Gly Pro Glu Leu Ala Arg Leu Tyr Arg Thr
        195                 200                 205

Gly Ile Val Asn Ala Trp Thr Ala Ser Ser Tyr Asp Ser Lys Pro Trp
    210                 215                 220

Ile Gln Val Asp Phe Leu Arg Lys Met Arg Val Ser Gly Val Met Thr
225                 230                 235                 240

Gln Gly Ala Ser Arg Ala Gly Arg Ala Glu Tyr Leu Lys Thr Phe Lys
                245                 250                 255

Val Ala Tyr Ser Leu Asp Gly Arg Arg Phe Glu Phe Ile Gln Asp Glu
            260                 265                 270

Ser Gly Thr Gly Asp Lys Glu Phe Met Gly Asn Gln Asp Asn Asn Ser
        275                 280                 285

Leu Lys Ile Asn Met Phe Asn Pro Thr Leu Glu Ala Gln Tyr Ile Arg
    290                 295                 300

Leu Tyr Pro Val Ser Cys His Arg Gly Cys Thr Leu Arg Phe Glu Leu
305                 310                 315                 320

Leu Gly Cys Glu Leu His Gly Cys Ser Glu Pro Leu Gly Leu Lys Asn
                325                 330                 335

Asn Thr Ile Pro Asp Ser Gln Ile Thr Ala Ser Ser Ser Tyr Lys Thr
            340                 345                 350

Trp Asn Leu Arg Ala Phe Gly Trp Tyr Pro His Leu Gly Arg Leu Asp
        355                 360                 365

Asn Gln Gly Lys Ile Asn Ala Trp Thr Ala Gln Ser Asn Ser Ala Lys
    370                 375                 380

Glu Trp Leu Gln Val Asp Leu Gly Thr Gln Lys Lys Val Thr Gly Ile
385                 390                 395                 400

Ile Thr Gln Gly Ala Arg Asp Phe Gly His Ile Gln Tyr Val Ala Ser
                405                 410                 415

Tyr Lys Val Ala His Ser Asp Asp Gly Val Gln Trp Thr Val Tyr Glu
            420                 425                 430

Glu Gln Gly Thr Ser Lys Val Phe Gln Gly Asn Leu Asp Asn Asn Ser
        435                 440                 445

His Lys Lys Asn Ile Phe Glu Lys Pro Phe Met Ala Arg Tyr Val Arg
    450                 455                 460

Val Leu Pro Leu Ser Trp His Asn Arg Ile Thr Leu Arg Leu Glu Leu
465                 470                 475                 480

Leu Gly Cys

<210> SEQ ID NO 15
<211> LENGTH: 2020
<212> TYPE: DNA
<213> ORGANISM: Rattus norvegicus

<400> SEQUENCE: 15
attcccctgt gagaggagcg gacgcaggaa ctctccggtc ccagcatcgg agcttgtgga    60
ccatttcccg cgtcccgcag catgcagttc tcccgtgtgc tggccgcgct gtgcggtgtg   120
ctgctctgcg cctccggcct cttcgctgcg tccggtgact tctgtgactc cagcctgtgc   180

```
ctgaatggtg ggacctgctt gatgggccaa gacaatgaca tctactgcct ctgccctgaa    240
ggcttcacag gccttgtgtg caacgagact gagaaaggac cgtgttcccc aaacccttgc    300
ttccacgatg ccaaatgcct ggtgactgag gacacacagc gaggggacat cttcactgag    360
tacatctgcc agtgccctgt gggctactcg ggcatccact gtgaactcgg ctgttccaca    420
aagctgggct tggaagggg cgccattgcc gattcacaga tttctgcctc gtctgtgtat    480
atgggcttca tgggcttgca gcgctgggc ccggagctgg ctcgcctgta tcgcacaggg    540
attgtcaatg catggacagc cagcagctat gatagcaagc cctggatcca ggtggacttt    600
ctgcggaaga tgcgggtatc aggtgtgatg acacagggtg ccagccgtgc cgggagggcg    660
gaatacctga agaccttcaa ggtggcttac agcctcgatg gacgcaggtt cgagttcatc    720
caggatgaaa gcgaaccgg agacaaggag tttatgggta accaggacaa caacagcctg    780
aagattaaca tgttcaaccc cactctggag gcacagtaca taaggctgta ccctgtctcg    840
tgccaccgcg gctgcaccct ccgcttcgag ctcctgggct gcgagttgca tggatgctct    900
gagcccctgg gcctgaagaa taacacgatt cctgacagcc aaataacagc ctccagcagc    960
tacaagacgt ggaacctgcg tgcctttggc tggtaccccc acttggggcg gctggacaat   1020
cagggcaaga tcaatgcctg gacagctcag agcaacagtg ccaaggaatg gctgcaggtt   1080
gacctgggca ctcagaaaaa agtgacagga attatcaccc agggggcccg tgactttggc   1140
cacatccagt atgtggcatc ctataaggta gcccacagtg atgatggtgt gcagtggacc   1200
gtatatgagg aacaaggaac cagcaaggtc ttccagggca acttggacaa caactcccac   1260
aagaagaaca tctttgagaa acctttcatg gctcgctatg tgcgtgtcct tccactgtcc   1320
tggcataacc gtatcaccct gcgcctggag ctgctgggct gttagtgccc agtccttcca   1380
gcccaagtga cgaggacggc cagaggctga ggggcctcct ggccctgcct cccaggccct   1440
gctgccttct gtggctgaca ccttctcaat cctccctctt gattgcactg ggactacagg   1500
caggaagggc aaggggggttt cagagttgcc cctcacccctt ccctcaccc tgcagccccc   1560 acaggcctcc tgctagcccc ttctctcagg cattctgggg gagttggaca ggtctgagat   1620
gaatagagaa gaagagtgaa gttggggtat gtgggctgct gtaccaacca ccccaagtcc   1680
taaactttct ccagggtttg actcaagact aaagggaacc tctggttgcc cacccgtctc   1740
tgcacaccgc acatccctcc atgttccatt cctggaagga gaggcccacg tccgcttgct   1800
gccccttggg tcaccagatc ctgcctctta tctcctgaga cccctcttga ccctcgctct   1860
ggagcctcgt tgacaagag gactgtcggg tctggagaga tagatgggct ctgggtggtt   1920
ggcgagctgg ctatgggacc tctgctggct tgctacccaa gctaacaagc agattccaaa   1980
atacatttgt gctctccact ggaaaaaaaa aaaaaaaaa                          2020
```

<210> SEQ ID NO 16
<211> LENGTH: 427
<212> TYPE: PRT
<213> ORGANISM: Rattus norvegicus

<400> SEQUENCE: 16

Met Gln Phe Ser Arg Val Leu Ala Ala Leu Cys Gly Val Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Met Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Lys Gly Pro Cys Ser Pro Asn Pro Cys Phe His Asp Ala Lys Cys Leu
 65                  70                  75                  80

Val Thr Glu Asp Thr Gln Arg Gly Asp Ile Phe Thr Glu Tyr Ile Cys
                85                  90                  95

Gln Cys Pro Val Gly Tyr Ser Gly Ile His Cys Glu Leu Gly Cys Ser
            100                 105                 110

Thr Lys Leu Gly Leu Glu Gly Gly Ala Ile Ala Asp Ser Gln Ile Ser
            115                 120                 125

Ala Ser Ser Val Tyr Met Gly Phe Met Gly Leu Gln Arg Trp Gly Pro
        130                 135                 140

Glu Leu Ala Arg Leu Tyr Arg Thr Gly Ile Val Asn Ala Trp Thr Ala
145                 150                 155                 160

Ser Ser Tyr Asp Ser Lys Pro Trp Ile Gln Val Asp Phe Leu Arg Lys
                165                 170                 175

Met Arg Val Ser Gly Val Met Thr Gln Gly Ala Ser Arg Ala Gly Arg
            180                 185                 190

Ala Glu Tyr Leu Lys Thr Phe Lys Val Ala Tyr Ser Leu Asp Gly Arg
        195                 200                 205

Arg Phe Glu Phe Ile Gln Asp Glu Ser Gly Thr Gly Asp Lys Glu Phe
    210                 215                 220

Met Gly Asn Gln Asp Asn Asn Ser Leu Lys Ile Asn Met Phe Asn Pro
225                 230                 235                 240

Thr Leu Glu Ala Gln Tyr Ile Arg Leu Tyr Pro Val Ser Cys His Arg
                245                 250                 255

Gly Cys Thr Leu Arg Phe Glu Leu Leu Gly Cys Glu Leu His Gly Cys
            260                 265                 270

Ser Glu Pro Leu Gly Leu Lys Asn Asn Thr Ile Pro Asp Ser Gln Ile
        275                 280                 285

Thr Ala Ser Ser Ser Tyr Lys Thr Trp Asn Leu Arg Ala Phe Gly Trp
    290                 295                 300

Tyr Pro His Leu Gly Arg Leu Asp Asn Gln Gly Lys Ile Asn Ala Trp
305                 310                 315                 320

Thr Ala Gln Ser Asn Ser Ala Lys Glu Trp Leu Gln Val Asp Leu Gly
                325                 330                 335

Thr Gln Lys Lys Val Thr Gly Ile Ile Thr Gln Gly Ala Arg Asp Phe
            340                 345                 350

Gly His Ile Gln Tyr Val Ala Ser Tyr Lys Val Ala His Ser Asp Asp
        355                 360                 365

Gly Val Gln Trp Thr Val Tyr Glu Glu Gln Gly Thr Ser Lys Val Phe
    370                 375                 380

Gln Gly Asn Leu Asp Asn Asn Ser His Lys Lys Asn Ile Phe Glu Lys
385                 390                 395                 400

Pro Phe Met Ala Arg Tyr Val Arg Val Leu Pro Leu Ser Trp His Asn
                405                 410                 415

Arg Ile Thr Leu Arg Leu Glu Leu Leu Gly Cys
            420                 425

<210> SEQ ID NO 17
<211> LENGTH: 2032
<212> TYPE: DNA
<213> ORGANISM: Mus musculus

<400> SEQUENCE: 17

```
ggcgcctgat ttattccgga gtgagaggag cggacgcagg aactctcgag tcccagcatc      60
agagcgcgtg gaccttttcc cgcgtcccgc agcatgcagg tctcccgtgt gctggccgcg     120
ctgtgcggca tgctactctg cgcctctggc ctcttcgccg cgtctggtga cttctgtgac     180
tccagcctgt gcctgaacgg tggcacctgc ttgacgggcc aagacaatga catctactgc     240
ctctgccctg aaggcttcac aggccttgtg tgcaatgaga ctgagagagg accatgctcc     300
ccaaacccct gctacaatga tgccaaatgt ctggtgactt ggacacaca gcgtggggac     360
atcttcaccg aatacatctg ccagtgccct gtgggctact cggcatcca ctgtgaaacc     420
ggttgttcta cacagctggg catggaaggg gcgccattg ctgattcaca gatttccgcc     480
tcgtctgtgt atatgggttt catgggcttg cagcgctggg cccggagct ggctcgtctg     540
taccgcacag ggatcgtcaa tgcctggaca gccagcaact atgatagcaa gccctggatc     600
caggtgaacc ttctgcggaa gatgcgggta tcaggtgtga tgacgcaggg tgccagccgt     660
gccgggaggg cggagtacct gaagaccttc aaggtggctt acagcctcga cggacgcaag     720
tttgagttca tccaggatga aagcggtgga gacaaggagt ttttgggtaa cctggacaac     780
aacagcctga aggttaacat gttcaacccg actctggagg cacagtacat aaagctgtac     840
cctgtttcgt gccaccgcgg ctgcaccctc cgcttcgagc tcctgggctg tgagttgcac     900
ggatgttctg agcccctggg cctgaagaat aacacaattc ctgacagcca gatgtcagcc     960
tccagcagct acaagacatg gaacctgcgt gcttttggct ggtacccca cttgggaagg    1020
ctggataatc agggcaagat caatgcctgg acggctcaga gcaacagtgc caaggaatgg    1080
ctgcaggttg acctgggcac tcagaggcaa gtgacaggaa tcatcccca gggggcccgt    1140
gactttggcc acatccagta tgtggcgtcc tacaaggtag cccacagtga tgatggtgtg    1200
cagtggactg tatatgagga gcaaggaagc agcaaggtct tccagggcaa cttggacaac    1260
aactcccaca gaagaacat cttcgagaaa cccttcatgg ctcgctacgt gcgtgtcctt    1320
ccagtgtcct ggcataaccg catcacctg cgcctggagc tgctgggctg ttaatgctca    1380
gtcctgccag cccaaacgat gaggatggcc agaggctgag gggcctcctg gcccctgcctc    1440
ccaggccctg ctgccttctg tggctgacga ccttcttggc cttcccttct gattgtactg    1500
gggctggagg caggaagggc caggggattt cagagttgcc cttcacccctt tccctcaccc    1560
tgcagccccc acaggcctcc tgctagcccc cttctctcag gcattctggg ggagttggac    1620
aggtctgaga tgaatagaga agaagagtga agttggggta tgtgggctat ctgtaccaac    1680
cacccccaagt cctaaacttc ctgccagggc ttgactcagg actgaaggga gcccctgact    1740
gcccatccct ctctgcacac cacacattcc tccatgttcc attccgggaa ggagaggccc    1800
acgtccgctt gctgtcccttt gggtcaccag gtcctgcctc ttatctcctg agacgcctct    1860
tgacccttgc actggagcct cagttgacaa ggagactggc gggtctggag aggtcggtgg    1920
ctctgggtgg ttgacaggtt ggctgtggga cctctgctgg cttgctaccc aagttaacaa    1980
gcagattcca aaatacattc gtgttctcca ctggaaaaaa aaaaaaaaaa aa            2032
```

<210> SEQ ID NO 18
<211> LENGTH: 426
<212> TYPE: PRT
<213> ORGANISM: Mus musculus

<400> SEQUENCE: 18

Met Gln Val Ser Arg Val Leu Ala Ala Leu Cys Gly Met Leu Leu Cys

-continued

```
1               5                   10                  15
Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
                35                  40                  45

Cys Leu Cys Pro Glu Gly Phe Thr Gly Leu Val Cys Asn Glu Thr Glu
                50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Gly Cys Ser
                100                 105                 110

Thr Gln Leu Gly Met Glu Gly Gly Ala Ile Ala Asp Ser Gln Ile Ser
                115                 120                 125

Ala Ser Ser Val Tyr Met Gly Phe Met Gly Leu Gln Arg Trp Gly Pro
130                 135                 140

Glu Leu Ala Arg Leu Tyr Arg Thr Gly Ile Val Asn Ala Trp Thr Ala
145                 150                 155                 160

Ser Asn Tyr Asp Ser Lys Pro Trp Ile Gln Val Asn Leu Leu Arg Lys
                165                 170                 175

Met Arg Val Ser Gly Val Met Thr Gln Gly Ala Ser Arg Ala Gly Arg
                180                 185                 190

Ala Glu Tyr Leu Lys Thr Phe Lys Val Ala Tyr Ser Leu Asp Gly Arg
                195                 200                 205

Lys Phe Glu Phe Ile Gln Asp Glu Ser Gly Gly Asp Lys Glu Phe Leu
210                 215                 220

Gly Asn Leu Asp Asn Asn Ser Leu Lys Val Asn Met Phe Asn Pro Thr
225                 230                 235                 240

Leu Glu Ala Gln Tyr Ile Lys Leu Tyr Pro Val Ser Cys His Arg Gly
                245                 250                 255

Cys Thr Leu Arg Phe Glu Leu Leu Gly Cys Glu Leu His Gly Cys Ser
                260                 265                 270

Glu Pro Leu Gly Leu Lys Asn Asn Thr Ile Pro Asp Ser Gln Met Ser
                275                 280                 285

Ala Ser Ser Tyr Lys Thr Trp Asn Leu Arg Ala Phe Gly Trp Tyr
                290                 295                 300

Pro His Leu Gly Arg Leu Asp Asn Gln Gly Lys Ile Asn Ala Trp Thr
305                 310                 315                 320

Ala Gln Ser Asn Ser Ala Lys Glu Trp Leu Gln Val Asp Leu Gly Thr
                325                 330                 335

Gln Arg Gln Val Thr Gly Ile Ile Thr Gln Gly Ala Arg Asp Phe Gly
                340                 345                 350

His Ile Gln Tyr Val Ala Ser Tyr Lys Val Ala His Ser Asp Asp Gly
                355                 360                 365

Val Gln Trp Thr Val Tyr Glu Glu Gln Gly Ser Ser Lys Val Phe Gln
                370                 375                 380

Gly Asn Leu Asp Asn Asn Ser His Lys Lys Asn Ile Phe Glu Lys Pro
385                 390                 395                 400

Phe Met Ala Arg Tyr Val Arg Val Leu Pro Val Ser Trp His Asn Arg
                405                 410                 415

Ile Thr Leu Arg Leu Glu Leu Leu Gly Cys
                420                 425
```

<210> SEQ ID NO 19
<211> LENGTH: 2143
<212> TYPE: DNA
<213> ORGANISM: Mus musculus

<400> SEQUENCE: 19

| | | | | | |
|---|---|---|---|---|---|
| ggcgcctgat | ttattccgga | gtgagaggag | cggacgcagg | aactctcgag | tcccagcatc | 60 |
| agagcgcgtg | gacctttcc | cgcgtcccgc | agcatgcagg | tctcccgtgt | gctggccgcg | 120 |
| ctgtgcggca | tgctactctg | cgcctctggc | ctcttcgccg | cgtctggtga | cttctgtgac | 180 |
| tccagcctgt | gcctgaacgg | tggcacctgc | ttgacgggcc | aagacaatga | catctactgc | 240 |
| ctctgccctg | aaggcttcac | aggccttgtg | tgcaatgaga | ctgagagagg | accatgctcc | 300 |
| ccaaacccctt | gctacaatga | tgccaaatgt | ctggtgactt | tggacacaca | gcgtggggac | 360 |
| atcttcaccg | aatacatctg | ccagtgccct | gtgggctact | cgggcatcca | ctgtgaaacc | 420 |
| gagaccaact | actacaacct | ggatggagaa | tacatgttca | ccacagccgt | ccccaatact | 480 |
| gccgtcccca | ccccggcccc | cacccccgat | cttttccaaca | acctagcctc | ccgttgttct | 540 |
| acacagctgg | gcatggaagg | gggcgccatt | gctgattcac | agatttccgc | ctcgtctgtg | 600 |
| tatatgggtt | tcatgggctt | gcagcgctgg | ggcccggagc | tggctcgtct | gtaccgcaca | 660 |
| gggatcgtca | atgcctggac | agccagcaac | tatgatagca | agcctggat | ccaggtgaac | 720 |
| cttctgcgga | agatgcgggt | atcaggtgtg | atgacgcagg | gtgccagccg | tgccgggagg | 780 |
| gcggagtacc | tgaagacctt | caaggtggct | tacagcctcg | acggacgcaa | gtttgagttc | 840 |
| atccaggatg | aaagcggtgg | agacaaggag | tttttgggta | acctggacaa | caacagcctg | 900 |
| aaggttaaca | tgttcaaccc | gactctggag | gcacagtaca | taaagctgta | ccctgtttcg | 960 |
| tgccaccgcg | gctgcaccct | ccgcttcgag | ctcctgggct | gtgagttgca | cggatgttct | 1020 |
| gagcccctgg | gcctgaagaa | taacacaatt | cctgacagcc | agatgtcagc | ctccagcagc | 1080 |
| tacaagacat | ggaacctgcg | tgcttttggc | tggtaccccc | acttgggaag | gctggataat | 1140 |
| cagggcaaga | tcaatgcctg | gacggctcag | agcaacagtg | ccaaggaatg | gctgcaggtt | 1200 |
| gacctgggca | ctcagaggca | agtgacagga | atcatcaccc | agggggcccg | tgactttggc | 1260 |
| cacatccagt | atgtggcgtc | ctacaaggta | gcccacagtg | atgatggtgt | gcagtggact | 1320 |
| gtatatgagg | agcaaggaag | cagcaaggtc | ttccaggcac | acttggacaa | caactcccac | 1380 |
| aagaagaaca | tcttcgagaa | acccttcatg | gctcgctacg | tgcgtgtcct | tccagtgtcc | 1440 |
| tggcataacc | gcatcaccct | gcgcctggag | ctgctgggct | gttaatgctc | agtcctgcca | 1500 |
| gcccaaacga | tgaggatggc | cagaggctga | ggggcctcct | ggccctgcct | cccaggccct | 1560 |
| gctgccttct | gtggctgacg | accttcttgg | ccttcccttc | tgattgtact | ggggctggag | 1620 |
| gcaggaaggg | ccaggggatt | tcagagttgc | ccttcaccct | ttccctcacc | ctgcagcccc | 1680 |
| cacaggcctc | ctgctagccc | ccttctctca | ggcattctgg | gggagttgga | caggtctgag | 1740 |
| atgaatagag | aagaagagtg | aagttggggt | atgtgggcta | tctgtaccaa | ccaccccaag | 1800 |
| tcctaaactt | cctgccaggg | cttgactcag | gactgaaggg | agcccctgac | tgcccatccc | 1860 |
| tctctgcaca | ccacacattc | ctccatgttc | cattccggga | aggagaggcc | cacgtccgct | 1920 |
| tgctgtccct | tgggtcacca | ggtcctgcct | cttatctcct | gagacgcctc | ttgacccttg | 1980 |
| cactggagcc | tcagttgaca | aggagactgg | cgggtctgga | gaggtcggtg | gctctgggtg | 2040 |
| gttgacaggt | tggctgtggg | acctctgctg | gcttgctacc | caagttaaca | agcagattcc | 2100 | aaaatacatt cgtgttctcc actggaaaaa aaaaaaaaaa aaa 2143

<210> SEQ ID NO 20
<211> LENGTH: 463
<212> TYPE: PRT
<213> ORGANISM: Mus musculus

<400> SEQUENCE: 20

```
Met Gln Val Ser Arg Val Leu Ala Ala Leu Cys Gly Met Leu Leu Cys
 1               5                  10                  15

Ala Ser Gly Leu Phe Ala Ala Ser Gly Asp Phe Cys Asp Ser Ser Leu
            20                  25                  30

Cys Leu Asn Gly Gly Thr Cys Leu Thr Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
    130                 135                 140

Ala Ser Arg Cys Ser Thr Gln Leu Gly Met Glu Gly Gly Ala Ile Ala
145                 150                 155                 160

Asp Ser Gln Ile Ser Ala Ser Ser Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp Thr Ala Ser Asn Tyr Asp Ser Lys Pro Trp Ile Gln Val
        195                 200                 205

Asn Leu Leu Arg Lys Met Arg Val Ser Gly Val Met Thr Gln Gly Ala
    210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
                245                 250                 255

Asp Lys Glu Phe Leu Gly Asn Leu Asp Asn Asn Ser Leu Lys Val Asn
            260                 265                 270

Met Phe Asn Pro Thr Leu Glu Ala Gln Tyr Ile Lys Leu Tyr Pro Val
        275                 280                 285

Ser Cys His Arg Gly Cys Thr Leu Arg Phe Glu Leu Leu Gly Cys Glu
    290                 295                 300

Leu His Gly Cys Ser Glu Pro Leu Gly Leu Lys Asn Asn Thr Ile Pro
305                 310                 315                 320

Asp Ser Gln Met Ser Ala Ser Ser Tyr Lys Thr Trp Asn Leu Arg
                325                 330                 335

Ala Phe Gly Trp Tyr Pro His Leu Gly Arg Leu Asp Asn Gln Gly Lys
            340                 345                 350

Ile Asn Ala Trp Thr Ala Gln Ser Asn Ser Ala Lys Glu Trp Leu Gln
        355                 360                 365
```

Val Asp Leu Gly Thr Gln Arg Gln Val Thr Gly Ile Ile Thr Gln Gly
 370                 375                 380

Ala Arg Asp Phe Gly His Ile Gln Tyr Val Ala Ser Tyr Lys Val Ala
385                 390                 395                 400

His Ser Asp Asp Gly Val Gln Trp Thr Val Tyr Glu Glu Gly Ser
                405                 410                 415

Ser Lys Val Phe Gln Gly Asn Leu Asp Asn Asn Ser His Lys Lys Asn
            420                 425                 430

Ile Phe Glu Lys Pro Phe Met Ala Arg Tyr Val Arg Val Leu Pro Val
        435                 440                 445

Ser Trp His Asn Arg Ile Thr Leu Arg Leu Glu Leu Leu Gly Cys
    450                 455                 460

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttgtctcct gcgacttca                                                19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtggtccag ggtttctta                                                19

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caatgcaatg aagaactgga ctgt                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
tcctacatct tctgagtttg gtga                                          24

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcagggttcc aacgatgttg                                               20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcagccatcg actaggacag a                                             21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctgacagagg caccactgaa                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
catctccaga gtccagcaca                                               20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgacgtcact ggagttgtac gg                                            22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 31
ggttcatgtc atggatggtg c                                              21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aactttgaga aggatggcaa gt                                             22

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgccacccat ggtaaacaa                                                 19

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctggacagcc agacactaaa g                                              21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctcgcggcaa gtcttcagag                                                20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gctctctgct cctcctgttc                                                20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
```

```
ccatggtgtc tgagcgatgt                                                    20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agctcccgga aaagattgat g                                                  21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cagggtgctg gctgagtaga t                                                  21

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cacgcacgac gtcttcca                                                      18

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aagcggtcct ggcagaaat                                                     19
```

COMPOSITIONS AND METHODS FOR TREATING OR PREVENTING FIBROSIS

CROSS-REFERENCE TO RELATED APPLICATIONS

This application is a national-stage filing under 35 U.S.C. § 371 of PCT Application No. PCT/IB2019/001136, filed Oct. 24, 2019, which claims the benefit of Korean Application No. 10-2018-0128033/KR, filed on Oct. 25, 2018; Korean Application No. 10-2018-0128625/KR, filed on Oct. 26, 2018; and Korean Application No. 10-2018-0128204/KR, filed on Oct. 25, 2018; the entire contents of each of said applications are incorporated herein in their entirety by this reference.

SEQUENCE LISTING

The instant application contains a Sequence Listing which has been submitted in ASCII format via EFS-Web and is hereby incorporated by reference in its entirety. Said ASCII copy, created on Mar. 19, 2020, is named NXH-00325 SL.txt and is 66 KB in size.

BACKGROUND OF THE INVENTION

The process of tissue repair as a part of would healing involves two phases. The first phase is the regenerative phase, in which injured cells are replaced by cells of the same type. The second phase is the formation of fibrous tissues, also called fibroplasia or fibrosis, in which connective tissue replaces normal parenchymal tissues. The tissue repair process can become pathogenic if the fibrosis phase continues unchecked, leading to extensive tissue remodeling and the formation of permanent scar tissue.

Liver fibrosis is characterized by an excessive accumulation of extracellular matrix proteins including collagen. In the progression of liver fibrosis, damaged and dead hepatocytes from liver injuries recruit Kupffer cells at their lesion sites. These Kupffer cells secrete substantial quantities of cytokines, including transforming growth factor β1 (TGF-β1) to control liver inflammation. The elevated TGF-β1 causes the activation of quiescent hepatic stellate cells (HSCs) that proliferate and become extracellular matrix (ECM)-producing myofibroblast-like cells. The activated HSCs further accumulate excessive collagen-rich ECM in the liver, leading to contortions in normal liver architecture.

Liver fibrosis results from chronic inflammatory liver diseases or iterative liver damages. Causes for iterative liver injury and fibrosis include viral infections (hepatitis B and C), alcohol abuse, and nonalcoholic steatohepatitis (NASH). Liver fibrosis has the potential to develop into liver cirrhosis and cancer with higher mortality rates than those of other major cancers (lung, colorectal, stomach, or breast cancer). Accordingly, liver fibrosis remains a major cause of death with few therapeutic strategies, and there is a great need for treatment to reduce and prevent fibrosis.

SUMMARY OF THE INVENTION

The present invention is based, at least in part, on the discovery that a fragment of MFG-E8, hereinafter NP-011, is surprisingly effective in treating and/or preventing diseases including but not limited to fibrosis, cirrhosis, steatosis, and nonalcoholic steatohepatitis (NASH).

In certain aspects, provided herein is a polypeptide for treating and/or preventing diseases including but not limited to fibrosis, cirrhosis, steatosis, and NASH. In some embodiments, the polypeptide comprises an MFG-E8 polypeptide comprising an epidermal growth factor (EGF)-like domain, a C1 domain, and optionally a signal peptide, but lacking a functional C2 domain. In some embodiments, the polypeptide comprises an MFG-E8 polypeptide comprising an epidermal growth factor (EGF)-like domain, a C1 domain, and optionally a signal peptide, but lacking a medin polypeptide or a fragment thereof.

In certain embodiments, said MFG-E8 polypeptide lacks at least 1, 2, 3, 4, 5, 10, 15, 20, 25, 30, 35, 40, 45, 50, 55, 60, 65, 70, 75, 80, 85, 90, 95, 100, or 105 amino acids within the C-terminal domain comprising amino acids 226-335 of the MFG-E8 polypeptide. In some embodiments, the MFG-E8 polypeptide comprises at least 180, 190, 200, 210, 215, 220, 225, 230, 235, 240, 245, 250, 255, 260, 265, 270, 275, or 280 amino acids of the MFG-E8 polypeptide. In some embodiments, the MFG-E8 polypeptide comprises at least 75%, 80%, 85%, 86%, 87%, 88%, 89%, 90%, 91%, 92%, 93%, 94%, 95%, 96%, 97%, 98%, 99%, or 100% of the amino acids 1-225 of SEQ ID NO: 10 or SEQ ID NO: 12. In some embodiments, the MFG-E8 polypeptide comprises at least 75%, 80%, 85%, 86%, 87%, 88%, 89%, 90%, 91%, 92%, 93%, 94%, 95%, 96%, 97%, 98%, 99%, or 100% of the amino acids 24-225 of SEQ ID NO: 10 or SEQ ID NO: 12.

In preferred embodiments, the MFG-E8 polypeptide is not glycosylated.

In certain embodiments, said polypeptide further comprises a heterologous sequence, e.g., a FLAG tag, a HIS tag, and/or a Fc portion of an immunoglobulin. Such a heterologous sequence may extend the half life of the polypeptide in vivo.

In some embodiments, the polypeptide is capable of one or more biological activities including but not limited to: decreasing the expression level of TGF-β; decreasing TGF-β signaling; decreasing phosphorylation of SMAD, e.g., SMAD2, ERK, and/or any other phosphorylated proteins downstream of TGF-β; increasing NOTCH signaling; decreasing fibrosis-related gene expression including but not limited to Col1a1, Col1a2, or Acta2; decreasing interaction between TGF-β and one or more integrins, e.g., integrin β3 and/or integrin β5; decreasing proliferation of hepatic stellate cells (HSC); decreasing the expression level of matrix metallopeptidase 2 (MMP2), matrix metallopeptidase 12 (MMP12), TMP2, ERK, and/or SMAD2; increasing collagenase activity; and/or increasing collagen uptake by macrophages.

In some embodiments, the polypeptide is in a pharmaceutical composition comprising the polypeptide and one or more pharmaceutically acceptable carriers and/or diluents.

Also provided herein is a kit comprising the polypeptide.

In certain aspects, provided herein is an isolated nucleic acid molecule encoding said polypeptide. In some embodiments, the nucleic acid comprises at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the sequence identity to nucleotides 61-735 of SEQ ID NO: 9 or SEQ ID NO: 11. In some embodiments, the nucleic acid comprises at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the sequence identity to nucleotides 130-735 of SEQ ID NO: 9 or SEQ ID NO: 11. Also provided herein is a vector comprising the nucleic acid molecule, optionally wherein the vector is an expression vector or a viral vector. In some embodiments, the nucleic acid molecule is operatively linked to a promoter and/or other regulatory sequences. In some embodiments, the nucleic acid molecule and/or the vector are in a pharmaceutical composition suitable for administering to a subject. Such pharmaceutical composition may comprise one or more agents (e.g., liposomes, polymers) that aid the endocytosis and/or longer half-life in vivo, and/or reduce immune reactions against the composition in the subject.

In certain aspects, provided herein is a viral particle comprising said vector. In some embodiments, the viral particle is AAV. In certain some embodiments, the AAV comprising the viral vector is administered to a subject, e.g., a human, to treat and/or prevent diseases such as fibrosis, cirrhosis, steatosis, NASH, myocardial infarction, lung fibrosis, idiopathic pulmonary fibrosis, and/or Alzheimer's Disease.

In certain aspects, provided herein is a host cell comprising said vector. In some such embodiments, the host cell is a mammalian cell. In other embodiments, the host cell is a yeast cell, e.g., *Pichia pastoris*.

In certain aspects, provided herein is a method of producing a polypeptide by culturing the host cell in a culture medium, e.g., wherein the host cell secretes the polypeptide into the medium. In some embodiments, the method further comprises isolating the polypeptide from the medium and optionally further purifying the polypeptide to generate substantially pure polypeptide.

In some aspects, provided herein is a method of decreasing or inhibiting fibrosis in a subject by contacting a cell of the subject with the polypeptide. Also provided herein is a method of decreasing or inhibiting proliferation of HSC by contacting the HSC with the polypeptide. Additionally provided herein is a method of decreasing or inhibiting steatosis in a subject by contacting a cell of the subject with the polypeptide. In some embodiments, the subject in these methods is a mammal, such as a rat, mouse, or human, preferably a human.

In certain aspects, provided herein is a method of increasing the activity of a macrophage (e.g., an uptake of collagens or fibrotic tissues) by contacting a macrophage with the polypeptide. Such increase in the activity of a macrophage contributes to reversal of fibrosis in various tissues (e.g., liver, lung, etc.).

In certain aspects, provided herein is a method of treating or preventing a disorder in a subject in need thereof by administering to the subject the polypeptide. In some embodiments, the disorder is fibrosis (chronic or acute), cirrhosis, steatosis, NASH, and/or lung fibrosis.

In some embodiments, the polypeptide of present disclosure treats or prevents idiopathic pulmonary fibrosis (IPF). In addition to reducing or eliminating the fibrotic tissues, the polypeptide may also alter the expression level of IPF biomarkers. In some instances, the polypeptide may decrease the expression level of at least one biomarker selected from αSMA, collagen (Col1a1), TMP2, MMP2, MMP12, phosphorylated ERK, ERK, phosphorylated SMAD2, and SMAD2.

In other embodiments, the polypeptide of present disclosure treats or prevents myocardial infarction. The polypeptide may improve or increase the function of a heart following myocardial infarction, e.g., relative to improvement seen in a corresponding untreated subject. For example, the polypeptide may increase left ventricular ejection fraction and/or fraction shortening. Furthermore, the polypeptide may inhibit or decrease the fibrosis associated with myocardial infarction.

The present invention also contemplates a method of treating or preventing Alzheimer's Disease (AD). The subject of treatment may have a genetic mutation associated with AD. For example, the subject may have (i) at least one mutation in amyloid precursor protein (APP) selected from K670N/M671L, I716V, and V717I; and/or (ii) at least one mutation in PSEN1 selected from M146L and L286V. The polypeptide of present disclosure may improve the memory loss and/or behaviors associated with Alzheimer's disease. In addition, the polypeptide may alter the physiological and histopathological changes in the brain. For example, the polypeptide may decrease the amount of amyloid plaques, the amount of amyloid beta, the number of microglia, the level of neuroinflammation (or inflammation of brain), and/or the amount of glial fibrillary acidic protein (GFAP) in the brain of the subject, preferably in hippocampus and/or cortex of the brain of the subject.

The subject may also be treated with an additional agent that treats the disorder.

In some embodiments, the method does not induce amyloid formation in the subject.

The polypeptide may be administered to the subject via any of various routes, e.g., an intravenous, subcutaneous, intra-arterial, intraperitoneal, or intramuscular route.

In some embodiments, the subject in these methods is a mammal, e.g., a rat, mouse, or human, preferably a human.

BRIEF DESCRIPTION OF THE DRAWINGS

FIG. 1A-FIG. 1F show that NP-011 inhibits liver fibrosis and advantages of NP-011 for treating liver disease. (FIG. 1A) Overall schematic schedule for testing efficacy of the human recombinant proteins in liver fibrosis model. (FIG. 1B) Representative images of histological analysis (H&E and Sirius red staining) for the liver of normal mice, TAA-induced liver fibrosis model (Sham), and protein (MFG-E8, NP-011, NP-012, and NP-013) administered liver fibrosis model. Scale bar, 200 µm. (FIG. 1C) Comparison of quantitative fibrotic area in the livers of the mice. Bars represent the means±SD from three replicates in each group. *P<0.05, **P<0.01. (FIG. 1D) Comparison of mRNA expression for fibrotic markers (Col1a1, Col1a2, and Acta2) in the liver of normal mice, TAA-induced liver fibrosis model (Sham), and protein (MFG-E8, NP-011, NP-012, and NP-013) administered liver fibrosis model. Bars represent the means±SD from three replicates in each group. *P<0.05, **P<0.01. (FIG. 1E) Luciferase reporter assay for confirming TGF-β signaling pathway transcriptional activity from human HEK-293FT cells after 0.5 h, 1 h, 2 h treatment of NP-011 (500 ng/mL) or NP-013 (500 ng/mL). Bars represent the means±SD from three replicates in each group. *P<0.05, **P<0.01. (FIG. 1F) Gene Set Enrichment Assay (GSEA) data showing the significant enrichment of Notch signaling gene sets in NP-011 administered group, but not in MFG-E8 administered group, compared to Sham group.

(FIG. 2A) Overall schematic schedule for testing efficacy of the NP-011 in liver fibrosis model. (FIG. 2B) Representative images for comparing fibrotic areas (Sirius red stained areas) in the liver of normal mice, TAA-induced liver fibrosis model and NP-011-administered liver fibrosis model at various dose ranges (20 µg/kg~160 µg/kg). Scale bar, 200 µm. (FIG. 2C) Quantitative analysis of the fibrotic areas in the livers of tested mice in FIG. 2B. Bars represent the means±SD from four mice in each group. P<0.01. (FIG. 2D) Comparison of α-SMA (Acta2) expression in the liver of normal mice, TAA-induced liver fibrosis model, and NP-011-administered liver fibrosis model by quantitative PCR and immunostaining, respectively. Scale bar, 100 µm. Bars represent the means±SD from three replicates in each group. P<0.01. (FIG. 2E) Heatmap data shows fibrosis relevant genes observed in livers from normal mice, TAA-induced mice, and NP-011-administered liver fibrosis mice. (FIG. 2F) Comparison of TGF-β1 mRNA expression in advanced liver fibrosis model. Bars represent the means±SD from three replicates in each group. **P<0.01.

(FIG. 3A) Overall schematic schedule for testing efficacy of NP-011 in advanced liver fibrosis model. (FIG. 3B) Representative images for analyzing fibrotic areas in livers of normal mice, TAA-induced liver fibrosis model, and 40 µg/kg NP-011-administered liver fibrosis model with different frequencies of administrations (1, 2, 4, and 6 times). Scale bar, 50 µm. Quantitative analysis of the fibrotic areas for livers of normal mice, TAA-induced liver fibrosis model, and 40 µg/kg NP-011-administered liver fibrosis model presented in left panel. Bars represent the means±SD from four mice in each group. P<0.01. (FIG. 3C) Overall schematic schedule for testing efficacy of NP-011 in progressing liver fibrosis model. (FIG. 3D) Representative images for analyzing fibrotic areas in livers of normal mice, TAA-induced liver fibrosis model, and TAA-injected liver fibrosis model with co-administrations of NP-011. Scale bar, 100 µm. Quantitative analysis of the fibrotic areas of livers in normal mice, TAA-induced liver fibrosis model, and TAA-injected liver fibrosis model with co-administrations of NP-011. Bars represent the means±SD from five mice in each group. P<0.01. (FIG. 3E) Left panel: Graphical description represents human liver fibrosis model using human embryonic stem cell (hES)-derived hepatocytes and human primary HSCs treated with APAP. Middle panel: Representative images for analyzing hepatocytes and activated myofibroblasts with ALB (albumin; red) and α-SMA (a biomarker for fibrosis Acta2, green). Scale bar, 50 µm. Right panel: Quantitative analysis of the percentage of α-SMA positive cells in human liver fibrosis model. Bars represent the means±SD from five replicates in each group. **P<0.01.

(FIG. 4A) Overall schematic presentation of efficacy test of NP-011 in DMN-induced liver cirrhosis model. (FIG. 4B) Survival curves of DMN-induced cirrhosis model are shown for 10 rat per group. (FIG. 4C) Representative images for H&E staining and Immunohistochemistry analysis of rat liver tissues labelling alpha smooth muscle actin. (FIG. 4D) The quantification score of the fibrosis areas and both piecemeal and lobular necrosis in the livers of normal, DMN-induced liver cirrhosis model, and NP-011 administrated liver cirrhosis model, and quantification of the positive areas of alpha smooth muscle actin.

(FIG. 5A) Overall schematic presentation of efficacy test of NP-011 in MCD diet NASH model. (FIG. 5B) Representative images for Oil red O staining and (FIG. 5C) the quantification of the relative Oil red O positive areas in the liver of normal mice, MCD diet NASH model, and NP-011 administrated liver NASH model show the significant therapeutic efficacy of secretory NP-011. (FIG. 5D) Quantification of the degree of macrovesicular steatosis and microvesicular steatosis and hypertrophy in the livers of each group. Scale bar, 100 µm. Bars represent the means±SD from five mice in each group. **P<0.01, ANOVA followed by Tukey's multiple comparison test.

FIG. 7A-FIG. 7D show that NP-011 inhibits proliferation of HSCs. Actions of NP-011 on HSCs. (FIG. 7A and FIG. 7B) PLA assay for studying physical interaction between TGFBRI and integrin αvβ3/αvβ5. Red signals (white arrow heads) indicates the interaction between TGFBRI and Integrin β3 (FIG. 7A), and β5 (FIG. 7B). Quantitative analysis of the number of red signals in each cell. Bars represent the means±SD from five replicates in each group. *P<0.05, P<0.01. (FIG. 7C) Western blot (WB) and immunoprecipitation (IP) analysis of the regulation of TGF-β signaling in human HSCs and physical interaction between TGFBRI and Integrin β3/β5 in the presence of TGF-β1 (10 ng/mL) and/or NP-011 (500 ng/mL). (FIG. 7D) EdU incorporation assay for cell proliferation of human HSCs in the presence of TGF-β1, NP-011, and/or cilengitide trifluoroacetate (CT, inhibitor of integrin αvβ3 and αvβ5). Bars represent the means±SD from five replicates in each group. P<0.01.

(FIG. 7A) Comparison of MMP2 mRNA expression in human HSCs in the presence of TGF-β1, NP-011. Bars represent the means±SD from three replicates in each group. P<0.01. (FIG. 7B and FIG. 7C) Collagenase activity assay of cell lysates (FIG. 7B) and conditioned media (FIG. 7C) from the culture of control HSCs and TGF-β1-treated HSCs with/without NP-011 treatment. Bars represent the means±SD from three replicates in each group. P<0.01.

(FIG. 9A) Overall schematic schedule for macrophage differentiation from monocyte by treatment of PMA. (FIG. 9B) Representative images for differentiated macrophages (upper panel) and FITC-labelled beads uptake by differentiated macrophages (lower panel). Scale bar=10 µm (FIG. 9C) Flow cytometry results showed that the FITC beads were uptaken by differentiated macrophages. (FIG. 9D) Graphical description of fibrotic collagen uptake assay by differentiated macrophages with/without NP-011. (FIG. 9E) Quantitative analysis of the relative CUI (collagen uptake index) for control and NP-011 treatment. Bars represent the means±SD from three replicates in each group. **P<0.01.

(FIG. 11A) The organ distribution in healthy male mice at 30 minutes and 60 minutes after intravenously injection of NP-011 (160 µg/kg). (FIG. 11B and FIG. 11C) Quantitative analysis for the number of inflammatory relevant cells and blood biochemistry in male rat (FIG. 11B) and female rat (FIG. 11C) compared between normal and two NP-011 administration group.

FIG. 23A-FIG. 23C show that NP-011 reverses the symptoms of myocardial infarction, and increases heart function. Measurements of left ventricular ejection fraction (EF) and fraction shortening (FS) are shown for mice at 2 weeks (FIG. 23A), 4 weeks (FIG. 23B), or 8 weeks (FIG. 23C) after LAD ligation. Measurements are shown for mice treated with none (AMI; acute myocardial infarction), PBS (phosphate buffered saline), MFG-E8, or NP-011.

FIG. 24A) and fraction shortening (FS; FIG. 24B). Unlike MFG-E8, NP-011 shows a significant improvement over time in heart function.

FIG. 26A shows the images of H&E-stained cross-sectioned hearts of rats treated with none (AMI), PBS, MFG-E8, or NP-011. FIG. 26B shows the measurement of fibrosis area compared to overall cross-sectional area of hears from FIG. 26A.

FIG. 27A-FIG. 27E show that NP-011 reverses the behaviors and memory loss associated with Alzheimer's Disease. FIG. 27A shows a diagram of Alzheimer's Disease (AD) model 5XFAD mice and details of the in vivo studies. 5XFAD mice express human APP and PSEN1 transgenes with a total of five AD-linked mutations: the Swedish (K670N/M671L), Florida (1716V), and London (V717I) mutations in APP, and the M146L and L286V mutations in PSEN1. Behavioral and memory tests were performed after injection of NP-011 to 5XFAD. FIG. 27B shows the behavioral analysis of the AD model immediately after injection with NP-011 (at 3.5 months from the initiation of the study as shown in FIG. 27A). FIG. 27C shows the behavioral analysis of the AD model 3 months after injection with NP-011 (at 6.5 months from the initiation of the study as shown in FIG. 27A). FIG. 27D shows the result of the passive avoidance test of the AD model immediately after injection with NP-011 (at 3.5 months from the initiation of the study as shown in FIG. 27A). FIG. 27E shows the result of the passive avoidance test of the AD model 3 months after injection with NP-011 (at 6.5 months from the initiation of the study as shown in FIG. 27A).

FIG. 28A shows hippocampus and cortex of AD brains stained with thioflavin S that detects amyloid plaques, and FIG. 28B shows quantification of the amyloid plaques as stained by thioflavin S.

FIG. 29A shows hippocampus and cortex of AD brains stained with the 6E10 antibody that specifically recognizes amyloid beta, and FIG. 29B shows quantification of the amyloid beta in hippocampus and cortex of AD brains.

FIG. 30A shows hippocampus and cortex of AD brains stained with an IBA-1 antibody that recognizes microglia, and FIG. 30B shows quantification of the microglial cells in hippocampus and cortex of AD brains.

FIG. 31A shows hippocampus and cortex of AD brains stained for GFAP, and FIG. 30B shows quantification of GFAP in hippocampus and cortex of AD brains.

DETAILED DESCRIPTION OF THE INVENTION

Figure 1C:
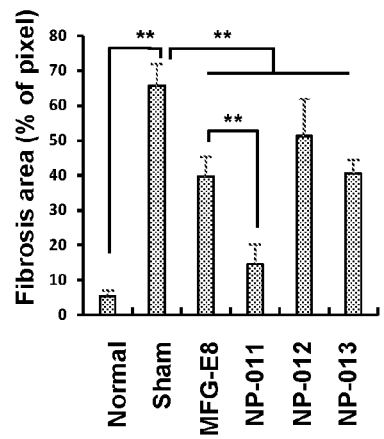

The present invention relates, in part, to compositions and methods for treating and/or preventing diseases related to fibrosis.

Definitions

Unless defined otherwise, all technical and scientific terms used herein have the same meaning as commonly understood by one of ordinary skill in the art to which this disclosure is related. The headings provided herein are not limitations of the various embodiments, which can be had by reference to the specification as a whole. Moreover, the terms defined immediately below are more fully defined by reference to the specification in its entirety.

The articles "a" and "an" are used herein to refer to one or to more than one (i.e. to at least one) of the grammatical object of the article. By way of example, "an" element means one element or more than one element.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal), then the treatment is prophylactic (i.e., it protects the host against developing the unwanted condition); whereas, if it is administered after manifestation of the unwanted condition, the treatment is therapeutic (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The amount (e.g., of expression of TGF-β, proliferation of HSC, NOTCH signaling) is "higher" or "lower" or "increased" or "decreased" than the amount of the control, if the amount is greater or less, respectively, than the control level by an amount greater than the standard error of the assay employed to assess amount, and preferably at least 5%, 10%, 20%, 30%, 40%, 50%, 60%, 70%, 80%, 90%, 100%, 150%, 200%, 300%, 350%, 400%, 500%, 600%, 700%, 800%, 900%, 1000% or than that amount. Such "significance" can be assessed from any desired or known point of comparison, such as a particular post-treatment versus pre-treatment measurement ratio (e.g., 1-fold, 1.1-fold, 1.2-fold, 1.3-fold, 1.4-fold, 1.5-fold, and the like). Alternately, the amount of the growth factor in the subject can be considered "significantly" higher or lower than the control amount if the amount is at least about two, three, four, or five times, higher or lower, respectively, than the normal amount of the biomarker. Such "significance" can also be applied to any other measured parameter described herein.

A "therapeutically effective amount" of e.g., a polypeptide is an amount capable of producing a medically desirable result in a treated patient, e.g., decrease in fibrosis, steatosis, decrease in expression of TGF-β, with an acceptable benefit: risk ratio, preferably in a human or non-human mammal.

The term "subject" refer to any subject, particularly a mammalian subject, for whom diagnosis, prognosis, or therapy is desired. Mammalian subjects include but are not limited to humans, non-human primates, domestic animals, farm animals, rodents, and the like, which is to be the recipient of a particular treatment.

By "increase in serum half life" or "increase in half life in vivo" means the positive change in circulating half-life of a modified biologically active molecule relative to its non-modified form. In some embodiments, serum half-life is measured by taking blood samples at various time points after administration of the biologically active molecule, and determining the concentration of that molecule in each sample. Measuring the change in serum concentration with time allows calculation of the serum half-life. By comparing the serum half-life of a modified molecule, e.g., conjugated molecule, with an unmodified molecule, the relative increase in serum half-life or $t_{1/2}$ may be determined.

A "kit" is any manufacture (e.g., a package or container) comprising at least one reagent, e.g., a polypeptide described herein. The kit may also comprise additional reagents, carriers, or diluents. The kit may be promoted, distributed, or sold as a unit for performing the methods of the present invention. The kit may comprise one or more reagents necessary to express a composition useful in the methods of the present invention. In certain embodiments, the kit may further comprise a reference standard. One skilled in the art can envision many such control. Reagents in the kit may be provided in individual containers or as mixtures of two or more reagents in a single container. In addition, instructional materials which describe the use of the compositions within the kit can be included.

Numeric ranges are inclusive of the numbers defining the range.

Polypeptides and Representative Biological Activities

The polypeptides provided herein for treatment of various diseases include a MFG-E8 polypeptide comprising an epidermal growth factor (EGF)-like domain, a C1 domain, and optionally a signal peptide, but lacking a functional C2 domain and/or a medin polypeptide or a fragment thereof. The MFG-E8 polypeptide may lack at least 1, 2, 3, 4, 5, 10, 15, 20, 25, 30, 35, 40, 45, 50, 55, 60, 65, 70, 75, 80, 85, 90, 95, 100, or 105 amino acids within the C-terminal domain of MFG-E8 comprising amino acids 226-335. The MFG-E8 polypeptide may comprise at least 180, 190, 200, 210, 215, 220, 225, 230, 235, 240, 245, 250, 255, 260, 265, 270, 275, or 280 amino acids. The MFG-E8 polypeptide may have at least about 75%, 80%, 85%, 86%, 87%, 88%, 89%, 90%, 91%, 92%, 93%, 94%, 95%, 96%, 97%, 98%, 99%, or 100% sequence identity to the amino acids 1-225 of SEQ ID NO: 10. The polypeptide may also have at least about 75%, 80%, 85%, 86%, 87%, 88%, 89%, 90%, 91%, 92%, 93%, 94%, 95%, 96%, 97%, 98%, 99%, or 100% sequence identity to the amino acids 2-225 of SEQ ID NO: 10. The MFG-E8 polypeptide may be of human or of any orthologs, e.g., mouse, rat, chimpanzee, horse, etc.

MFG-E8 is also called lactadherin. Representative human MFG-E8 cDNA and human BRD7 protein sequences are well-known in the art and are publicly available from the National Center for Biotechnology Information (NCBI). For example, four different human MFG-E8 isoforms are known. Human MFG-E8 isoform B (NP_001108086.1) is encodable by the transcript variant 2 (NM_001114614.3), which lacks an alternate in-frame exon compared to variant 1. The resulting isoform B has the same N- and C-termini but is shorter compared to isoform A. Human MFG-E8 isoform D (NP_001297248.1) is encodable by transcript variant 4 (NM_001310319.2), which lacks an alternate in-frame exon in the 5' coding region compared to transcript variant 1. The encoded isoform D has the same N- and C-termini but is shorter compared to isoform A. Human MFG-E8 isoform C (NP_001297249.1) is encodable by the transcript variant 3 (NM_001310320.2), which includes an alternate internal exon resulting in the use of an alternate translation start site, compared to variant 1. The encoded isoform C has a shorter distinct N-terminus compared to isoform A. Human MFG-E8 isoform E (NP_001297250.1) is encodable by the transcript variant 5 (NM_001310321.2), which includes an alternate 5' terminal exon resulting in the use of a downstream in-frame translation start site, compared to variant 1. The encoded isoform E has a shorter N-terminus than isoform A. Human MFG-E8 isoform A (NP_005919.2) is encodable by the transcript variant 1 (NM_005928.4), which encodes the longest isoform A. Nucleic acid and polypeptide sequences of MFG-E8 orthologs in organisms other than human are well know and include for example, chimpanzee MFG-E8 (XM_016927386.2→XP_016782875.1; and XM_001165898.6→XP_001165898.1), dog MFG-E8 (XM_022416924.1→XP_022272632.1), horse MFG-E8 (XM_023650241.1→XP_023506009.1; XM_023650222.1→XP_023505990.1; and XM_023650232.1→XP_023506000.1), pig MFG-E8 (XM_021098306.1→XP_020953965.1; and XM_013996945.2→XP_013852399.1), cat MFG-E8 (XM_011282749.2→XP_011281051.1; and XM_011282750.2→XP_011281052.1), sheep MFG-E8 (XM_027957063.1→XP_027812864.1), goat MFG-E8 (XM_018065819.1→XP_017921308.1), rat MFG-E8 (NM_001040186.2→NP_001035276.1; and NM_012811.3→NP_036943.1), and mouse MFG-E8 (NM_001045489.1→NP_001038954.1; and NM_008594.2→NP_032620.2).

A representative polypeptide is NP-011. NP-011 and other polypeptides described herein have many biological activities that are useful in inhibiting fibrosis. In some embodiments, polypeptides, such as NP-011, described herein decrease the expression of many genes including TGF-β1, MMP2, and/or fibrosis-related genes, e.g., Col1a1, Col1a2, Acta2.

In some embodiments, the polypeptides described herein modulate the signaling pathway, e.g., decreases TGF-β signaling or increases NOTCH signaling. TGF-β signaling controls a diverse set of cellular processes, including cell proliferation, recognition, differentiation, apoptosis, and specification of developmental fate, during embryogenesis as well as in mature tissues, in species ranging from flies and worms to mammals. A TGF-β ligand initiates signaling by binding to and bringing together type I and type II receptor serine/threonine kinases on the cell surface. This allows receptor II to phosphorylate the receptor I kinase domain, which then propagates the signal through phosphorylation of the Smad proteins. The activated Smad complexes are translocated into the nucleus and, in conjunction with other nuclear cofactors, regulate the transcription of target genes.

TGF-β and its signaling pathway regulate cell proliferation. In the progression of liver fibrosis, damaged and dead hepatocytes from liver injuries recruit Kupffer cells at their lesion sites. These Kupffer cells secrete substantial quantities of cytokines, including transforming growth factor β1 (TGF-β1) to control liver inflammation. The elevated TGF-β1 causes the activation of quiescent HSCs that proliferate and become extracellular matrix (ECM)-producing myofibroblast-like cells. The activated HSCs further accumulate excessive collagen-rich ECM in the liver, leading to contortions in normal liver architecture. Accordingly, decreasing the expression of TGF-β1 or decreasing TGF-β signaling inhibits activation and/or proliferation of HSCs, and results in inhibition of fibrosis. Similarly, NOTCH signaling is important for liver regeneration, and increase in NOTCH signaling demonstrates NP-011's role in promoting liver regeneration.

Decrease in TGF-β signaling may be monitored via many ways known in the art. For example, the level of expression of downstream target genes (e.g., ATF4, CDKN1A (p21CIP1, WAF1), CDKN1B (P27KIP1), CDKN2B (p15INK4b), COL1A1, COL1A2, DCN, EMP1, FOS, GADD45B, GSC, HERPUD1, IFRD1, IGF1, IGFBP3, IL6, JUN, JUNB, MYC, PDGFB, SERPINE1 (PAI-1), TGFB1I1, TNFSF10 (TRAIL), TSC22D1 (TGFB1I4), TGFBI, TGIF1) and/or phosphorylation of downstream proteins (e.g., SMAD) may be monitored. In addition, there are many commercially available kits that allow monitoring of the TGF-β signaling pathway, e.g., Qiagen Cat #PAHS-035Z, PAMM-035Z, PARN-035Z, PAHS-235Z, PAMM-235Z, PARN-235Z, CRHS-00035Z-100, CRHS-00245Z-100, CRMM-00035Z-100, CRMM-00235Z-100, CCS-017L, CCS-017G, CLS-017L, EAHS-251Z, GH-035A, SEH00508A, SEM02991A. Similarly, the level of expression of downstream target genes (e.g., CDKN1A (p21CIP1, WAF1), CFLAR (Casper), FOSL1 (fra-1), ID1, IL2RA (CD25), NFKB1, PTCRA, CD44, ERBB2 (HER-2, NEU), DTX1, HES1, HESS, HEY1, HEY2, HEYL, JAG1, KRT1, LFNG, LOR, NOTCH1, PPARG, CHUK (IKKα), IFNG, IL17B, IL2RA (CD25), NFKB1, NFKB2, STAT6) and/or phosphorylation of the downstream protein may be monitored to assess the Notch signaling pathway. For example, there are many commercially available kits that allow monitoring of the Notch signaling pathway, e.g., Qiagen Cat #PAHS-059Z, PAMM-059Z, PARN-059Z, CRHS-00059Z-100, CRMM-00059Z-100, CCS-014L, CCS-1014G, CLS-014L, CLS-014G, EAHS-611Z, GH-059A.

In some embodiments, as described above, the polypeptides described herein decrease the phosphorylation of SMAD, a protein in the TGF-β signaling pathway.

In some embodiments, the polypeptides described herein disrupt and/or decrease interaction between TGF-β receptor 1 (TGFBR1) and one or more integrins, e.g., integrin β3 and/or integrin β5.

In some embodiments, the polypeptides described herein decreases proliferation of HSCs.

In some embodiments, the polypeptides described herein increases collagenase activity and/or collagen uptake by macrophages.

Amyloid Formation

Certain polypeptides provided herein lack a medin polypeptide or a fragment thereof, which represents about 50 amino acids of the C2 domain. Medin is a major constituent of amyloid found in the aorta. Medin and the amyloid have been implicated in etiology of diseases including Alzheimer's disease and type 2 diabetes. Repeated administration of a polypeptide comprising the medin polypeptide may increase the risk of inducing amyloid formation. The polypeptides provided herein that lack the medin polypeptide or a fragment thereof reduce the risk of inducing amyloid formation.

Modification of a Polypeptide

The present invention further provides a modified polypeptide wherein the polypeptide described herein is fused in frame with a heterologous polypeptide and/or one or more chemical moieties. Such modification may be useful, for example, in extending the serum half-life of the polypeptide, serving as a tag during protein purification, or enhancing immunogenicity during production of antibodies to the polypeptide.

As used herein, a "chimeric protein" or "fusion protein" comprises all or part (preferably a biologically active part) of a polypeptide of the present invention linked to a heterologous polypeptide having an amino acid sequence corresponding to a protein which is not substantially homologous to the respective polypeptide. Within the fusion protein, the polypeptide of the present invention and the heterologous polypeptide are preferably fused to each other in such a way as to preserve their respective functions exhibited when expressed independently of the fusion. The heterologous polypeptide can be fused to the amino-terminus or the carboxyl-terminus of the polypeptide of the present invention.

In some embodiments, the fusion protein contains a heterologous signal sequence, immunoglobulin fusion protein, tag (e.g., FLAG, GST, etc.), toxin, or other useful protein sequence. Chimeric and fusion proteins of the present invention can be produced by standard recombinant DNA techniques. In other embodiments, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence. Moreover, many expression vectors are commercially available that already encode a fusion moiety (e.g., a GST polypeptide). A nucleic acid encoding a polypeptide of the present invention can be cloned into such an expression vector so that the fusion moiety is linked in-frame to the polypeptide of the present invention.

The heterologous peptide may optionally correspond to a moiety that alters the solubility, affinity, stability or valency of the polypeptide (e.g., NP-011). For example, a polypeptide such as NP-011 may be operably linked to an immunoglobulin constant region such as a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g., Fc receptor binding) or may be altered to reduce effector function. Such constant regions may also extend the serum half-life of the fusion protein. A resulting fusion protein may have altered solubility, binding affinity, stability and/or valency (i.e., the number of binding sites available per polypeptide) as compared to the independently expressed first peptide, and may increase the efficiency of protein purification. In preferred embodiments, the fusion protein retains the biological activity of the polypeptide.

In other embodiments, a polypeptide may be modified covalently or non-covalently with one or more chemical moieties, e.g., polyethylene glycol (PEG), lipids, or PEG-modified lipids. Such modification, for example, may increase the solubility, stability, and/or serum-half life of the polypeptide.

Therapeutic Methods—Exemplary Conditions

The compositions and methods provided herein are particularly useful in treating and/or preventing the disorders including those presented below.

Liver Fibrosis

In hepatic fibrosis, excessive connective tissue accumulates in the liver; this tissue represents scarring in response to chronic, repeated liver cell injury. Commonly, fibrosis progresses, disrupting hepatic architecture and eventually function, as regenerating hepatocytes attempt to replace and repair damaged tissue. When such disruption is widespread, cirrhosis is diagnosed.

Various types of chronic liver injury can cause fibrosis. Self-limited, acute liver injury (e.g., acute viral hepatitis A), even when fulminant, does not necessarily distort the scaffolding architecture and hence does not cause fibrosis, despite loss of hepatocytes. In its initial stages, hepatic fibrosis can regress if the cause is reversible (eg, with viral clearance). After months or years of chronic or repeated injury, fibrosis becomes permanent. Fibrosis develops even more rapidly in mechanical biliary obstruction.

Activation of the hepatic perivascular stellate cells (Ito cells, which store fat) initiates fibrosis. These and adjacent cells proliferate, becoming contractile cells termed myofibroblasts. These cells produce excessive amounts of abnormal matrix (consisting of collagen, other glycoproteins, and glycans) and matricellular proteins. Kupffer cells (resident macrophages), injured hepatocytes, platelets, and leukocytes aggregate. As a result, reactive oxygen species and inflammatory mediators (e.g., platelet-derived growth factor, transforming growth factors, connective tissue growth factor) are released. Thus, stellate cell activation results in abnormal extracellular matrix, both in quantity and composition.

Myofibroblasts, stimulated by endothelin-1, contribute to increased portal vein resistance and increase the density of the abnormal matrix. Fibrous tracts join branches of afferent portal veins and efferent hepatic veins, bypassing the hepatocytes and limiting their blood supply. Hence, fibrosis contributes both to hepatocyte ischemia (causing hepatocellular dysfunction) and portal hypertension. The extent of the ischemia and portal hypertension determines how the liver is affected. For example, congenital hepatic fibrosis affects portal vein branches, largely sparing the parenchyma. The result is portal hypertension with sparing of hepatocellular function.

Cirrhosis

Cirrhosis is a late stage of hepatic fibrosis that has resulted in widespread distortion of normal hepatic architecture. Cirrhosis is characterized by regenerative nodules surrounded by dense fibrotic tissue. Symptoms may not develop for years and are often nonspecific (e.g., anorexia, fatigue, weight loss). Late manifestations include portal hypertension, ascites, and, when decompensation occurs, liver failure. Diagnosis often requires liver biopsy. Cirrhosis is usually considered irreversible. Treatment is supportive.

Cirrhosis is the seventh leading cause of death in the United States, according to the National Institute of Diabetes and Digestive and Kidney Diseases (NIDDK). Cirrhosis is defined pathologically by the loss of normal microscopic lobular architecture with fibrosis (i.e., the growth of scar tissue due to infection, inflammation, injury, or even healing) and nodular regeneration. Because of chronic damage to the liver, scar tissue slowly replaces normal functioning liver tissue resulting in progressively diminishing blood flow through the liver. As the normal liver tissue is lost, nutrients, hormones, drugs and poisons are not processed effectively by the liver. In addition, protein production and other substances produced by the liver are inhibited.

Symptoms of cirrhosis vary, depending on severity and individuals. Symptoms may include abnormal nerve function, ascites (build-up of fluid in the abdominal cavity), breast enlargement in men, coughing up or vomiting blood, curling of fingers (Dupuytren contracture of the palms), gallstones, hair loss, itching, jaundice, kidney failure, liver encephalopathy, muscle loss, poor appetite, portal hypertension, redness of palms, salivary gland enlargement in cheeks, shrinking of testes, small spider-like veins in skin, weakness, weight loss, etc. The symptoms of cirrhosis may resemble other conditions or medical problems. Mild cirrhosis may not exhibit any symptoms at all.

The most common cause of cirrhosis is alcohol abuse. Other causes include hepatitis and other viruses (e.g., HCV as described in Section 2.2 infra.), use of certain drugs, chemical exposure, bile duct obstruction, autoimmune diseases, obstruction of outflow of blood from the liver (i.e., Budd-Chiari syndrome), heart and blood vessel disturbances, alpha1-antitrypsin deficiency, high blood galactose levels, high blood tyrosine levels, glycogen storage disease, diabetes, malnutrition, hereditary accumulation of too much copper (Wilson Disease) or iron (hemochromatosis).

Cirrhosis is a progressive liver disease, and the damage sustained by the liver is irreversible. However, with proper nutrition, avoidance of certain toxins (i.e., alcohol), vitamin supplementation, and management of cirrhosis complications, further liver damage can often be delayed or stopped. In severe cases of cirrhosis, liver transplantation may be considered.

Nonalcoholic Steatohepatitis (NASH)

Non-alcoholic steatohepatitis (NASH), also known as non-alcoholic fatty liver disease, describes a hepatic disorder typically characterized by an alcoholic pathogenesis without alcohol consumption. The fat deposit in liver cells is mostly triglyceride, and the severity of NASH is directly related to the amount of fat in the liver. Histologically, if 50% of liver cells had steatosis (fatty liver accumulation), or if the total weight of fat is greater than 5% of the entire liver, then steatohepatitis can be diagnosed. NASH is further characterized by elevated serum aminotransferase activities with hepatic steatosis, inflammation, and occasionally fibrosis that may progress to cirrhosis.

The prevalence of NASH is 3-19% throughout most of the world. There are many possible causes of NASH but there isn't a definite source. The most likely causes are obesity from poor diet, diabetes, long-term use of steroids and use of tetracycline. Some studies have shown sign of steatosis reversal after weight loss.

There is currently no established treatment that exists for this potentially serious disorder. Treatment of patients with nonalcoholic fatty liver has typically been focused on the management of associated conditions such as obesity, diabetes mellitus, and hyperlipidemia as well as discontinuation of potentially hepatotoxic drugs.

Fibrosis Related Disorders

Fibrosis related disorders that may be amenable to treatment with the methods provided herein include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS-associated pulmonary hypertension, sarcoidosis, moderate to severe asthma and the like), fibrotic vascular disease, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport syndrome, HIV-associated nephropathy, polycystic kidney disease, Fabry's disease, diabetic nephropathy, chronic glomerulonephritis, nephritis associated with systemic lupus, and the like), progressive systemic sclerosis (PSS), primary sclerosing cholangitis (PSC), liver fibrosis, liver cirrhosis, renal fibrosis, pulmonary fibrosis, cystic fibrosis, chronic graft versus host disease, scleroderma (local and systemic), Grave's ophthalmopathy, diabetic retinopathy, glaucoma, Peyronie's disease, penis fibrosis, urethrostenosis after cystoscope, inner accretion after surgery, scarring, myelofibrosis, idiopathic retroperitoneal fibrosis, peritoneal fibrosis from a known etiology, drug-induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), stromal cell tumors, mucositis, fibrosis induced by chemical or environmental insult (e.g., cancer chemotherapy, pesticides, radiation (e.g., cancer radiotherapy), and the like), and the like. In some embodiments, the fibrosis related disorder is selected from systemic or local scleroderma, keloids, hypertrophic scars, atherosclerosis, restenosis, pulmonary inflammation and fibrosis, idiopathic pulmonary fibrosis, liver cirrhosis, fibrosis as a result of chronic hepatitis B or C infection, kidney disease, heart disease resulting from scar tissue, macular degeneration, and retinal and vitreal retinopathy. In some embodiments, the fibrosis related disorder results from chemotherapeutic drugs, radiation-induced fibrosis, and injuries and burns.

Inherited disorders associated with hepatic fibrosis include Wilson's disease, hereditary hemochromatosis, non-HFE hereditary hemochromatosis ferroportin, Transferrin receptor 2, Hepcidin, Hemojuvelin, Sitosterolemia/hepatobiliary cholesterol transporter 5 and 8, progressive familial intrahepatic cholestasis type 3, hereditary fructose intolerance, tyrosinemia type I, argininosuccinate lyase deficiency, citrin deficiency, cholesteryl ester storage disease and Wolman disease, anti-1 antitrypsin deficiency, cystic fibrosis, Alstrom syndrome, and congenital hepatic fibrosis.

Lung Fibrosis

Lung fibrosis ("scarring of the lungs") is a respiratory disease in which scars are formed in the lung tissues, leading to serious breathing problems. Scar formation, the accumulation of excess fibrous connective tissue (the process called fibrosis), leads to thickening of the walls, and causes reduced oxygen supply in the blood. A consequence is a perpetual shortness of breath.

Lung fibrosis involves gradual exchange of normal lung parenchyma with fibrotic tissue. The replacement of normal lung with scar tissue causes irreversible decrease in oxygen diffusion capacity, and the resulting stiffness or decreased compliance makes lung fibrosis a restrictive lung disease. Lung fibrosis is perpetuated by aberrant wound healing, rather than chronic inflammation. It is the main cause of restrictive lung disease that is intrinsic to the lung parenchyma. In some cases, lung fibrosis has been associated with cigarette smoking. Treatment option for lung fibrosis is limiting, and includes immunosuppressive therapy such as corticosteroids.

Idiopathic Pulmonary Fibrosis

Idiopathic pulmonary fibrosis (IPF), the most common form of the idiopathic interstitial pneumonias, is a chronic, progressive, irreversible, and usually lethal lung disease of unknown cause. IPF occurs in middle-aged and elderly adults (median age at diagnosis 66 years, range 55-75 years), is limited to the lungs, and is associated with a histopathological or radiological pattern typical of usual interstitial pneumonia.

The main histopathological features of usual interstitial pneumonia, best seen at low magnification, is a heterogeneous appearance with areas of subpleural and paraseptal fibrosis and honeycombing (i.e., cystic fibrotic airspaces lined by bronchiolar epithelium and often filled by mucin and variable numbers of inflammatory cells) alternating with areas of less affected or normal parenchyma (spatial heterogeneity). Small areas of active fibrosis (fibroblast foci) are present in the background of collagen deposition, and they reflect the temporal heterogeneity of the process and indicate current ongoing disease. Inflammation is usually mild and consists of a patchy lymphoplasmacytic interstitial infiltrate. The presence of a usual-interstitial-pneumonia pattern on high-resolution CT is characterised by reticular opacities, often associated with traction bronchiectasis, with little or no ground-glass opacifications. Honeycombing, manifested as subpleural, clustered cystic airspaces with well-defined walls (typically 3-10 mm in diameter), is common and is critical for making a definite diagnosis.

Patients with IPF usually seek medical attention because they suffer chronic and progressive exertional dyspnoea and cough. Bibasilar inspiratory crackles are heard on chest auscultation and frequently finger clubbing is found. The natural history of IPF has been characterised as a steady or slowly progressive lung disorder, and most patients follow this pattern. However, recent findings indicate that IPF is a heterogeneous disease and new clinical phenotypes with distinct patterns of survival are being described. The pathogenic mechanisms are unclear, but a growing body of evidence indicates that the disease is the result of an abnormal behaviour of the alveolar epithelial cells that provoke the migration, proliferation, and activation of mesenchymal cells, with the formation of fibroblast and myofibroblast foci. Activated myofibroblasts secrete exaggerated amounts of extracellular matrix molecules with the subsequent destruction of the lung architecture. No therapy has been clearly shown to prolong survival.

Myocardial Infarction

A myocardial infarction, commonly known as a heart attack, occurs when a portion of the heart is deprived of oxygen due to blockage of a coronary artery. Coronary arteries supply the heart muscle (myocardium) with oxygenated blood. Without oxygen, muscle cells served by the blocked artery begin to die (infarct).

The most common cause of a myocardial infarction is the rupture of an atherosclerotic plaque on an artery supplying heart muscle. Plaques can become unstable, rupture, and additionally promote the formation of a blood clot that blocks the artery; this can occur in minutes. Blockage of an artery can lead to tissue death in tissue being supplied by that artery. Atherosclerotic plaques are often present for decades before they result in symptoms.

The gradual buildup of cholesterol and fibrous tissue in plaques in the wall of the coronary arteries or other arteries, typically over decades, is termed atherosclerosis. Atherosclerosis is characterized by progressive inflammation of the walls of the arteries. Inflammatory cells, particularly macrophages, move into affected arterial walls. Over time, they become laden with cholesterol products, particularly LDL, and become foam cells. A cholesterol core forms as foam cells die. In response to growth factors secreted by macrophages, smooth muscle and other cells move into the plaque and act to stabilize it. A stable plaque may have a thick fibrous cap with calcification. If there is ongoing inflammation, the cap may be thin or ulcerate. Exposed to the pressure associated with blood flow, plaques, especially those with a thin lining, may rupture and trigger the formation of a blood clot (thrombus).

Alzheimer's Disease

Alzheimer's Disease is a dementing disorder characterized by progressive impairments in memory and cognition. It typically occurs in later life; and is associated with a multiplicity of structural, chemical and functional abnormalities involving brain regions concerned with cognition and memory. Epidemiologic studies suggest that the dementia presently occurs in up to 10% of individuals over the age of 65 and it is estimated that in the United States alone, as many as 4 million individuals may be affected with Alzheimer's Disease. The cost of caring for such individuals is well over 80 billion dollars annually and increasing rapidly.

The cause of Alzheimer's disease is poorly understood. About 70% of the risk is believed to be inherited from a person's parents with many genes usually involved. Other risk factors include a history of head injuries, depression, and hypertension. The disease process is associated with plaques and neurofibrillary tangles in the brain. A probable diagnosis is based on the history of the illness and cognitive testing with medical imaging and blood tests to rule out other possible causes. Initial symptoms are often mistaken for normal ageing. Examination of brain tissue is needed for a definite diagnosis. There are no medications or supplements that have been shown to decrease risk.

It has been postulated that extracellular amyloid beta ($A_\beta$) deposits are the fundamental cause of the disease. Support for this postulate comes from the location of the gene for the amyloid precursor protein (APP) on chromosome 21, together with the fact that people with trisomy 21 (Down Syndrome) who have an extra gene copy almost universally exhibit at least the earliest symptoms of AD by 40 years of age. Also, a specific isoform of apolipoprotein, APOE4, is a major genetic risk factor for AD. While apolipoproteins enhance the breakdown of beta amyloid, some isoforms are not very effective at this task (such as APOE4), leading to excess amyloid buildup in the brain. Further evidence comes from the finding that transgenic mice that express a mutant form of the human APP gene develop fibrillar amyloid plaques and Alzheimer's-like brain pathology with spatial learning deficits.

Additional Agents

The compositions provided herein may be administered to a subject in combination with any known agents that treat the disorder, e.g., liver fibrosis. Similarly, the methods provided herein may administer the subject any known agents that treat the disorder in combination with the compositions (e.g., NP-011) disclosed herein. Various treatments for fibrosis-related disorders are known to those skilled in the art.

Treatments for fibrotic disorders include anti-inflammatory agents, corticosteroids, penicillamine, and colchicine. See e.g., The Merck Manual. 20th ed. Merck Research Laboratories, 2018.

Because fibrosis represents a response to hepatic damage, primary treatment should focus on the cause (removing the basis of the liver injury). Such treatment may include eliminating hepatitis B virus or hepatitis C virus in chronic viral hepatitis, abstaining from alcohol in alcoholic liver disease, removing heavy metals such as iron in hemochromatosis or copper in Wilson disease, and decompressing bile ducts in biliary obstruction. Such treatments may stop the fibrosis from progressing and, in some patients, also reverse some of the fibrotic changes.

Treatments aimed at reversing the fibrosis are usually too toxic for long-term use (e.g., corticosteroids, penicillamine) or have no proven efficacy (eg, colchicine). Other antifibrotic treatments are under study. Silymarin, present in milk thistle, is a popular alternative medicine used to treat hepatic fibrosis. It appears to be safe (except when combined with certain drugs to treat hepatitis C) but lacks efficacy.

In some embodiments, anti-fibrotic therapy includes administration of profibrotic factor antagonists and/or antifibrotic agents.

Profibrotic Factor Antagonists

Anti-fibrotic therapy encompasses agents that inhibit or antagonize profibrotic factors, such as agents that antagonize one or more growth factors or cytokines involved in the formation and maintenance of fibrotic tissue. In this manner, anti-fibrotic therapy targets fibrocyte, fibrocyte precursor, myofibroblast precursor, and/or hematopoetic monocyte precursor differentiation and fibrotic tissue formation and maintenance.

Pro fibrotic factors that may be targeted with antagonists as part of the therapies of the present invention include, without limitation, a transforming growth factor type β (TGF-β, including TGF-β1-5), VEGF, EGF, RANTES, members of the interleukin family (e.g., IL-1, IL-4, IL-5, IL-6, IL-8 and IL-13), tumor necrosis factor type alpha (TNF-α), platelet-derived growth factor (PDGF), basic fibroblast growth factor (bFGF), monocyte chemoattractant protein type 1 (MCP-1), macrophage inflammatory protein (e.g., MIP-1a, MIP-2), connective tissue growth factor (CTGF), endothelin-1, angiotensin-11, rennin, leptin, chemokines (e.g., CCL2, CCL12, CXCL12, CXCR4, CCR3, CCR5, CCR7), SLC/CCL21 and other factors known to promote or be related to the formation, growth, or maintenance of fibrotic tissue.

Anti-fibrotic therapy may include antagonists of the corresponding receptor of one or more of the pro fibrotic factors. Such antagonists may include inactive forms of one or more of the pro fibrotic factors and/or cytokines, such as fragments thereof. Such forms in suitable concentrations may compete with its corresponding profibrotic factors and/or cytokines for binding to its receptor. Similarly, certain antibodies to the receptor may be used to interfere with or prevent binding thereto of the corresponding pro fibrotic factors and/or cytokines.

Anti-fibrotic therapy may also include soluble forms of the receptor of one or more of the pro fibrotic factors and/or cytokines, such that the soluble receptor competes with its corresponding native cellular receptor for the target ligand. The therapy may further include compounds that compete with or otherwise interfere with binding of one or more of the profibrotic factors and/or cytokines with its receptor. For example, the proteoglycan decorin is known to bind to TGF-β, thereby reducing its availability for binding to its receptor. Mannose-6-phosphate is also known to compete with TGF-β for binding to its corresponding receptor. Other known binding inhibitors of TGF-β include latent transforming growth factor-β binding protein (LTBP) and latency associated peptide (LAP), both of which natively bind to the intracellular precursor of TGF-β.

In certain embodiments, anti-fibrotic therapy may include one or more oligoribonucleotides that contain at least one sequence that is antisense with respect to one or more of the profibrotic factors and/or cytokines. Such components may also include one or more expression plasmids having suitable transcriptional control sequences that yield antisense sequences. In other selected embodiments, anti-fibrotic therapy may include one or more double-stranded oligoribonucleotides, or expression plasmids encoding thereof, that are suitable for degrading transcripts of one or more of the profibrotic factors and/or cytokines via RNA mediated interference. In other selected embodiments, anti-fibrotic therapy may include one or more single-stranded oligonucleotide aptamers, or expression plasmids encoding thereof, that are suitable for inhibiting or interfering with the binding of pro fibrotic factors to their cognate receptors.

A suitable profibrotic factor antagonist may include components known to inhibit, attenuate, or interfere with one or more components of the intracellular signaling pathways activated by one or more of the pro fibrotic factors upon binding to its corresponding receptor. For example, anti-fibrotic therapy may include components that inhibit or attenuate downstream signal pathway molecules such as SMAD family members and SARA. A suitable anti-fibrotic therapy may include one or more molecules that are suitable for inhibiting or interfering with the cellular adhesions require for fibrosis. For example, a suitable component may include interfering antibodies to the ICAM-1 and/or CD 11, CD 49 or CD 18 molecules, thereby interfering with the adhesion interaction there between.

In other selected embodiments, a suitable profibrotic factor antagonist may include inhibitors of collagen synthesis, such as proline analogs that interfere with post-translation processing of collagen precursors. Pirfenidone, for example, is an orally active small molecule drug that may inhibit collagen synthesis, downregulate production of multiple cytokines and block fibroblast proliferation.

TGF-β Antagonists

Cytokines of the transforming growth factor (TGF) beta family play a central role in wound healing and in tissue repair, and are found in all tissues. TGF-β is produced by many parenchymal cell types, as well as infiltrating cells such as lymphocytes, monocytes/macrophages, and platelets. Following wounding or inflammation, such cells such are potential sources of TGF-β. In general, TGF-β stimulates the production of various extracellular matrix proteins, inhibits the degradation of these matrix proteins, and promotes tissue fibrosis, all of which contribute to the repair and restoration of the affected tissue. In many diseases, excessive TGF-β contributes to a pathologic excess of tissue fibrosis that can compromise normal organ function.

Examples of TGF-β antagonists include, but are not limited to: monoclonal and polyclonal antibodies directed against one or more isoforms of TGF-β (Dasch et al., U.S. Pat. No. 5,571,714; see, also, WO 97/13844 and WO00/66631); TGF-β receptors, soluble forms of such receptors (preferably soluble TGF-P type III receptor), or antibodies directed against TGF-β receptors (Segarini et al., U.S. Pat. No. 5,693,607; Lin et al., U.S. Pat. Nos. 6,001,969, 6,010,872, 6,086,867, 6,201,108; WO 98/48024; WO 95/10610; WO 93/09228; WO 92/00330); latency associated peptide (WO 91/08291); large latent TGF-β (WO 94/09812); fetuin (U.S. Pat. No. 5,821,227); decorin and other proteoglycans such as biglycan, fibromodulin, lumican and endoglin (WO 91/10727; Ruoslahti et al., U.S. Pat. Nos. 5,654,270, 5,705,609, 5,726,149; Border, U.S. Pat. No. 5,824,655; WO 91/04748; Letarte et al., U.S. Pat. Nos. 5,830,847, 6,015,693; WO 91/10727; WO 93/09800; and WO 94/10187); somatostatin (WO 98/08529); mannose-6-phosphate or mannose-1-phosphate (Ferguson, U.S. Pat. No. 5,520,926); prolactin (WO 97/40848); insulin-like growth factor II (WO 98/17304); IP-10 (WO 97/00691); arg-gly-asp containing peptides (Pfeffer, U.S. Pat. No. 5,958,411; WO 93/10808); extracts of plants, fungi and bacteria (EP-A-813 875; JP 8119984; and Matsunaga et al., U.S. Pat. No. 5,693,610); antisense oligonucleotides (Chung, U.S. Pat. No. 5,683,988; Fakhrai et al., U.S. Pat. No. 5,772,995; Dzau, U.S. Pat. Nos. 5,821,234, 5,869,462; and WO 94/25588); proteins involved in TGF-β signaling, including SMADs and MADs (EP-A-874 046; WO 97/31020; WO 97/38729; WO 98/03663; WO 98/07735; WO 98/07849; WO 98/45467; WO 98/53068; WO 98/55512; WO 98/56913; WO 98/53830; WO 99/50296; Falb, U.S. Pat. No. 5,834,248; Falb et al., U.S. Pat. No. 5,807,708; and Gimeno et al., U.S. Pat. No. 5,948,639), Ski and Sno (Vogel, 1999, Science, 286:665; and Stroschein et al., 1999, Science, 286:771-774); one or more single stranded oligonucleotide aptamers, or expression plasmids encoding thereof, that are suitable for inhibiting or interfering with the binding of TGF-β to its cognate receptors; and any mutants, fragments or derivatives of the above-identified molecules that retain the ability to inhibit the activity of TGF-β.

In some embodiments, the TGF-β antagonist is a human or humanized monoclonal antibody that blocks TGF-β binding to its receptor (or fragments thereof such as F(ab)2 fragments, Fv fragments, single chain antibodies and other forms or fragments of antibodies that retain the ability to bind to TGF-β, e.g., a monoclonal antibody from hybridoma 1 D 11.16 (ATCC Accession No. HB 9849 described in Dasch et al., U.S. Pat. No. 5,783,185).

Anti-Fibrotic Agents

In certain embodiments, the profibrotic factor antagonists can be replaced with, or augmented with, a cytokine known to have anti-fibrotic effects, such as IL-12, IL-10, IFN-g or BMP-7 (OP-1). The nucleic acid sequences encoding IFN-y polypeptides may be accessed from public databases, e.g. Genbank, journal publications, etc. While various mammalian IFN-g polypeptides are of interest, for the treatment of human disease, generally the human protein will be used. Human IFN-g coding sequence may be found in Genbank, accession numbers P01579 and CAA00375. The corresponding genomic sequence may be found in Genbank, accession numbers 100219; M37265; and V00536. See, for example. Gray et al. (1982) Nature 295:501 (Genbank X13274); and Rinderknecht et al. (1984) J. Biol. Chem. 259:6790. IFN-g1b (Actimmune®; human interferon) is a single-chain polypeptide of 140 amino acids. It is made recombinantly in *E. coli* and is unglycosylated. Rinderknecht et al. (1984) J. Biol. Chem. 259:6790-6797. The IFN-g to be used in anti-fibrotic therapy may be any of natural IFN-g, recombinant IFN-g and the derivatives thereof so far as they have a IFN-g activity, particularly human IFN-g activity.

Anti-fibrotic therapy comprises one or more Serum amyloid P(SAP) agonists, one or more C-relative protein (CRP) antagonists, or a combination thereof. SAP agonists are useful in the treatment of various fibrotic disorders. SAP agonists encompass all compounds and compositions that increase or otherwise mimic endogenous SAP signaling, including compounds that increase SAP activity.

Serum amyloid P(SAP) or pentraxin-2, a member of the pentraxin family, is a 27-kDa protein that is produced by the liver, secreted into the blood, and circulates as stable 135-kDa pentamers. SAP reduces neutrophil adhesion to ECM proteins, inhibits the differentiation of monocytes into fibrocytes, decreases profibrotic macrophages, activates the complement pathway, and promotes phagocytosis of cell debris. SAP reduces bleomycin-induced lung fibrosis. Representative agonists of SAP includes human SAP protein or an active fragment thereof, anti-FcyR antibodies, aggregated antibodies, SAP peptidomimetic, FcyR crosslinkers, and aptamers. CRP antagonists encompass all compounds and compositions that decrease, block, or inhibit CRP signaling. Representative antagonists include an anti-sense nucleic acid that targets the expression of CRP, RNA interference molecules, e.g., short interfering RNA, dsRNA, and Locked Nucleic Acids (LNAs).

Nucleic Acid Molecules, Vectors, Host Cells

Nucleic acid molecules that encode the polypeptides disclosed herein, e.g., the NP-011 protein, are provided.

Nucleic acid molecules disclosed herein can be in the form of RNA or in the form of DNA. DNA includes cDNA, genomic DNA, and synthetic DNA; and can be double-stranded or single-stranded, and if single stranded can be the coding strand/or non-coding (anti-sense) strand. In certain embodiments, the nucleic acid molecule is isolated. In additional embodiments, a nucleic acid molecule is substantially pure. In some embodiments, the nucleic acid is cDNA or is derived from cDNA. In some embodiments, the nucleic acid is recombinantly produced.

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

In some embodiments, the nucleic acid molecule comprises a protein coding sequence operably linked to a control sequence that controls the expression of the coding sequence in a host cell or in vitro (see below). In particular embodiments, the coding sequence is a cDNA. The disclosure also relates to vectors containing nucleic acid molecules that comprise a protein (e.g., NP-011) coding sequence operably linked to a control sequence that controls the expression of the coding sequence in a host cell or in vitro.

In some embodiments, the nucleic acid molecule comprises a coding sequence for a protein that is fused in the same reading frame to a heterologous polynucleotide sequence. In some embodiments, the heterologous polynucleotide sequence encodes a leader peptide sequence that facilitates the secretion of the expressed protein from the host cell transformed with the polypeptide (e.g., NP-011) encoding nucleic acid molecule(s). A protein containing a leader sequence is referred to as a preprotein and can have the leader sequence cleaved by the host cell to form the processed form of the protein. Such leader peptide sequences and their use facilitating the secretion of recombinant proteins in host cells is generally known in the art. In additional embodiments, the heterologous polynucleotide sequence encodes additional 5' amino acid residues that can function for example, to facilitate purification, add or improve protein stability and/or therapeutic properties of the recombinantly expressed protein. In preferred embodiments, NP-011 and/or similar proteins are secreted from the host cells. In certain preferred embodiments, NP-011 and/or similar proteins lack the N-terminal methionine and do not comprise a heterologous sequence. In other preferred embodiments, NP-011 comprises a heterologous sequence that extends the half-life in vivo.

In some embodiments, a nucleic acid sequence encoding the protein or a vector comprising said nucleic acid sequence is constructed by chemical synthesis using an oligonucleotide synthesizer. Such oligonucleotides can be designed based on the amino acid sequence of the desired polypeptide and codon optimization based on the host cell preferences. Standard methods can routinely be applied to synthesize and isolate polynucleotide sequences encoding the polypeptide (e.g., NP-011).

The vector may be a construct, which is capable of delivering, and in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Once assembled (by synthesis or another method), the nucleic acid sequences encoding the polypeptide can routinely be operably linked to a control sequence appropriate for expression in a desired host. In some embodiments, the nucleic acid sequence(s) encoding the polypeptide is inserted into one or more expression vectors and operably linked to a control sequence(s) appropriate for expression of the protein in a desired host. In order to obtain high expression levels of a transfected coding sequence in a host, the coding sequence can be operably linked to or associated with transcriptional and translational expression control sequences that are functional in the chosen expression host.

In certain embodiments, recombinant expression vectors are used to amplify and express DNA encoding the polypeptide. Recombinant expression vectors are replicable DNA constructs which have synthetic or cDNA-derived DNA fragments encoding the polypeptide (e.g., NP-011) operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final protein. In certain embodiments, the disclosure provides a composition, e.g., a pharmaceutical composition, comprising a nucleic acid or vector of as described above or elsewhere herein, optionally further comprising one or more carriers, diluents, excipients, or other additives.

Also provided is a host cell transformed with the nucleic acid molecule or cDNA molecules and/or the vectors disclosed herein. The disclosure also provides host cells transformed with the disclosed nucleic acid molecule or molecules operably linked to a control sequence and optionally inserted into a vector.

In additional embodiments, the disclosure provides a method of making the polypeptides provided herein comprising culturing a transformed host cell herein under suitable conditions for producing the polypeptide. The disclosure optionally provides isolating the polypeptide secreted from the host cell. The disclosure also optionally provides the polypeptide produced using this method and pharmaceutical compositions comprising the the polypeptide and a pharmaceutically acceptable carrier.

The choice of expression control sequence and expression vector will depend upon the choice of host. A wide variety of expression host/vector combinations can be employed (see also below for additional examples). Useful expression vectors for eukaryotic hosts, include, for example, vectors comprising expression control sequences from SV40, bovine papilloma virus, adenovirus and cytomegalovirus.

Useful expression vectors for bacterial hosts include known bacterial plasmids, such as plasmids from *E. coli*, including pCR1, pBR322, pMB9 and their derivatives, and also wider host range plasmids, such as M13 and filamentous single-stranded DNA phages.

A host cell may be a cell or a population of cells harboring or capable of harboring a recombinant nucleic acid. Host cells can be prokaryotic (e.g., *E. coli*), or eukaryotic. Prokaryotes include gram negative or gram positive organisms, for example *E. coli* or bacilli. The host cells can be fungal cells including yeast such as *Saccharomyces cerevisiae, Pichia pastoris*, or *Schizosaccharomyces pombe*. The host cells also be any of various animal cells, such as insect cells (e.g., Sf-9) or established cell lines of mammalian origin. Examples of suitable mammalian host cell lines include HEK-293, HEK293F, and HEK-293T, the COS-7 lines of monkey kidney cells, described by Gluzman (Cell 23:175 (1981)), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins Insect cells are reviewed by Luckow and Summers, *BioTechnology* 6:47 (1988). Cell-free translation systems could also be employed. In preferred embodiments, the host cell is *Pichia pastoris*.

Delivery of Nucleic Acid Molecules, Vectors and Hosts

In some embodiments, the nucleic acid molecules, the vectors, and host cells are provided in pharmaceutical compositions. In some embodiments, a component of pharmaceutical compositions aid delivery of nucleic acid into the intended recipient.

In some embodiments, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject.

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO89/02,468, WO89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 93/1230; WO 93/0218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

Methods of Producing a Polypeptide

In some embodiments, vectors comprising nucleic acids encoding the polypeptide (e.g., NP-011) may be transfected into host cells. As disclosed herein, the host cells may be cultured in a culture medium to produce the polypeptide. In some embodiments, the polypeptide is secreted into the medium. The polypeptide may be isolated from the medium using any suitable technique.

The polypeptides of the present invention (e.g., NP-011) produced by a transformed host cell can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. The polypeptide can also be physically characterized using such techniques as proteolysis, nuclear magnetic resonance and x-ray crystallography.

For example, supernatants from systems that secrete the polypeptides into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation or anion exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify the polypeptide.

The polypeptide produced in cell culture can be isolated, for example, by initial extraction from cell pellets, followed by one or more concentration, salting-out, aqueous ion exchange or size exclusion chromatography steps. High performance liquid chromatography (HPLC) can be employed for final purification steps. Cells employed in expression of a recombinant protein can be disrupted by any convenient method, including freeze-thaw cycling, sonication, mechanical disruption, or use of cell lysing agents.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Pharmaceutical Composition

In another aspect, the present invention provides pharmaceutically acceptable compositions which comprise a therapeutically-effective amount of the polypeptide disclosed herein formulated together with one or more pharmaceutically acceptable carriers (additives) and/or diluents. The pharmaceutical compositions of the present invention may be specially formulated for storage and use by combining a purified agent of the present invention encompassed by the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22.sup.nd Edition, 2012, Pharmaceutical Press, London). Formulations to be used for in vivo administration must be sterile. This is readily accomplished by filtration through sterile filtration membranes.

Examples of pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Pharmaceutically acceptable salts may be part of the pharmaceutical composition comprising the polypeptide of present invention. The salts may be relatively non-toxic, inorganic and organic acid addition to the formulation. The salts may be added to the polypeptide at any stage of the purification (including after purification). Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

Wetting agents, emulsifiers and lubricants, such as sodium lauryl sulfate and magnesium stearate, as well as release agents, preservatives and antioxidants can also be present in the compositions. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of this invention suitable for parenteral administration may comprise one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In certain embodiments, pharmaceutical formulations include polypeptide complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the polypeptide of present invention can be produced. Suitable examples of sustained-release preparations include semi-permeable matrices of solid hydrophobic polymers containing the polypeptide, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), sucrose acetate isobutyrate, and poly-D-(-)-3-hydroxybutyric acid.

The compositions described herein may be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the compositions can be suitably administered by pulse infusion.

In some embodiments, the polypeptides of present invention can be conjugated or modified according to well-known pharmacological methods in the art (e.g., pegylation, glycosylation, oligomerization, etc.) in order to further enhance desirable biological activities, such as increased bioavailability and decreased proteolytic degradation.

In some embodiments, the polypeptide is lyophilized and/or stored in a lyophilized form. In some embodiments, a formulation comprising the polypeptide described herein is lyophilized.

Kits

A "kit" is any manufacture (e.g. a package or container) comprising at least one composition, e.g. a polypeptide, of the present invention. The kit may also comprise additional diluents. The kit may comprise one or more agents necessary to resuspend the lyophilized composition and/or a filtration unit to remove aggregates. The kit may be promoted, distributed, or sold as a unit for performing the methods of the present invention. The kit may comprise one or more reagents necessary to express a composition useful in the methods of the present invention. Reagents in the kit may be provided in individual containers or as mixtures of two or more reagents in a single container. In addition, instructional materials which describe the use of the compositions within the kit may be included.

Sequences

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches. The comparison of sequences and determination of percent homology between two sequences can be accomplished using a mathematical algorithm.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a polypeptide has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a polypeptide described herein.

Nucleic acid variants may contain alterations in the coding regions, non-coding regions, or both. In some embodiments, the nucleic acid variants contain alterations that produce silent substitutions, additions, or deletions, but do not alter the properties or activities of the encoded polypeptide. In some embodiments, the nucleic acid variants are produced by silent substitutions due to the degeneracy of the genetic code. Nucleic acid variants can be produced for a variety of reasons, e.g., to optimize codon expression for a particular host (change codons in the human mRNA to those preferred by a bacterial host such as E. coli). Vectors and cells comprising the nucleic acids described herein are also provided.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

Non-conservative substitutions include those in which (a) a residue having an electropositive side chain (e.g., Arg, His, or Lys) is substituted for, or by, an electronegative residue (e.g., Glu or Asp), (b) a hydrophilic residue (e.g., Ser or Thr) is substituted for, or by, a hydrophobic residue (e.g., Ala, Leu, Ile, Phe, or Val), (c) a Cys or Pro is substituted for, or by, any other residue, or (d) a residue having a bulky hydrophobic or aromatic side chain (e.g., Val, His, Ile, or Trp) is substituted for, or by, one having a smaller side chain (e.g., Ala or Ser) or no side chain (e.g., Gly).

Other substitutions can be readily identified. For example, for the amino acid alanine, a substitution can be taken from any one of D-Ala, Gly, beta-Ala, L-Cys and D-Cys. For lysine, a replacement can be any one of D-Lys, Arg, D-Arg, homo-Arg, Met, D-Met, ornithine, or D-ornithine. Generally, substitutions in functionally important regions that can be expected to induce changes in the properties of isolated polypeptides are those in which (a) a polar residue (e.g., Ser or Thr) is substituted for (or by) a hydrophobic residue (e.g., Leu, Ile, Phe, or Ala); (b) a Cys residue is substituted for (or by) any other residue; (c) a residue having an electropositive side chain (e.g., Lys, Arg, or His), is substituted for (or by) a residue having an electronegative side chain (e.g., Glu or Asp); or (d) a residue having a bulky side chain (e.g., Phe) is substituted for (or by) one not having such a side chain (e.g., Gly). The likelihood that one of the foregoing non-conservative substitutions can alter functional properties of the protein is also correlated to the position of the substitution with respect to functionally important regions of the protein: some non-conservative substitutions can accordingly have little or no effect on biological properties.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |

GENETIC CODE

| | |
|---|---|
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a polypeptide of the invention (or any portion thereof) can be used to derive the fusion protein or polypeptide amino acid sequence, using the genetic code to translate the DNA or RNA into an amino acid sequence. Likewise, for a polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for nucleic acid and polypeptide molecules useful in the present invention are well known in the art and readily available on publicly available databases, such as the National Center for Biotechnology Information (NCBI). For example, exemplary nucleic acid and amino acid sequences derived from publicly available sequence databases are provided in Table 1 below.

TABLE 1

```
SEQ ID NO: 1 Human milk fat globule-EGF factor 8 protein (MFGE8),
transcript variant 2, cDNA (NM_001114614.3, CDS from 61 to 1068)
   1 agaaccccgc ggggtctgag cagcccagcg tgcccattcc agcgcccgcg tccccgcagc
  61 atgccgcgcc cccgcctgct ggccgcgctg tgcggcgcgc tgctctgcgc ccccagcctc
 121 ctcgtcgccc tggatatctg ttccaaaaac ccctgccaca acggtggttt atgcgaggag
 181 atttcccaag aagtgcgagg agatgtcttc ccctcgtaca cctgcacgtg ccttaagggc
 241 tacgcgggca accactgtga gacgaaatgt gtcgagccac tgggcctgga gaatgggaac
 301 attgccaact cacagatcgc cgcctcgtct gtgcgtgtga ccttcttggg tttgcagcat
 361 tgggtcccgg agctggcccg cctgaaccgc gcaggcatgg tcaatgcctg gacacccagc
 421 agcaatgacg ataaccctg gatccaggtg aacctgctgc ggaggatgtg ggtaacaggt
 481 gtggtgacgc agggtgccag ccgcttggcc agtcatgagt acctgaaggc cttcaaggtg
 541 gcctacagcc ttaatggaca cgaattcgat ttcatccatg atgttaataa aaaacacaag
 601 gagtttgtgg gtaactggaa caaaaacgcg gtgcatgtca acctgtttga gaccctgtg
 661 gaggctcagt acgtgagatt gtacccacg agctgccaca cggcctgcac tctgcgcttt
 721 gagctactgg gctgtgagct gaacggatgc gccaatcccc tgggcctgaa gaataacagc
 781 atccctgaca agcagatcac ggcctccagc agctacaaga cctgggggctt gcatctcttc
 841 agctggaacc cctcctatgc acggctggac aagcagggca acttcaacgc ctgggttgcg
 901 gggagctacg gtaacgatca gtggctgcag atcttccctg gcaactggga caaccactcc
 961 cacaagaaga acttgtttga gacgcccatc ctggctcgct atgtgcgcat cctgcctgta
1021 gcctggcaca accgcatcgc cctgcgcctg gagctgctgg gctgttagtg gccacctgcc
1081 accccaggt cttcctgctt tccatgggcc cgctgcctct tggcttctca gcccctttaa
1141 atcaccatag ggctgggac tggggaaggg gagggtgttc agaggcagca ccaccacaca
1201 gtcaccctc cctccctctt tccaccctc cacctctcac gggcctgcc ccagcccta
1261 agcccgtcc cctaacccc agtcctcact gtcctgtttt cttaggcact gagggatctg
1321 agtaggtctg ggatggacag gaaagggcaa agtagggcgt gtggtttccc tgcccctgtc
1381 cggaccgccg atcccaggtg cgtgtgtctc tgtctctcct agccctctc tcacacatca
1441 cattcccatg gtggcctcaa gaaaggcccg gaagcgccag gctggagata acagcctctt
1501 gcccgtcggc cctgcgtcgg ccctggggta ccatgtggcc acaactgctg tggccccctg
1561 tccccaagac acttcccctt gtctccctgg ttgcctctct tgccccttgt cctgaagccc
1621 agcgacacag aaggggtgg ggcgggtcta tggggagaaa gggagcgagg tcagaggagg
1681 gcatgggttg gcagggtggg cgttttgggc cctctatgct ggcttttcac cccagaggac
1741 acaggcagct tccaaaatat atttatcttc ttcacgggaa SEQ ID NO: 2 Human lactadherin isoform B (NP_001108086.1)
   1 mprprllaal cgallcapsl lvaldicskn pchngglcee isqevrgdvf psytctclkg
  61 yagnhcetkc veplglengn iansqiaass vrvtflglqh wvpelarlnr agmvnawtps
 121 snddnpwiqv nllrrmwvtg vvtqgasrla sheylkafkv ayslnghefd fihdvnkkhk
 181 efvgnwnkna vhvnlfetpv eagyvrlypt schtactlrf ellgcelngc anplglknns
 241 ipdkqitass syktwglhlf swnpsyarld kqgnfnawva gsygndqwlq ifpgnwdnhs
 301 hkknlfetpi laryvrilpv awhnrialrl ellgc
```

TABLE 1-continued

```
SEQ ID NO: 3 Human milk fat globule-EGF factor 8 protein (MFGE8),
transcript variant 4, cDNA (NM_001310319.2, CDS from 61 to 1092)
     1 agaaccccgc ggggtctgag cagcccagcg tgcccattcc agcgcccgcg tccccgcagc
    61 atgccgcgcc cccgcctgct ggccgcgctg tgcggcgcgc tgctctgcgc ccccagcctc
   121 ctcgtcgccc tggaatgtgt cgagccactg ggcctggaga atgggaacat tgccaactca
   181 cagatcgccg cctcgtctgt gcgtgtgacc ttcttgggtt tgcagcattg ggtcccggag
   241 ctggcccgcc tgaaccgcgc aggcatggtc aatgcctgga cacccagcag caatgacgat
   301 aaccctgga tccaggtgaa cctgctgcgg aggatgtggg taacaggtgt ggtgacgcag
   361 ggtgccagcc gcttggccag tcatgagtac ctgaaggcct tcaaggtggc ctacagcctt
   421 aatggacacg aattcgattt catccatgat gttaataaaa aacacaagga gtttgtgggt
   481 aactggaaca aaaacgcggt gcatgtcaac ctgtttgaga ccccgtgtgga ggctcagtac
   541 gtgagattgt accccacgag ctgccacacg gcctgcactc tgcgctttga gctactgggc
   601 tgtgagctga acggatgcgc caatcccctg ggctgaaga ataacagcat ccctgacaag
   661 cagatcacgg cctccagcag ctacaagacc tggggcttgc atctcttcag ctggaacccc
   721 tcctatgcac ggctggacaa gcagggcaac ttcaacgcct gggttgcggg gagctacggt
   781 aacgatcagt ggctgcaggt ggacctgggc tcctcgaagg aggtgacagg catcatcacc
   841 caggggggcc gtaactttgg ctctgtccag tttgtggcat cctacaaggt tgcctacagt
   901 aatgacagtg cgaactggac tgagtaccag gaccccagga ctggcagcag taagatcttc
   961 cctggcaact gggacaacca ctcccacaag aagaacttgt ttgagacgcc catcctggct
  1021 cgctatgtgc gcatcctgcc tgtagcctgg cacaaccgca tcgccctgcg cctggagctg
  1081 ctgggctgtt agtggccacc tgccacccc aggtcttcct gctttccatg ggcccgctgc
  1141 ctcttggctt ctcagccct ttaaatcacc ataggcggg ggactggggga aggggagggt
  1201 gttcagaggc agcaccacca cacagtcacc cctccctccc tctttccac cctccacctc
  1261 tcacgggccc tgccccagcc cctaagcccc gtccctaac ccccagtcct cactgtcctg
  1321 ttttcttagg cactgaggga tctgagtagg tctgggatgg acaggaaagg gcaaagtagg
  1381 gcgtgtggtt tccctgcccc tgtccggacc gccgatccca ggtgcgtgtg tctctgtctc
  1441 tcctagcccc tctctcacac atcacattcc catggtggcc tcaagaaagg cccggaagcg
  1501 ccaggctgga gataacagcc tcttgcccgt cggccctgcg tcggccctgg gtaccatgt
  1561 ggccacaact gctgtggccc cctgtcccca agacacttcc ccttgtctcc ctggttgcct
  1621 ctcttgcccc ttgtcctgaa gcccagcgac acagaaggggg gtggggcggg tctatgggga
  1681 gaaagggagc gaggtcagag gagggcatgg gttggcaggg tgggcgtttg gggccctcta
  1741 tgctggcttt tcaccccaga ggacacaggc agcttccaaa atatattttat cttcttcacg
  1801 ggaa SEQ ID NO: 4 Human lactadherin isoform D (NP_001297248.1)
     1 mprprllaal cgallcapsl lvalecvepl glengnians qiaasssvrvt flglqhwvpe
    61 larlnragmv nawtpssndd npwiqvnllr rmwvtgvvtq gasrlashey lkafkvaysl
   121 nghefdfihd vnkkhkefvg nwnknavhvn lfetpveaqy vrlyptscht actlrfellg
   181 celngcanpl glkknnsipdk qitasssykt wglhlfswnp syarldkqgn fnawvagsyg
   241 ndqwlqvdlg sskevtgiit qgarnfgsvq fvasykvays ndsanwteyq dprtgsskif
   301 pgnwdnhshk knlfetpila ryvrilpvaw hnrialrlel lgc SEQ ID NO: 5 Human milk fat globule-EGF factor 8 protein (MFGE8),
transcript variant 3, cDNA (NM_001310320.2, CDS from 138 to 186)
     1 agaaccccgc ggggtctgag cagcccagcg tgcccattcc agcgcccgcg tccccgcagc
    61 atgccgcgcc cccgcctgct ggccgcgctg tgcggcgcgc tgctctgcgc ccccagcctc
   121 ctcgtcgccc tggggtgatg tggccttttc cagaaggagg aaacaccata cctatcttac
   181 acacagatat ctgttccaaa aaccccgtcc acaacggtgg tttatgcgag gagatttccc
   241 aagaagtgcg aggagatgtc ttccctcgt cacctgcac gtgccttaag ggctacgcgg
   301 gcaaccactg tgagacgaaa tgtgtcgagc cactgggcct ggagaatggg aacattgcca
   361 actcacagat cgccgcctcg tctgtgcgtg tgaccttctt gggtttgcag cattgggtcc
   421 cggagctggc ccgcctgaac cgcgcaggca tggtcaatgc ctggacaccc agcagcaatg
   481 acgataaccc ctggatccag gtgaacctgc tgcggaggat gtgggtaaca ggtgtggtga
   541 cgcagggtgc cagccgcttg gccagtcatg agtacctgaa ggccttcaag gtggcctaca
   601 gccttaatgg acacgaattc gatttcatcc atgatgttaa taaaaaacac aaggagtttg
   661 tgggtaactg gaacaaaaac gcggtgcatg tcaacctgtt tgagaccct gtgaggctc
   721 agtacgtgag attgtacccc acgagctgcc acacgcctg cactctgcgc tttgagctac
   781 tgggctgtga gctgaacgga tgcgccaatc cctgggcct gaagaataac agcatccctg
   841 acaagcagat cacggcctcc agcagctaca agacctgggg cttgcatctc ttcagctgga
   901 accctccta tgcacggctg gacaagcagg gcaacttcaa cgcctgggtt gcggggagct
   961 acggtaacga tcagtggctg caggtggacc tgggctcctc gaaggaggtg acaggcatca
  1021 tcacccaggg ggcccgtaac tttggctctg tccagtttgt ggcatcctac aaggttgcct
  1081 acagtaatga cagtgcgaac tggactgagt accaggaccc caggactggc agcagtaaga
  1141 tcttccctgg caactgggac aaccactccc acaagaagaa cttgtttgag acgcccatcc
  1201 tggctcgcta tgtgcgcatc ctgcctgtag cctggcacaa ccgcatcgcc ctgcgcctgg
  1261 agctgctggg ctgttagtgg ccacctgcca ccccaggtc ttcctgcttt ccatgggccc
  1321 gctgcctctt ggcttctcag ccctttaaa tcaccatagg gctgggact ggggaagggg
  1381 agggtgttca gaggcagcac caccacacag tcacccctcc ctccctcttt cccaccctcc
  1441 acctctcacg ggccctgccc cagccctaa gccccgtccc ctaaccccca gtcctcactg
  1501 tcctgttttc ttaggcactg agggatctga gtaggtctgg gatgacagg aaagggcaaa
  1561 gtagggcgtg tggtttccct gcccctgtcc ggaccgccga tcccaggtgc gtgtgtctct
  1621 gtctctccta gcccctctct cacacatcac attcccatgg tggcctcaag aaaggcccgg
  1681 aagcgccagg ctggagataa cagcctcttg cccgtcggcc ctgcgtcggc cctggggtac
  1741 catgtggcca caactgctgt ggccccctgt ccccaagaca cttcccttg tctccctggt
  1801 tgcctctctt gccccttgtc ctgaagccca gcgacacaga agggggtggg gcgggtctat
  1861 ggggagaaag ggagcgaggt cagaggaggg catgggttgg cagggtgggc gtttgggggcc
  1921 ctctatgctg gcttttcacc ccagaggaca caggcagctt ccaaaatata tttatcttct
  1981 tcacgggaa
```

TABLE 1-continued

SEQ ID NO: 6 Human lactadherin isoform C (NP_001297249.1)
```
  1 mwpfpeggnt ipilhtdics knpchngglc eeisqevrgd vfpsytctcl kgyagnhcet
 61 kcveplglen gniansqiaa ssvrvtflgl qhwypelarl nragmvnawt pssnddnpwi
121 qvnllrrmwv tgvvtqgasr lasheylkaf kvayslnghe fdfihdvnkk hkefvgnwnk
181 navhvnlfet pveagyvrly ptschtactl rfellgceln gcanplglkn nsipdkqita
241 sssyktwglh lfswnpsyar ldkqgnfnaw vagsygndqw lqvdlgssked vtgiitqgar
301 nfgsvqfvas ykvaysndsa nwteyqdprt gsskifpgnw dnhshkknlf etpilaryvr
361 ilpvawhnri alrlellgc
```

SEQ ID NO: 7 Human milk-fat globule-EGF factor 8 protein (MFGE8),
transcript variant 5, cDNA (NM_001310321.2, CDS from 1005 to 1832)
```
   1 acctccactg ttgacaaact tagacaaagc cccggggacc gggctgggca gaggggcggc
  61 ttcttccgct gcgccctggc gggacagggg gatgcggccc tgctgtctct gcgctggggc
 121 ttttgggctg ggactcggga catcgggtga cagccctgcc gcccccaggg atgcggctta
 181 cagataatga caaaggaatc cgctgtgtcg ggcctctctt ttccctggtg aaaaatgagg
 241 ccagggaact gcgtttgact ttcgaacccc ttccacctgg agattctag gactctagta
 301 tggataagtc ttgtctggat aactttgtcc tggccatctc cctgccaatc ccagttggct
 361 ggacagttca ttggattttt gcgctcccaa ttgtccgtgc ctggtcacat aagggaaggg
 421 ccggggagtc ggtgcaatgg acgcaggccg taagtggggc ccggaggggg acccagaggc
 481 ttcgaggagc ttggaagagg gctgcctgct gatgggagtc tcctgactcc ctccctcccg
 541 cggccttggc cggctgctgt atcttcccg gtcctcctcc gcctcccagg aggcctccgg
 601 aggccagctg gccccttgc aggctggact gcggatgcc ccgtgccatt caccgtggag
 661 cgctgggagg gagtcaggc caggactctt taggtggccc ctccatcatt ttctcataga
 721 aatgggattg actgaagcaa gatatctgtt ccaaaaaccc ctgccacaac ggtggttttat
 781 gcgaggagat ttcccaagaa gtgcgaggag atgtcttccc ctcgtacacc tgcacgtgcc
 841 ttaagggcta cgcgggcaac cactgtgaga cgaaatgtgt cgaccactg ggcctggaga
 901 atgggaacat tgccaactca cagatcgccg cctcgtctgt gcgtgtgacc ttcttgggtt
 961 tgcagcattg gtcccggag ctggcccgcc tgaaccgcgc aggcatggtc aatgcctgga
1021 cacccagcag caatgacgat aaccccctgga tccaggtgaa cctgctgcgg aggatgtggg
1081 taacaggtgt ggtgacgcag ggtgccagcc gcttggccag tcatgagtac ctgaaggcct
1141 tcaaggtggc ctacagcctt aatggacacg aattcgattt catccatgat gttaataaaa
1201 aacacaagga gtttgtgggt aactggaaca aaaacgcggt gcatgtcaac ctgtttgaga
1261 cccctgtgga ggctcagtac gtgagattgt accccacgag ctgccacacg gcctgcactc
1321 tgcgctttga gctactgggc tgtgagctga acggatgcgc caatccccg ggcctgaaga
1381 ataacagcat ccctgacaag cagatcacgg cctccagcag ctacaagacc tggggcttgc
1441 atctcttcag ctggaacccc tcctatgcac ggctgacaa gcagggcaac ttcaacgcct
1501 gggttgcggg gagctacggt aacgatcagt ggctgcaggt ggacctgggc tcctcgaagg
1561 aggtgacagg catcatcacc caggggggcc gtaacttgg ctctgtccag tttgtggcat
1621 cctacaaggt tgcctacagt aatgacagtg cgaactggac tgagtaccag gaccccagga
1681 ctggcagcag taagatcttc cctggcaact gggacaacca ctcccacaag aagaacttgt
1741 ttgagacgcc catcctggct cgctatgtgc gcatcctgcc tgtagcctgg cacaaccgca
1801 tcgccctgcg cctggagctg ctgggctgtt agtggccagc tgccaccccc aggtcttcct
1861 gctttccatg gcccgctgc ctcttggctt tcagcccct ttaaatacc atagggctgg
1921 ggactgggga aggggaggt gttcagagc agcaccacca cacagtcacc cctccctccc
1981 tctttcccac cctccacctc tcacgggccc tgcccagcc cctaagcccc gtccctaac
2041 cccagtcct cactgtcctg ttttcttagg cactgaggga tctgagtagg tctgaggatgg
2101 acaggaaagg gcaaagtagg gcgtgtggtt tccctgcccc tgtccggacc gccgatccca
2161 ggtgcgtgtg tctctgtctc tcctagcccc tctctcacac atcacattcc catggtggcc
2221 tcaagaaagg cccggaagcg ccaggctgga gataacagcc tcttgccgt cggccctgcg
2281 tcggccctgg ggtaccatgt ggccacaact gctgtggccc cctgtcccca agacacttcc
2341 ccttgtctcc ctggttgcct ctcttgcccc ttgtcctgaa gcccagcgac acagaagggg
2401 gtggggcggg tctatgggga gaaagggagc gaggtcagag gagggcatgg gttggcaggg
2461 tgggcgtttg ggccctcta tgctggcttt tcaccccaga ggacacaggc agcttccaaa
2521 atatatttat cttcttcacg ggaa
```

SEQ ID NO: 8 Human lactadherin isoform E (NP_001297250.1)
```
  1 mvnawtpssn ddnpwiqvnl lrrmwvtgvv tqgasrlash eylkafkvay slnghefdfi
 61 hdvnkkhkef vgnwnknavh vnlfetpvea qyvrlyptsc htactlrfel lgcelngcan
121 plglknnsip dkqitasssy ktwglhlfsw npsyarldkq gnfnawvags ygndqwlqvd
181 lgsskevtgi itqgarnfgs vqfvasykva ysndsanwte yqdprtgssk ifpgnwdnhs
241 hkknifetpi laryvrilpv awhnrialrl ellgc
```

SEQ ID NO: 9 Human milk fat globule-EGF factor 8 protein (MFGE8),
transcript variant 1, cDNA (NM_005928.4, CDS from 61 to 1224)
```
   1 agaaccccgc ggggtctgag cagcccagcg tgcccattcc agcgcccgcg tccccgcagc
  61 atgccgcgcc cccgcctgct ggccgcgctg tgcggcgcgc tgctctgcgc cccagcctc
 121 ctcgtcgccc tggatatctg ttccaaaaac ccctgccaca acggtggttt atgcgaggag
 181 atttcccaag aagtgcgagg agatgtcttc ccctcgtaca cctgcacgtg ccttaagggc
 241 tacgcgggca accactgtga cgaaatgt gtcgagccac tgggcctgga gaatgggaac
 301 attgccaact cacagatcgc cgcctcgtct gtgcgtgtga ccttcttggg tttgcagcat
 361 tgggtcccgg agctggcccg cctgaaccgc gcaggcatgg tcaatgcctg gacacccagc
 421 agcaatgacg ataaccctg gatccaggtg aacctgctgc ggaggatgtg gtaacaggt
 481 gtggtgacgc agggtgccag ccgcttggcc agtcatgagt acctgaaggc cttcaaggtg
 541 gcctacagcc ttaatggaca cgaattcgat ttcatccatg atgttaataa aaaacacaag
 601 gagtttgtgg gtaactggaa caaaaacgcg gtgcatgtca acctgtttga gacccctgtg
 661 gaggctcagt acgtgagatt gtaccccacg agctgccaca cggcctgcac tctgcgcttt
 721 gagctactgg gctgtgagct gaacggatgc gccaatcccc tgggcctgaa gaataacagc
 781 atccctgaca gcagatcac ggcctccagc agctacaaga cctgggcttg catctcttc
 841 agctggaacc cctcctatgc acggctgac aagcagggca acttcaacgc ctggggttgcg
 901 gggagctacg gtaacgatca gtggctgcag gtggacctgg ctcctcgaa ggaggtgaca
```

TABLE 1-continued

```
 961 ggcatcatca cccagggggc ccgtaacttt ggctctgtcc agtttgtggc atcctacaag
1021 gttgcctaca gtaatgacag tgcgaactgg actgagtacc aggaccccag gactggcagc
1081 agtaagatct tccctggcaa ctgggacaac cactcccaca agaagaactt gtttgagacg
1141 cccatcctgg ctcgctatgt gcgcatcctg cctgtagcct ggcacaaccg catcgccctg
1201 cgcctggagc tgctgggctg ttagtggcca cctgccaccc ccaggtcttc ctgctttcca
1261 tgggcccgct gcctcttggc ttctcagccc cttaaatca ccatagggct ggggactggg
1321 gaaggggagg gtgttcagag gcagcaccac cacacagtca cccctccctc cctctttccc
1381 accctccacc tctcacgggc cctgccccag ccctaagcc ccgtcccta acccccagtc
1441 ctcactgtcc tgttttctta ggcactgagg gatctgagta ggtctgggat ggacaggaaa
1501 gggcaaagta gggcgtgtgg tttccctgcc cctgtccgga ccgccgatcc caggtgcgtg
1561 tgtctctgtc tctcctagcc cctctctcac acatcacatt cccatggtgg cctcaagaaa
1621 ggcccggaag cgccaggctg agataacag cctcttgccc gtcggccctg cgtcggccct
1681 ggggtaccat gtggccacaa ctgctgtggc cccctgtccc caagacactt cccccttgtct
1741 ccctggttgc ctctcttgcc ccttgtcctg aagcccagcg acacagaagg gggtggggcg
1801 ggtctatggg gagaaaggga gcgaggtcag aggagggcat gggttggcag ggtgggcgtt
1861 tggggccctc tatgctggct tttcacccca gaggacacag gcagcttcca aaatatattt
1921 atcttcttca cgggaa
```

SEQ ID NO: 10 Human lactadherin isoform A (NP_005919.2)

```
  1 mprprllaal cgallcapsl lvaldicskn pchngglcee isqevrgdvf psytctclkg
 61 yagnhcetkc veplglengn iansqiaass vrvtflglqh wypelarlnr agmvnawtps
121 snddnpwiqv nllrrmwvtg vvtqgasrla sheylkafkv ayslnghefd fihdvnkkhk
181 efvgnwnkna vhvnlfetpv eagyvrlypt schtactlrf ellgcelngc anplglknns
241 ipdkqitass syktwglhlf swnpsyarld kqgnfnawva gsygndqwlq vdlgssekvt
301 giitqgarnf gsvqfvasyk vaysndsanw teyqdprtgs skifpgnwdn hshkknlfet
361 pilaryvril pvawhnrial rlellgc
```

*The amino acid sequence (amino acids 24-225) that corresponds to NP-011(a) is underlined.

Amino acids 1-23 corresponds to the signal peptide.

SEQ ID NO: 11 Nucleic acid encoding human NP-011

```
  1 agaaccccgc ggggtctgag cagcccagcg tgcccattcc agcgcccgcg tccccgcagc
 61 atgccgcgcc cccgcctgct ggccgcgctg tgcggcgcgc tgctctgcgc cccccagcct
121 ctcgtcgccc tggatatctg ttccaaaaac ccctgccaca cggtggttt atgcgaggag
181 atttccccaag aagtgcgagg agatgtcttc ccctcgtaca cctgcacgtg ccttaagggc
241 tacgcgggca accactgtga gacgaaatgt gtcgagccac tgggcatgga gaatgggaac
301 attgccaact cacagatcgc cgcctcgtct gtgcgtgtga ccttcttggg tttgcagcat
361 tgggtcccgg agctggcccg cctgaaccgc gcaggcatgg tcaatgcctg gacaccccagc
421 agcaatgacg ataaccctg gatccaggtg aacctgctgc ggaggatgtg gtaacaggt
481 gtggtgacgc agggtgccag ccgcttggcc agtcatgagt acctgaaggc cttcaaggtg
541 gcctacagcc ttaatggaca cgaattcgat ttcatccatg atgttaataa aaaacacaag
601 gagtttgtgg gtaactggaa caaaaacgcg gtgcatgtca acctgtttga ccccctgtg
661 gaggctcagt acgtgagatt gtaccccacg agctgccaca cggcctgcac tctgcgcttt
721 gaactactgg gctgtgagct gaacggatgc gccaatcccc tgggcctgaa gaataacgac
781 atccctgaca gcagatcac ggcctccagc agctacaaga cctgggggctt gcatctcttc
841 agctggaacc cctcctatgc acggctggac aagcaggca acttcaacgc ctgggttgcg
901 gggagctacg gtaacgatca gtggctgcag gtggacctgg gctcctcgaa ggaggtgaca
961 ggcatcatca cccagggggc ccgtaacttt ggctctgtcc agtttgtggc atcctacaag
1021 gttgcctaca gtaatgacag tgcgaactgg actgagtacc aggaccccag gactggcagc
1081 agtaagatct tccctggcaa ctgggacaac cactcccaca agaagaactt gtttgagacg
1141 cccatcctgg ctcgctatgt gcgcatcctg cctgtagcct ggcacaaccg catcgccctg
1201 cgcctggagc tgctgggctg ttagtggcca cctgccaccc ccaggtcttc ctgctttcca
1261 tgggcccgct gcctcttggc ttctcagccc cttaaatca ccatagggct ggggactggg
1321 gaaggggagg gtgttcagag gcagcaccac cacacagtca cccctccctc cctctttccc
1381 accctccacc tctcacgggc cctgccccag ccctaagcc ccgtcccta acccccagtc
1441 ctcactgtcc tgttttctta ggcactgagg gatctgagta ggtctgggat ggacaggaaa
1501 gggcaaagta gggcgtgtgg tttccctgcc cctgtccgga ccgccgatcc caggtgcgtg
1561 tgtctctgtc tctcctagcc cctctctcac acatcacatt cccatggtgg cctcaagaaa
1621 ggcccggaag cgccaggctg agataacag cctcttgccc gtcggccctg cgtcggccct
1681 ggggtaccat gtggccacaa ctgctgtggc cccctgtccc caagacactt cccccttgtct
1741 ccctggttgc ctctcttgcc ccttgtcctg aagcccagcg acacagaagg gggtggggcg
1801 ggtctatggg gagaaaggga gcgaggtcag aggagggcat gggttggcag ggtgggcgtt
1861 tggggccctc tatgctggct tttcacccca gaggacacag gcagcttcca aaatatattt
1921 atcttcttca cgggaa
```

SEQ ID NO: 12 Human NP-011

```
  1 mprprllaal cgallcapsl lvaldicskn pchngglcee isqevrgdvf psytctclkg
 61 yagnhcetkc veplgmengn iansqiaass vrvtflglqh wypelarlnr agmvnawtps
121 snddnpwiqv nllrrmwvtg vvtqgasrla sheylkafkv ayslnghefd fihdvnkkhk
181 efvgnwnkna vhvnlfetpv eagyvrlypt schtactlrf ellgcelngc anplglknns
241 ipdkqitass syktwglhlf swnpsyarld kqgnfnawva gsygndqwlq vdlgssekvt
301 giitqgarnf gsvqfvasyk vaysndsanw teyqdprtgs skifpgnwdn hshkknlfet
361 pilaryvrll pvawhnrlal rlellgc
```

*The amino acid sequence (amino acids 24-225) that corresponds to NP-011 is underlined.

Amino acids 1-23 corresponds to the signal peptide.

SEQ ID NO: 13 Rat milk fat globule-EGF factor 8 protein (Mfge8),
transcript variant 1, cDNA (NM_001040186.2, CDS from 82 to 1533)
```
   1 attccctgt gagaggagcg gacgcaggaa ctctccggtc ccagcatcgg agcttgtgga
  61 ccatttcccg cgtcccgcag catgcagttc tcccgtgtgc tggccgcgct gtgcggtgtg
 121 ctgctctgcg cctccggcct cttcgctgcg tccggtgact tctgtgactc cagcctgtgc
 181 ctgaatggtg ggacctgctt gatgggccaa gacaatgaca tctactgcct ctgccctgaa
 241 ggcttcacag gccttgtgtg caacgagact gagaaaggac cgtgttccc aaacccttgc
 301 ttccacgatg ccaaatgcct ggtgactgag gacacacagc gaggggacat cttcactgag
 361 tacatctgcc agtgccctgt gggctactcg gcatccact gtgaactcga gaccacctcc
 421 tacctggatg agagtacct gtccagccca gccgtcccta ccacagccgt ccccaccaca
 481 gccatcccca ccacagccgt ccccaccaca gccgtcccca ccacagccgt ccccaccccg
 541 gccccaacc ccgatctttc caaccaccta gcctcccgct gttccacaaa gctgggcttg
 601 gaaggggcg ccattgccga ttcacagatt tctgcctcgt ctgtgtatat gggcttcatg
 661 ggcttgcagc gctggggccc ggagctggct cgcctgtatc gcacagggat tgtcaatgca
 721 tggacagcca gcagctatga tagcaagccc tggatccagg tggacttttct gcggaagatg
 781 cgggtatcag gtgtgatgac acagggtgcc agccgtgccg ggagggcgaa atacctgaag
 841 accttcaagg tggcttacag cctcgatgga cgcaggttcg agttcatcca ggatgaaagc
 901 ggaaccggag acaaggagtt tatgggtaac caggacaaca acagcctgaa gattaacatg
 961 ttcaacccca ctctggaggc acagtacata aggctgtacc ctgtctcgtc ccaccgcggc
1021 tgcaccctcc gcttcgagct cctgggctgc gagttgcatg gatgctcgtga gccgctggc
1081 ctgaagaata acacgattcc tgacagccaa ataacagcct ccagcagcta caagacgtgg
1141 aacctgcgtg cctttggctg gtaccccac ttgggcggc tggacaatca gggcaagatc
1201 aatgcctgga cagctcagag caacagtgcc aaggaatggc tgcaggttga cctgggcact
1261 cagaaaaaag tgacaggaat tatcacccag gggccgtg actttggcca catccagtat
1321 gtggcatcct ataaggtagc ccacagtgat gatggtgtc agtggaccgt atatgaggaa
1381 caaggaacca gcaaggtctt ccagggcaac ttggacaaca actcccacaa gaagaacatc
1441 tttgagaaac cttttcatggc tcgctatgtg cgtgtcctc cactgtcctg cataaccgt
1501 atccccctgc gcctggagct gctgggctgt tagtgcccag tccttccagc ccaagtgacg
1561 aggacggcca gaggctgagg ggcctcctgg ccctgcctcc caggccctgc tgccttctgt
1621 ggctgacacc ttctcaatcc tccctcttga ttgcactggg actacaggca ggaagggcaa
1681 gggggtttca gagttgcccc tcacccttcc cctcaccctg cagccccac aggcctcctg
1741 ctagccctt ctctcaggca ttctggggga gttggacagg tctgagatga atagagaaga
1801 agagtgaagt tggggtatgt gggctgctgt accaaccacc ccaagtccta aactttctcc
1861 aggggttgac tcaagactaa agggaacctc tggttgccca cccgtctctg cacaccgcac
1921 atccctccat gttccattcc tggaaggaga gcccacgtc cgcttgctgc cccttgggtc
1981 accagatcct gcctcttatc tcctgagacc cctcttgacc ctcgctctgg agcctcggtt
2041 gacaagagga ctgtcgggtc tggagagata gatgggctct gggtggttgg cgagcttggct
2101 atgggacctc tgctggcttg ctacccaagc taacaagcag attccaaaat acatttgtgc
2161 tctccactgg aaaaaaaaaa aaaaaaaa
```

SEQ ID NO: 14 Rat lactadherin isoform 1 (NP_001035276.1)
```
   1 mqfsrvlaal cgvllcasgl faasgdfcds slclnggtcl mgqdndiycl cpegftglvc
  61 netekgpcsp npcfhdakcl vtedtqrgdi fteyicqcpv gysgihcele ttsyldgeyl
 121 sspavpttav pttaipttav pttavpttav ptpapnpdls nhlasrcstk lgleggaiad
 181 sqisassvym gfmglqrwgp elarlyrtgi vnawtassyd skpwlqvdfl rkmrvsgvmt
 241 qgasragrae ylktfkvays ldgrrfefiq desgtgdkef mgnqdnnslk inmfnptlea
 301 qyirlypvsc hrgctlrfel lgcelhgcse plglknntip dsqitasssy ktwnlrafgw
 361 yphlgrldnq gkinawtaqs nsakewlqvd lgtqkkvtgi itqgardfgh iqyvasykva
 421 hsddgvqwtv yeeqgtskvf qgnldnnshk knifekpfma ryvrvlplsw hnritlrlel
 481 lgc
```

SEQ ID NO: 15 Rat milk fat globule-EGF factor 8 protein (Mfge8),
transcript variant 2, cDNA (NM_012811.3, CDS from 82 to 1365)
```
   1 attccctgt gagaggagcg gacgcaggaa ctctccggtc ccagcatcgg agcttgtgga
  61 ccatttcccg cgtcccgcag catgcagttc tcccgtgtgc tggccgcgct gtgcggtgtg
 121 ctgctctgcg cctccggcct cttcgctgcg tccggtgact tctgtgactc cagcctgtgc
 181 ctgaatggtg ggacctgctt gatgggccaa gacaatgaca tctactgcct ctgccctgaa
 241 ggcttcacag gccttgtgtg caacgagact gagaaaggac cgtgttccc aaacccttgc
 301 ttccacgatg ccaaatgcct ggtgactgag gacacacagc gaggggacat cttcactgag
 361 tacatctgcc agtgccctgt gggctactcg gcatccact gtgaactcgg ctgttccaca
 421 aagctgggct tggaagggg cgccattgcc gattcacaga tttctgcctc gtctgtgtat
 481 atgggcttca tgggcttgca gcgctggggc ccggagctgg ctcgcctgta tcgcacaggg
 541 attgtcaatg catggacagc cagcagctat gatagcaagc cctggatcca ggtggacttt
 601 ctgcggaaga tgcgggtatc aggtgtgatg acacagggtg ccagccgtgc cgggagggcg
 661 aatacctga gaccttcaa ggtggcttac agcctcgatg gacgcaggtt cgagttcatc
 721 caggatgaaa gcggaaccgg agacaaggag tttatgggta accaggacaa caactcccac
 781 aagattaaca tgttcaaccc cactctggag gcacagtaca taaggctgta ccctgtctcg
 841 tgccaccgcg gctgcaccct ccgcttcgag ctcctgggct gcgagttgca tggatgctct
 901 gagcccctgg gcctgaagaa taacacgatt cctgacagcc aaataacagc ctccagcagc
 961 tacaagacgt ggaacctgcg tgcctttggc tggtaccccc acttgggcgg ctggacaat
1021 cagggcaaga tcaatgcctg gacagctcag agcaacagtg ccaaggaatg gctgcaggtt
1081 gacctgggca ctcagaaaaa agtgacagga attatcaccc aggggccgtg actttggcc
1141 cacatccagt atgtggcatc ctataaggta gcccacagtg atgatggtgt gcagtggacc
1201 gtatatgagg aacaaggaac cagcaaggtc ttccagggca acttggacaa caactcccac
1261 aagaagaaca tctttgagaa acctttcatg gctcgctatg tgcgtgtcct tccactgtcc
1321 tggcataacc gtatcacccct gcgcctggag ctgctgggct gttagtgccc agtccttcca
1381 gcccaagtga cgaggacggc cagaggctga ggggcctcct ggccctgcct cccaggccct
1441 gctgccttct gtggctgaca ccttctcaat cctccctctt gattgcactg ggactacagg
1501 caggaagggc aagggggttt cagagttgcc cctcaccctt cccctcaccc tgcagccccc
```

TABLE 1-continued

```
1561 acaggcctcc tgctagcccc ttctctcagg cattctgggg gagttggaca ggtctgagat
1621 gaatagagaa gaagagtgaa gttggggtat gtgggctgct gtaccaacca ccccaagtcc
1681 taaactttct ccaggggttg actcaagact aaagggaacc tctggttgcc caccgtctc
1741 tgcacaccgc acatccctcc atgttccatt cctggaagga gaggcccacg tccgcttgct
1801 gccccttggg tcaccagatc ctgcctctta tctcctcttga ccctcgctct
1861 ggagcctcgg ttgacaagag gactgtcggg tctggagaga tagatgggct ctgggtggtt
1921 ggcgagctgg ctatgggacc tctgctggct tgctacccaa gctaacaagc agattccaaa
1981 atacatttgt gctctccact ggaaaaaaaa aaaaaaaaaa
```

SEQ ID NO: 16 Rat lactadherin isoform 2 (NP_036943.1)
```
  1 mqfsrvlaal cgvllcasgl faasgdfcds slclnggtcl mgqdndiycl cpegftglvc
 61 netekgpcsp npcfhdakcl vtedtqrgdi fteyicqcpv gysgihcelg cstklglegg
121 aiadsqisas svymgfmglq rwgpelarly rtgivnawta ssydskpwiq vdflrkmrvs
181 gvmtqgasra graeylktfk vaysldgrrf efiqdesgtg dkefmgnqdn nslkinmfnp
241 tleagyirly pvschrgctl rfellgcelh gcseplglkn ntipdsqita sssyktwnlr
301 afgwyphlgr ldnqgkinaw taqsnsakew lqvdlgtqkk vtgiitqgar dfghlqyvas
361 ykvahsddgv qwtvyeeqgt skvfqgnldn nshkknifek pfmaryvrvl plswhnritl
421 rlellgc
```

SEQ ID NO: 17 Mouse milk fat globule-EGF factor 8 protein (Mfge8),
transcript variant 2, cDNA (NM_001045489.1, CDS from 94 to 1374)
```
  1 ggcgcctgat ttattccgga gtgagaggag cggacgcagg aactctcgag tccagcatc
 61 agagcgcgtg gacctttcc cgcgtcccgc agcatgcagg tctcccgtgt gctggccgcg
121 ctgtgcggca tgctactctg cgcctctggc ctcttcgccg cgtctggtga cttctgtgac
181 tccagcctgt gcctgaacgg tggcacctgc ttgacgggcc aagacaatga catctactgc
241 ctctgccctg aaggcttcac aggccttgtg tgcaatgaga ctgagagagg accatgctcc
301 ccaaacccctt gctacaatga tgccaaatgt ctggtgactt tggacacaca gcgtggggac
361 atcttcaccg aatacatctg ccagtgccct gtgggctact cgggcatcca ctgtgaaacc
421 ggttgttcta cacagctggg catggaaggg ggcgccattg ctgattccgc
481 tcgtctgtgt atatgggttt catgggcttg cagcgctggg gcccggagct ggctcgtctg
541 taccgcacag ggatcgtcaa tgcctggaca gccagcaact atgatagcaa gccctggatc
601 caggtgaacc ttctgcgaaa gatgcgggta tcaggtgtga tgacgcaggg tgccagccgt
661 gccgggaggg cggagtacct gaagaccttc aaggtggctt acagcctcga cggacgcaag
721 tttgagttca tccaggatga aagcggtgga gacaaggagt ttttgggtaa cctggacaac
781 aacagcctga aggttaacat gttcaacccg actctggagg cacagtacat aaagctgtac
841 cctgtttcgt gccaccgcgg ctgcacccte cgcttcgagc tcctgggctg tgagttgcac
901 ggatgttctg agcccctggg cctgaagaat aacacaattc tgacagcca gatgtcagcc
961 tccagcagct acaagacatg gaacctgcgt gcttttggct ggtaccccca cttgggaagg
1021 ctggataatc agggcaagat caatgcctgg acggctcaga gcaacagtgc caaggaatgg
1081 ctgcaggttg acctgggcac tcagaggcaa gtgacaggaa tcatcaccca gggggcccgt
1141 gactttggcc acatccagta tgtggcgtcc tacaaggtag cccacagtga tgatggtgtg
1201 cagtggactg tatatgagga gcaaggaagc agcaaggtct tccagggcaa cttggacaac
1261 aactcccaca gaagaacat cttcgagaaa cccttcatgg ctcgctacgt gcgtgtcctt
1321 ccagtgtcct ggcataaccg catcaccctg cgcctggagc tgctgggctg ttaatgctca
1381 gtcctgccag cccaaacgat gaggatggcc agaggctgag gggcctcctg gccctgcctc
1441 ccaggccctg ctgccttctg tggctgacga ccttcttggc cttcccttct gattgtactg
1501 gggctggagg caggaagggc caggggattt cagagttgcc cttcacccttt tccctcaccc
1561 tgcagccccc acaggcctcc tgctagcccc cttctctcag gcattctggg ggagttggac
1621 aggtctgaga tgaatagaga agaagagtga agttggggta tgtgggctat ctgtaccaac
1681 caccccaagt cctaaacttc ctgccagggc ttgactcagg actgaaggga gccccctgact
1741 gcccatccct ctctgcacac cacacattcc tccatgttcc attccgggaa ggagaggccc
1801 acgtccgctt gctgtccctt gggtcaccag gtcctgcctc ttatctcctg agacgcctct
1861 tgacccttgc actggagcct cagttgacaa ggagactggc gggtctggag aggtcggtgg
1921 ctctgggtgg ttgacaggtt ggctgtggga cctctgctgg cttgctaccc aagttaacaa
1981 gcagattcca aaatacattc gtgttctcca ctggaaaaaa aaaaaaaaa aa
```

SEQ ID NO: 18 Mouse lactadherin isoform 2 (NP_001038954.1)
```
  1 mqvsrvlaal cgmllcasgl faasgdfcds slclnggtcl tgqdndiycl cpegftglvc
 61 netergpcsp npcyndakcl vtldtqrgdi fteyicqcpv gysgihcetg cstqlgmegg
121 aiadsqisas svymgfmglq rwgpelarly rtgivnawta snydskpwiq vnllrkmrvs
181 gvmtqgasra graeylktfk vaysldgrkf efiqdesggd keflgnldnn slkvnmfnpt
241 leagyiklyp vschrgctlr fellgcelhg cseplglknn tipdsqmsas ssyktwnlra
301 fgwyphlgrl dnqgkinawt aqsnsakewl qvdlgtqrqv tgiitqgard fghiqyvasy
361 kvahsddgvq wtvyeeqgss kvfqgnldnn shkknifekp fmaryvrvlp vswhnritlr
421 lellgc
```

SEQ ID NO: 19 Mouse milk fat globule-EGF factor 8 protein (Mfge8),
transcript variant 1, cDNA (NM 008594.2, CDS from 94 to 1485)
```
  1 ggcgcctgat ttattccgga gtgagaggag cggacgcagg aactctcgag tccagcatc
 61 agagcgcgtg gacctttcc cgcgtcccgc agcatgcagg tctcccgtgt gctggccgcg
121 ctgtgcggca tgctactctg cgcctctggc ctcttcgccg cgtctggtga cttctgtgac
181 tccagcctgt gcctgaacgg tggcacctgc ttgacgggcc aagacaatga catctactgc
241 ctctgccctg aaggcttcac aggccttgtg tgcaatgaga ctgagagagg accatgctcc
301 ccaaacccctt gctacaatga tgccaaatgt ctggtgactt tggacacaca gcgtggggac
361 atcttcaccg aatacatctg ccagtgccct gtgggctact cgggcatcca ctgtgaaacc
421 gagaccaact actacaaacct ggatggagaa tacatgttca ccacagccgt cccaatact
481 gccgtcccca ccccggcccc caccccgat ctttccaaca acctagcctc ccgttgttct
541 acacagctgg gcatggaagg gggcgccatt gctgattcac agatttccgc ctcgtctgtg
601 tatatgggtt tcatgggctt gcagcgctgg ggcccggagc tggctcgtct gtaccgcaca
661 gggatcgtca atgcctggac agccagcaac tatgatagca gccctggat ccaggtgaac
```

TABLE 1-continued

```
 721 cttctgcgga agatgcgggt atcaggtgtg atgacgcagg gtgccagccg tgccgggagg
 781 gcggagtacc tgaagacctt caaggtggct tacagcctcg acggacgcaa gtttgagttc
 841 atccaggatg aaagcggtgg agacaaggag ttttttgggta acctggacaa caacagcctg
 901 aaggttaaca tgttcaaccc gactctggag gcacagtaca taaagctgta ccctgtttcg
 961 tgccaccgcg gctgcaccct ccgcttcgag ctcctgggct gtgagttgca cggatgttct
1021 gagccctgg gcctgaagaa taacacaatt cctgacagcc agatgtcagc ctccagcagc
1081 tacaagacat ggaacctgcg tgcttttggc tggtaccccc acttgggaag gctggataat
1141 cagggcaaga tcaatgcctg gacggctcag agcaacagtg ccaaggaatg gctgcaggtt
1201 gacctgggca ctcagaggca agtgacagga atcatcaccc aggggcccg tgactttggc
1261 cacatccagt atgtggcgtc ctacaaggta gcccacagtg atgatggtgt gcagtggact
1321 gtatatgagg agcaaggaag cagcaaggtc ttccagggca acttggacaa caactcccac
1381 aagaagaaca tcttcgagaa accccttcatg gctcgctacg tgcgtgtcct tccagtgtcc
1441 tggcataacc gcatcaccct gcgcctggag ctgctgggct gttaatgctc agtcctgcca
1501 gcccaaacga tgaggatggc cagaggctga ggggcctcct ggccctgcct cccaggccct
1561 gctgccttct gtggctgacg accttcttgg ccttcccttc tgattgtact ggggctggag
1621 gcaggaaggg ccaggggatt tcagagttgc ccttcaccct ttccctcacc ctgcagcccc
1681 cacaggcctc ctgctagccc ccttctctca ggcattctgg gggagttgga caggtctgag
1741 atgaatagag aagaagagtg aagttggggt atgtgggcta tctgtaccaa ccaccccaag
1801 tcctaaactt cctgccaggg cttgactcag gactgaaggg agccctgac tgcccatccc
1861 tctctgcaca ccacacattc ctccatgttc cattccggga aggagaggcc cacgtccgct
1921 tgctgtccct tgggtcacca ggtcctgcct cttatctcct gagacgcctc ttgacccttg
1981 cactggagcc tcagttgaca aggagactgg cgggtctgga gaggtcggtg gctctgggtg
2041 gttgacaggt tggctgtggg acctctgctg gcttgctacc caagttaaca agcagattcc
2101 aaaatacatt cgtgttctcc actggaaaaa aaaaaaaaaa aaa SEQ ID NO: 20 Mouse lactadherin isoform 1 (NP_032620.2)
    1 mqvsrvlaal cgmllcasgl faasgdfcds slclnggtcl tgqdndiycl cpegftglvc
   61 netergpcsp npcyndakcl vtldtqrgdi fteyicqcpv gysgihcete tnyynldgey
  121 mfttavpnta vptpaptpdl snnlasrcst qlgmeggaia dsqisassvy mgfmglqrwg
  181 pelarlyrtg ivnawtasny dskpwiqvnl lrkmrvsgvm tqgasragra eylktfkvay
  241 sldgrkfefi qdesggdkef lgnldnnslk vnmfnptlea qyiklypvsc hrgctlrfel
  301 lgcelhgcse plglknntip dsqmsasssy ktwnlrafgw yphlgrldnq gkinawtaqs
  361 nsakewlqvd lgtqrqvtgi itqgardfgh iqyvasykva hsddgvqwtv yeeqgsskvf
  421 qgnldnnshk knifekpfma ryvrvlpvsw hnritlrlel lgc
```

*Included in Table 1 are RNA nucleic acid molecules (e.g., thymines replaced with uridines), nucleic acid molecules encoding orthologs of the encoded proteins.
*Also included in Tabel 1 are orthologs of the proteins.
Unless otherwise indicated, the practice of the disclosure employs conventional techniques of cell biology, cell culture, molecular biology, transgenic biology, microbiology, recombinant DNA, and immunology, which are within the skill of the art.
The following exaples are offered by way of illustration and not by way of limitation.

EXAMPLES

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

Example 1: Materials and Methods

Rodent Fibrosis Model Induction and Efficacy Tests of NP-011

To compare the efficacy of different derivatives of MFG-E8 (NP-011, NP-012, and NP-013) and the full-length protein, MFG-E8, 200 mg/kg of TAA (thioacetamide, Sigma-Aldrich, St. Louis, MO, USA) was administrated into 5- to 6-week-old male C57BL/6 mice (n=4 for each group, 3 times per week for 8 weeks) and each 160 μg/kg of proteins were administrated intraperitoneally. The mice were sacrificed at 3 days after administration of proteins for analysis. Various doses of NP-011 (20 μg/kg~160 μg/kg, n=5 for each group) were further tested in the same TAA-induced liver fibrosis model. To test anti-fibrotic effects of multiple administrations of NP-011, TAA was injected into the mice for 12 weeks, and then 40 μg/kg of NP-011 was intraperitoneally administered into the TAA-induced liver fibrosis model one to six times with a 5-day interval (n=4 for each group). For the progressive liver fibrosis model, TAA was injected into the mice for 4 weeks, then 40 μg/kg of NP-011 and TAA were intraperitoneally co-administered into the mice 3 times a week for another 4 weeks (n=5 for each group). In all animal experiments, the mice were sacrificed three days after the last NP-011 administration; all experimental procedures were approved by the Institutional Animal Care and Use Committee of Korea University (KOREA-2016-0254).

DMN-Induced Cirrhosis Model Induction and Efficacy Tests of NP-011

Animal model for liver cirrhosis was designed and conducted by National Center of Efficacy Evaluation for the Development of Health Products Targeting Digestive Disorders (NCEED, Incheon, Korea). Liver cirrhosis was induced by intraperitoneal injection of dimethylnitrosamine (DMN in saline, 10 mg/ml/kg) for 3 consecutive days each week during a 6-week period using male 6-week-old Sprague-Dawley rats (Orient Bio, Gapyeong, Korea). To minimize the body weight deviation between groups, at the first day of the experiment and the week 3, we randomly separated rats two times into 7 groups: G1 (vehicle control, n=10), G2 (fibrosis control, n=12), G3 (NP-011 treated, once a week, n=10), G4 (NP-011 treated, twice a week, n=10), G5 (NP-011 treated, three times a week, n=10), and G6 (NP-011 treated, daily, n=10). Administration of NP-011 was initiated from the week 3 using intravenous (G3-G6) with 40 μg/kg intravenously. General observation was conducted every day and body weight was measured twice for a week. At the end of week 6, all groups of surviving rats were sacrificed for autopsy and calculated the survival rate of each group. Rats were anesthetized with isoflurane and collected blood sample and main organs. After fixing the liver tissue in 10% neutral-buffered formalin solution, histologic assessment and immunohistochemistry were performed with hematoxylin & eosin staining and α-smooth muscle actin antibody by PostBio Inc., (Guri, Korea).

MCD Diet-Induced NASH Mouse 6-weeks-old male C57BL/6 mouse fed standard chow or Methionine and choline-deficient (MCD) diet for 10 weeks. The procedures employed for the handling and care of the animals were approved by the Korea University Institutional Animal Care and Use Committee (KUIACUC-2018-3). After 5 weeks, mice were intraperitoneally injected with saline or NP-011 (20 μg, 40 μg, 80 μg, or 160 μg/kg body weight, once a week, n=5) for more 5 weeks with MCD diet. During the experiment, body weight was measured weekly.

Immunofluorescence Assay

The liver tissues were fixed in 4% paraformaldehyde (PFA) and dehydrated in a graded ethanol series. The tissues were then cleared in xylene and embedded in paraffin. Paraffin-embedded tissue sections were stained with Sirius red (American MasterTech Scientific, Lodi, CA, USA) for the evaluation of liver fibrosis. For immunofluorescence staining, sectioned tissues underwent antigen retrieval with citric acid and tissues blocked with 10% donkey serum containing PBS were probed with the primary antibody against alpha-smooth muscle actin (α-SMA) or albumin (ALB) at 4° C. overnight. For visualization of the staining, the sections were washed with 0.1% bovine serum albumin (BSA) containing phosphate buffered saline (PBS) and stained with fluorescently labeled secondary antibodies (Invitrogen/Thermo Fisher Scientific, Carlsbad, CA, USA). Digital images were captured using a microscope (Nikon, Tokyo, Japan) and analyzed using ImageJ software.

Histopathological Analysis and NAS Score

Liver tissue was fixed in 4% paraformaldehyde, embedded in paraffin, sectioned and stained with hematoxylin and eosin (H&E) according to a standard procedure. Histological scoring of the liver lesions was assessed by grading system for rodent NAFLD, as described (1): Macrovesicular steatosis (0-3), microvesicular steatosis (0-3), hypertrophy (0-3), numbers of inflammatory foci/field (0-3). All cells of randomly picked five images were counted for each histological feature and calculated. For Oil Red 0 staining, OCT-embedded frozen livers were sectioned at 4 μm, and stained with Oil Red 0 staining kit (Lifeline cell technology, Frederick, MD, USA, Cat.LL-0052). Oil Red 0 stained area were measured by Image J. For immunostaining of frozen-sections, OCT-embedded frozen livers were sectioned at 4 μm, slides were permeabilized and masking by 0.1% Triton X-100 and 10% donkey serum. The liver sections were incubated with primary and secondary antibodies specified in Table 2.

TGFβ Luciferase Signaling Reporter Assay

The luciferase signaling reporter array was performed according to the manufacturer's protocol (Qiagen, Hilden, Germany). The detailed methods for whole transcriptome analysis was described in supplementary materials and methods.

Whole Transcriptome Analysis of Mouse Livers

The normal mouse livers (n=3), TAA-induced fibrotic livers (n=3), and NP-011-administrated livers (n=3) were homogenized in cold Trizol (Sigma, USA), and next generation sequencing (NGS) analysis was performed by BGI Tech Solutions (Hong Kong). Gene Set Enrichment Analysis (GSEA) analysis was conducted using GSEAv17 (Broad Institute, Cambridge, MA, USA). The detailed methods for whole transcriptome analysis was described in supplementary materials and methods.

Quantitative Reverse-Transcription PCR (RT-qPCR)

Quantitative polymerase chain reaction (qPCR) was performed using the CFX96 real-time PCR detection system (Bio-Rad, Hercules, CA, USA) with iQ™ SYBR® Green Supermix (Bio-Rad). The specific primers used are provided in Table 3. The mRNA levels were normalized to the level of GAPDH (glyceraldehyde-3-phosphate dehydrogenase).

Cell Culture and Reagents

The human hepatic stellate cell (HSC) line, hTERT-HSC, was cultured in Dulbecco's modified Eagle's medium (DMEM; GE Healthcare Life Sciences, Marlborough, MA, USA) supplemented with 10% fetal bovine serum (FBS; Gibco/Thermo Fisher Scientific, Waltham, MA, USA), 100 U/mL penicillin, and 100 mg/mL streptomycin (Gibco). The human HEK-293FT cells kindly provided from Prof. Hyunggee Kim (Korea university) were cultured in Dulbecco's modified Eagle's medium (DMEM; GE Healthcare Life Sciences, IL, USA) supplemented with 10% fetal bovine serum (FBS; Gibco, NY, USA), 100 U/mL of penicillin and 100 mg/mL of streptomycin (Gibco).

Western Blot and Immunoprecipitation (IP) Analysis

Protein samples were prepared by solubilizing HSCs in RIPA lysis buffer (LPS solution) containing proteinase inhibitors (Roche, Basel, Switzerland). A total of 40 μg of protein from cells was separated by SDS-PAGE (Bio-Rad) and transferred to PVDF transfer membranes (Pall Corporation, Port Washington, NY, USA). The membranes were incubated for 60 mM with 5% skim milk in TBS-T (10 mM Tris-HCl pH 7.9, 150 mM NaCl, and 0.05% Tween-20) to block nonspecific antibody binding sites. After blocking, the membranes were immunoblotted with primary antibodies overnight at 4° C. Antibodies used in the present study are provided in Table 2. For immunoprecipitation (IP) analysis, a total of 400 μg of protein was incubated at 4° C. for 12 hours with 1 μg of TGFβRI antibody, conjugated to protein A/G sepharose beads (Santa Cruz Biotechnology, Inc., Dallas, Texas, USA) washed in lysis buffer, then separated on SDS-PAGE gels. To detect each band in western blot and IP analysis, the membranes were incubated for 2 hours with horseradish peroxidase (HRP)-conjugated secondary antibodies (Thermo Fisher Scientific) at room temperature. After rinsing with TBS-T, the membranes were developed with the Pierce™ ECL western blotting substrate (Thermo Fisher Scientific) to detect bands using a chemiluminescence imaging system (GE Healthcare Life Sciences).

Efficacy Test of NP-011 in 3D Human Liver Fibrosis Model

In order to establish human liver fibrosis model, the liver spheroids were formed by mixture of hepatocytes (Hepatosight-S®, NEXEL, Seoul, South Korea) and hTert-HSCs (kindly provided from Dr. David Brenner, University of California at San Diego, Ca, USA) in ultra-low attachment 96 well plate (Corning) with the cell density ratio 2 to 1, respectively. The liver spheroids were cultured for 21 days, and 50 mM of acetaminophen (APAP) was treated to induce the fibrosis. To test the efficacy of NP-011 against the APAP-induced 3D liver fibrosis model, 500 ng/ml of NP-011 was treated for 48 hr.

In Vitro Studies for HSC Activation

To investigate the effects of NP-011 on TGF-β1-mediated HSC activation, human HSC lines (hTERT-HSCs) were grown in the presence of serum, then starved in DMEM containing 0.2% FBS 24 hr before TGF-β1 treatment. The serum-starved HSCs were pre-treated with 10 ng/mL TGF-β1 for 1 hour, and the HSCs were exposed to 100-1500 ng/mL NP-011 for 6 hours. For blocking integrin αvβ3/β5 in the HSCs, the HSCs were pre-treated with 1 μM CT (Selleck Chemicals, Houston, Texas, USA) for 2 hours before treating with TGF-β1. The activation and deactivation of HSCs was quantitatively determined by 5-ethynyl-2'-deoxyuridine (EdU) assay.

Proximity ligation assay (PLA)

For the PLA incorporation assay, human HSCs were seeded at $2\times10^4$ cells per well on the 18 mm circular cover glass in 12-well plates and cultured for 24 hours. After serum starvation for 24 hours, the cells were treated with 10 ng/ml of TGF-β1 and/or 500 ng/ml of NP-011, and then, further incubated for 30 minutes. The PLA incorporation was accessed using the Duolink In Situ Red Starter Kit (Merck) according to the manufacturer's instructions. Digital images of PLA-positive cells were captured using a microscope (Nikon) and analyzed using ImageJ software World Wide Web at imagej.nih.gov/ij.

EdU Incorporation Assays

For the EdU incorporation assay, human HSCs were seeded at $2\times10^4$ cells per well in 12-well plates and cultured for 24 hr. After treatment with TGF-β1 and/or NP-011, the serum-starved HSCs were incubated with EdU (10 μM) for an additional 6 hours and EdU incorporation was accessed using the Click-iT EdU Imaging Kit (Thermo Fisher Scientific) according to the manufacturer's instructions. Digital images of EdU-positive cells were captured using a microscope (Nikon) and analyzed using ImageJ software.

Collagenase Activity Assay

The collagenase activity assay was performed according to the manufacturer's protocol (Chondrex, WA, USA). Enzyme sources were mixed with 180 μl of solution B. Enzymatic reaction was initiated by mixing with 200 μl of 1.0 mg/mL FITC-labeled bovine collagen I substrate, followed by incubation at 37° C. for 1 hour. For negative controls, the enzymatic reaction was performed either without the collagen substrate or the enzyme source. To stop the enzymatic reaction, 10 μl of 10 mM o-phenanthroline and 10 μl of 38.5 μM elastase were added to every sample, followed by incubation at 37° C. for 10 mins. Finally, a 400 μl aliquot of extraction buffer was mixed well with the reaction solution, which was then centrifuged at 10,000 rpm for 5 mins. The supernatant (200 μl) was used for the measurement of FL intensity at 520 nm with the spectrofluorimeter during 490-nm excitation in black 96 well plate.

THP-1 Differentiation and Fluorescent Bead Phagocytosis Assay.

THP-1 cells were purchased from ATCC and cultured in RPMI-1640 (Gibco, 31800-022) containing 10% of heat inactivated fetal bovine serum (gibco, 16000-044) and 50 μM β-mercaptoethanol in 37° C., 5% $CO_2$ incubator. THP-1 cells were differentiated into macrophages using 200 ng/ml of phorbol 12-myristate 13-acetate (PMA, Sigma, P8139) for 48 hours followed by 72 hours in PMA-free medium. In phagocytosis assay, THP-1 cells were seeded at $1.05\times10^5$ cells/cm². Carboxylate-Modified Microspheres, 2.0 μm, yellow-green fluorescent beads (Invitrogen, F8827) were washed in THP-1 cell culture media and resuspended at a final dilution of 1:500 in serum free RPMI-1640. Cells were incubated with fluorescent beads for 4 hours in 37° C., 5% $CO_2$ incubator. Cells were detached with TrypLE (Gibco, 12604-021) and measured by flow cytometry (Accuri C6 Plus).

Biodistribution Study 6-weeks-old, male C57BL/6 mouse were randomized into two groups, the control group (Saline) and the NP-011 treated group (NP-011, 160 μg/kg body weight in saline) with 3 animals for each time-point. Mice were injected intravenously and maintained for different time-points. Mice were sacrificed by $CO_2$ inhalation, and the organs (brain, heart, lung, liver, kidney, and spleen) were collected directly in PBS to remove the fat and blood traces. The organs stored at −80° C. immediately. The procedures employed for the handling and care of the animals were approved by the Korea University Institutional Animal Care and Use Committee (KUIACUC-2018-0027 and KUIACUC-2018-0040). Whole organs were homogenized by Lysis buffer (RayBiotech, Norcross, GA, USA, Cat.EL-LYSIS) with COmplete™ Protease Inhibitor Cocktail (Sigma-Aldrich. Cat.11697498001) at 4° C. After homogenization, samples were centrifuged for 20 min at 13,000 rpm at 4° C. and the supernatant was collected for ELISA analysis. The Bio-Rad Bradford was used to calculate protein concentration of each samples. To detect the NP-011, Human MFG-E8 Quantikine ELISA kit (R&D. Cat.DFGE80) was performed following manufacturer's instructions. The result was measured at 450 nm, 540 nm and 570 nm by SpectraMax® iD3 (Molecular Devices. San Jose, CA, USA).

Repeated Dose 28-Day Chronic Toxicity Study 4-week repeated toxicity study of NP-011 was conducted by ChemOn Inc. (Non-clinical CRO company, Korea, Gyeonggi-DO). Total 30 SD rats (15 males and 15 females, 6 weeks-old) were randomly divided into 3 groups; G1 (vehicle control), G2 (NP-011 0.2 mg/kg, daily), and G3 (NP-011 2.2 mg/kg, daily), each 5 male rats and 5 female rats per group. The vehicle and NP-011 were administrated via tail vein of rates. The body weight and consumption of food and water were measured once before the start and every week during the test in all groups. After the end of the study, all rats were sacrificed with blood sampling for the examination of ophthalmology, urine, hematology, biochemistry, and histopathology. The histopathological assessment was performed in all major organs and area (brain, liver, heart, spleen, lung, kidney, bone marrow-sternum, injection site, testis/uterus, and thymus).

Statistical Analysis

Numerical values were expressed as the mean±SEM of at least three independent experiments performed in triplicate for in vitro studies. To evaluate the anti-fibrotic effects of NP-011 in vivo, at least three animals per group were used in each experiment and data were obtained from two to three independent experiments unless indicated. The percentages of areas positive for the Sirius red staining or immunostaining of total image area were measured using ImageJ software and expressed as relative values compared to those in normal livers or control cell cultures, which were arbitrarily set as 1. The Student's t-test was used to analyze the statistical significance of differences between the paired groups. One-way analysis of variance (ANOVA) was used to test the statistical significance of differences among multiple groups (more than two groups). The data are expressed as means and 95% confidence intervals (CI). All statistical tests were two-sided and data with P<0.05 or P<0.01 were assumed to be statistically significant.

TABLE 2

| Antibody | Vendor | Application | Designation |
|---|---|---|---|
| β-actin | Abcam | WB | ab25894 |
| p-Smad2 | Abcam | WB | ab188334 |
| Smad2 | Abcam | WB | ab33875 |
| TGFBRI | Abcam | IP | ab31013 |
| Integrin B3 | Abcam | WB, IP | ab25894 |
| Integrin B5 | Cell Signaling | WB, IP | #3629 |
| Mouse α-SMA | Abcam | IF (Frozen) | ab21027 |
| Mouse F4/80 | Bio-rad | IF (Frozen) | MCA497 |
| Human MFG-E8 | R&D | IF (Frozen) | RD27890 |
| Donkey anti-Goat IgG (H + L) Highly Cross-Adsorbed Secondary antibody, Alexa Fluor 594 | Invitrogen | IF (Frozen) | A11058 |
| Donkey anti-Rabbit IgG (H + L) Highly Cross-Adsorbed Secondary antibody, Alexa Fluor 594 | Invitrogen | IF (Frozen) | A21207 |
| Donkey anti-Mouse IgG (H + L) Highly Cross-Adsorbed Secondary antibody, Alexa Fluor 488 | Invitrogen | IF (Frozen) | A21202 |
| Goat anti-Rabbit IgG (H + L) Secondary Antibody, HRP | Invitrogen | WB | 31460 |
| Donkey anti-Sheep IgG (H + L) Secondary Antibody, HRP | Invitrogen | WB | A16041 |
| α-SMA | Santacruz | IF | sc-53142 |
| Donkey anti-Rabbit IgG (H + L) Highly Cross-Adsorbed Secondary Antibody, Alexa Fluor 594 | Invitrogen | IF | A21207 |

TABLE 3

| Species | Primer | Sequences (5' -> 3') |
|---|---|---|
| Mouse | Gapdh | F: GTT GTC TCC TGC GAC TTC A |
|  |  | R: GGT GGT CCA GGG TTT CTT A |
| Mouse | Col1a1 | F: CAA TGC AAT GAA GAA CTG GAC TGT |
|  |  | R: TCC TAC ATC TTC TGA GTT TGG TGA |
| Mouse | Col1a2 | F: GCA GGG TTC CAA CGA TGT TG |
|  |  | R: GCA GCC ATC GAC TAG GAC AGA |
| Mouse | Acta2 (αSMA) | F: CTG ACA GAG GCA CCA CTG AA |
|  |  | R: CAT CTC CAG AGT CCA GCA CA |
| Mouse | Tgfb | F: TGA CGT CAC TGG AGT TGT ACG G |
|  |  | R: GGT TCA TGT CAT GGA TGG TGC |
| Mouse | Mmp2 | F: AAC TTT GAG AAG GAT GGC AAG T |
|  |  | R: TGC CAC CCA TGG TAA ACA A |
| Mouse | Mmp9 | F: CTG GAC AGC CAG ACA CTA AAG |
|  |  | R: CTC GCG ACA AGT CTT CAG AG |
| Human | GAPDH | F: GCT CTC TGC TCC TCC TGT TC |
|  |  | R: CCA TGG TGT CTG AGC GAT GT |

TABLE 3-continued

| Species | Primer | Sequences (5' -> 3') |
|---|---|---|
| Human | MMP2 | F: AGC TCC CGG AAA AGA TTG ATG |
|  |  | R: CAG GGT GCT GGC TGA GTA GAT |
| Human | MMP9 | F: CAC GCA CGA CGT CTT CCA |
|  |  | R: AAG CGG TCC TGG CAG AAA T |

Example 2: NP-011 Inhibits Liver Fibrosis

Human MFG-E8 contains three domains: a signal peptide at the N-terminus, an epidermal growth factor (EGF)-like domain that bears an arginine-glycine-aspartate (RGD) motif, and C domains (C1 and C2). Although it is well known that MFG-E8 modulates inflammatory responses by RGD motif-mediated binding to immune cells and engulfing phosphatidylserine (PS)-expressing apoptotic cells, it is unclear how MFG-E8 is responsible for the anti-fibrotic effect. A recent report showed that the C2 domain of MFG-E8 plays a key role in recognizing PS in apoptotic cells, suggesting the C2 domain may be important for the over all function of MFG-E8, including its anti-fibrotic effect. To test this, it was synthesized herein two different truncated forms of MFG-E8 along with the EGF domain to maintain the RGD motif for cell binding (NP-011: EGF-C1 domain and NP-012: EGF-C2 domain). As a control, full length MFG-E8 (NP-013) was also synthesized.

Figure 1D:
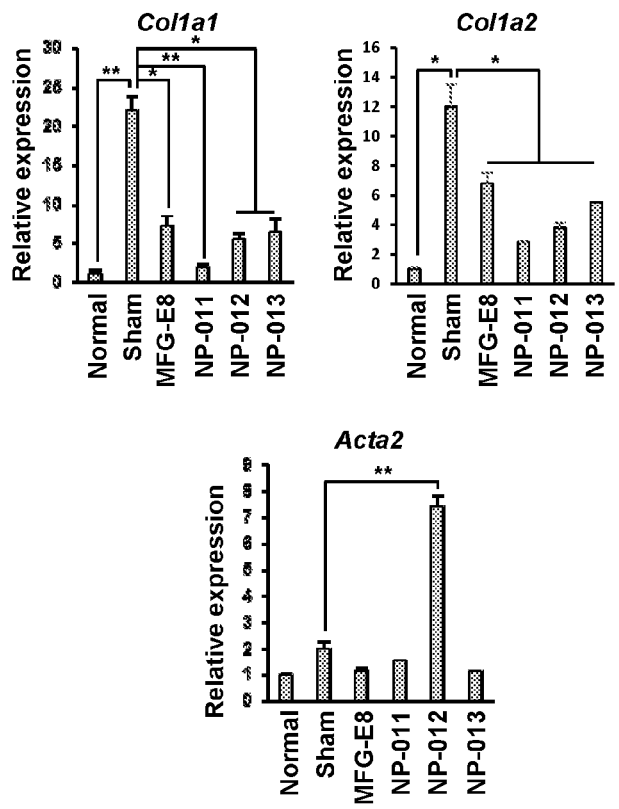
Figure 1E:
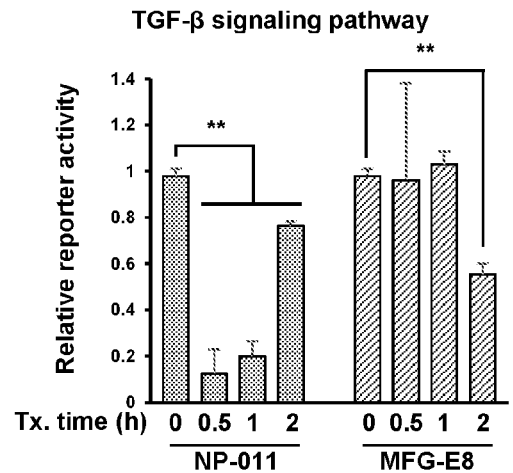
Figure 1F:
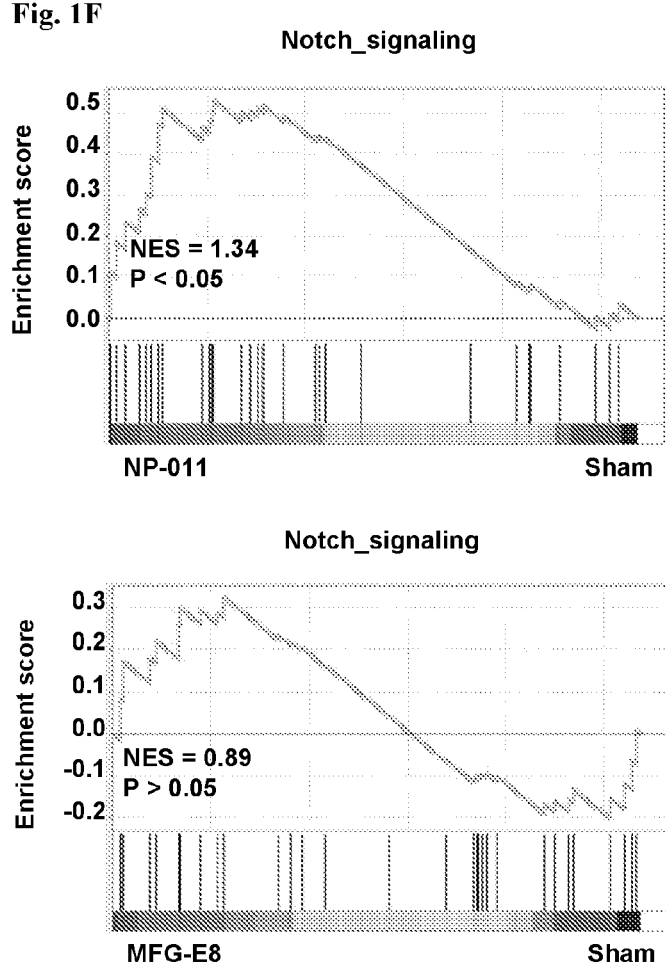

A subsequent efficacy test in a thioacetamide (TAA)-induced liver fibrosis mouse model (FIG. 1A) revealed that the administration of commercial MFG-E8 or NP-013 effectively reduced the fibrotic area (Sirius red-stained area, FIG. 1B and FIG. 1C) and downregulated the expression level of liver fibrosis-related genes (Col1a1, Col1a2, and Acta2) (FIG. 1D). However, it is compelling that the administration of NP-011 eliminated the fibrotic area more substantially and downregulated the expression level of fibrotic genes in the injured liver more significantly than the administration of MFG-E8 and NP-013 (FIG. 1B to FIG. 1C). This is surprising because NP-011 lacks the C2 domain that was thought to be important for the function of MFG-E8, including the anti-fibrotic effect of MFG-E8. Unlike the strong efficacy of NP-011, the administration of NP-012 was less efficacious in reducing the fibrotic area than MFG-E8 and NP-013 (FIG. 1B and FIG. 1C) and significantly upregulated the expression of Acta2 (alpha smooth muscle actin, α-SMA) in the injured liver (FIG. 1D). Signaling reporter assay revealed that NP-011 rapidly suppressed TGF-β signaling within 30 min whereas MFG-E8 could suppress the TGF-β signaling 2 h after treatment (FIG. 1E). GSEA further identified that the administration of NP-011 significantly enriched the Notch signaling in whole transcriptome analysis of injured liver (FIG. 1F) which is associated with the regeneration processes of injured liver (15). These results indicate that deletion of the C2 domain of MFG-E8 unexpectedly results in more potent anti-fibrotic effect compared to the full-length protein.

Example 3: NP-011 Significantly Reverses Liver Fibrosis at Minimal Dosage

Figure 2A:
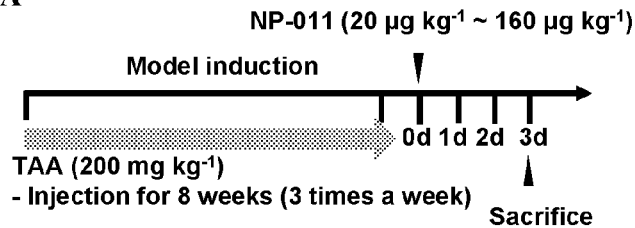
FIG. 2A-FIG. 2F show that NP-011 inhibits fibrosis at low dosage. Resolution of fibrosis by NP-011 at low dosage.
Figure 2B:
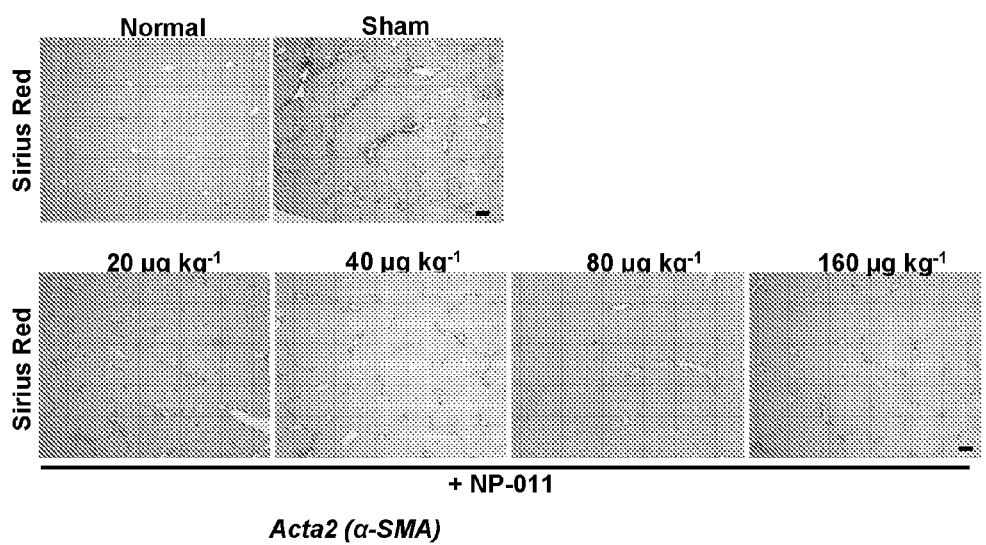
Figure 2C:
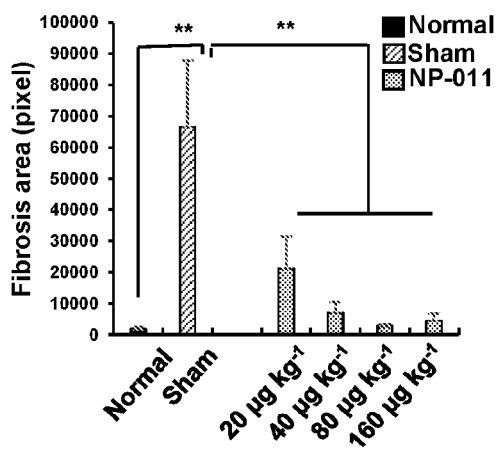
Figure 2D:
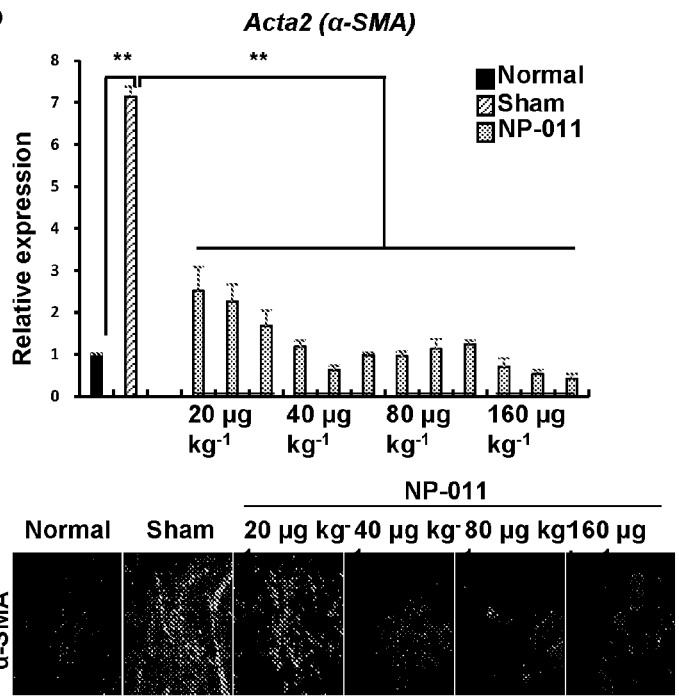
Figure 2E:
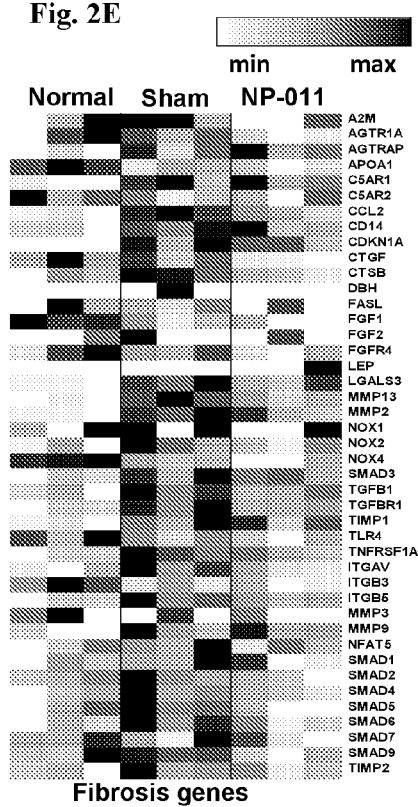
Figure 2F:
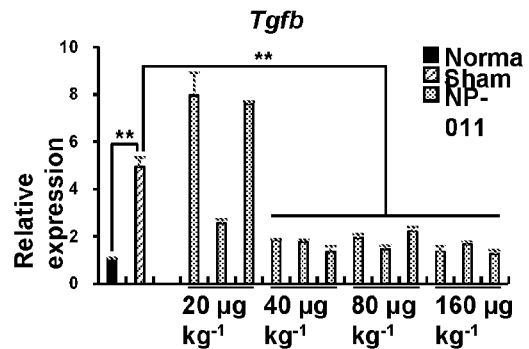

To explore the effective dosage of NP-011, different doses of NP-011 (20 μg/kg, 40 μg/kg, 80 μg/kg, and 160 μg/kg) were administered in a TAA-induced liver fibrosis model and analyzed the fibrotic factors 3 days after NP-011 administration (FIG. 2A). The administration of TAA significantly increased the fibrosis area in the mouse liver (FIG. 2B and FIG. 2C, Sham). In contrast to sham-treated liver tissues, all the NP-011-administrated groups ranging from 20 to 160 ug/kg showed remarkably diminished fibrosis area (FIG. 2B and FIG. 2C). Consistent with the decrease in fibrosis, a key fibrosis marker, Acta2 ($\alpha$-SMA, a marker for myofibroblast-like cells differentiated from HSCs), and other fibrosis-related genes were markedly and significantly downregulated at both mRNA and protein levels after NP-011 administration (FIG. 2D and FIG. 2E). It is noteworthy that the administration of higher doses than 40 μg/kg resulted in the stable and profound suppression of TGF-$\beta$ mRNA expression with slight individual variations (FIG. 2F). Taken together, these results imply that NP-011 shows great therapeutic efficacy at low dosage ranges; most effectively, the administration of 40 μg/kg of NP-011 might be the minimum efficacious dose, resulting in a constant reduction of TGF-$\beta$ expression in injured liver.

Figure 3A:
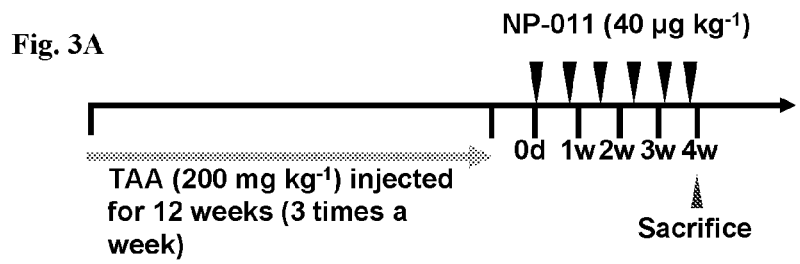
FIG. 3A-FIG. 3E show that NP-011 inhibits and prevents liver fibrosis. Therapeutic efficacy of minimal dosage of NP-011 in various model inductions.
Figure 3B:
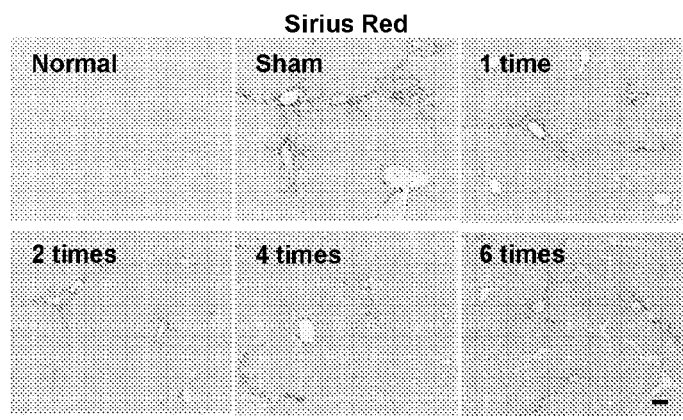
Figure 3B:
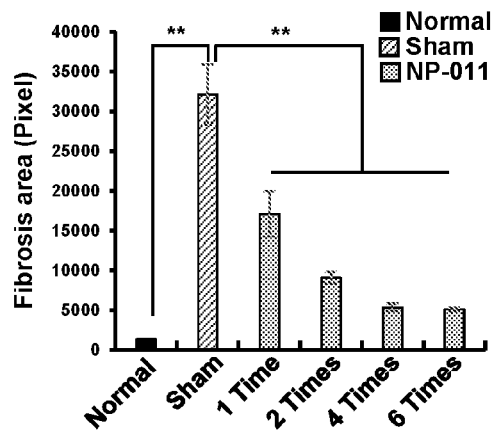

Example 4: The Minimum Dose of NP-011 Shows Therapeutic Efficacy in Different Models Associated with Fibrosis The minimum efficacious dose of NP-011 (40 μg/kg) was further tested in different liver fibrosis models. Firstly, the efficacy of repeated administrations of NP-011 was tested in chronic model of liver fibrosis. For this, TAA injections were extended from 8 to 12 weeks (3 times a week), and then 40 μg/kg of NP-011 was administered to the mice one to six times with 5-day intervals (FIG. 3A). The 12-week TAA injections resulted in the development of sustained fibrosis areas in the liver despite the TAA injections were halted 30 days before sacrificing the mice (FIG. 3B, sham). In contrast, the administration of NP-011 significantly resolved the fibrotic areas in injured livers and the fibrotic regression was positively correlated with the times of administration (FIG. 3B).

Figure 3C:
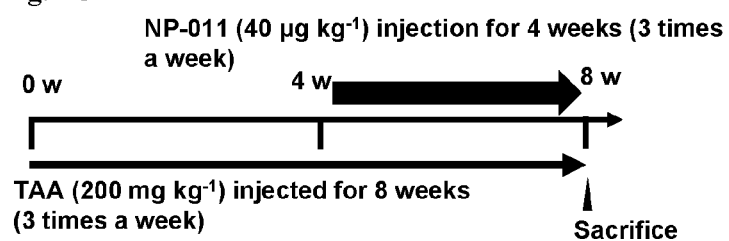
Figure 3D:
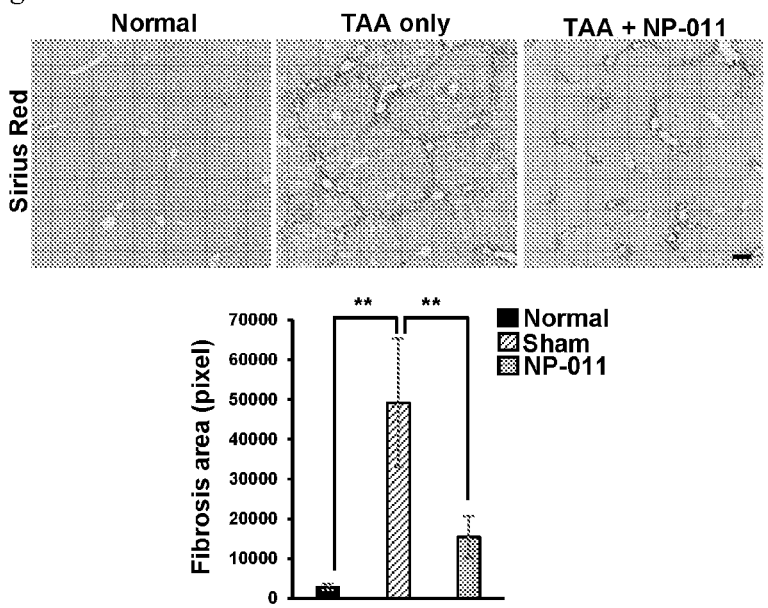
Figure 3E:
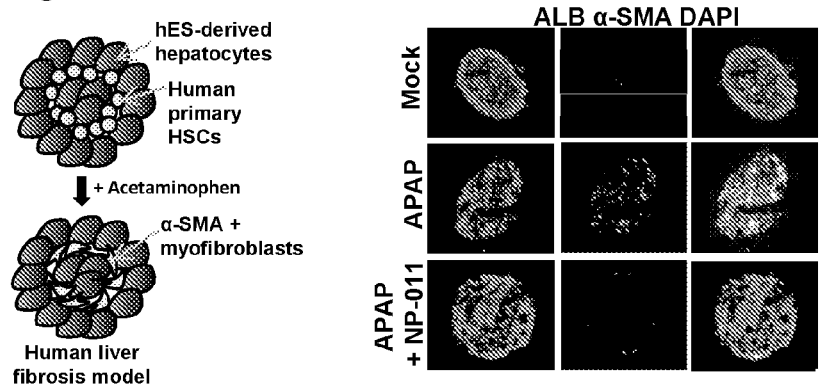
Figure 3E:
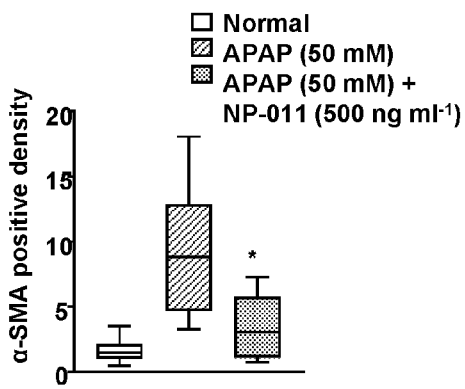

Liver fibrosis is a progressive disease and thus evaluation of the efficacy of NP-011 on progressing liver fibrosis may provide a better translation of the animal study to the clinical realm. To confirm the therapeutic efficacy of NP-011 in the progressing liver fibrosis, the NP-011 (40 μg/kg, three times a week) was concurrently administrated with TAA for last 4 weeks of model induction (FIG. 3C). As expected, the concurrent administrations of TAA and NP-011 markedly diminished the fibrosis areas in the livers, compared with the liver that received TAA only (FIG. 3D). We also used APAP-induced in vitro human fibrosis model and found that NP-011 significantly reduced APAP-induced HSC activation in 3D hepatic spheroids consisting of Hepatocytes and hepatic stellate cells (FIG. 3E).

Figure 4A:
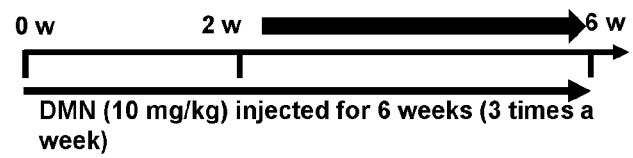
FIG. 4A-FIG. 4D show that NP-011 inhibits and prevents liver cirrhosis. Efficacy test in DMN-induced cirrohosis model in rat.
Figure 4B:
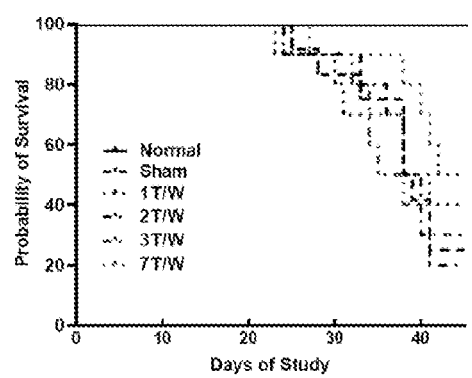
Figure 4C:
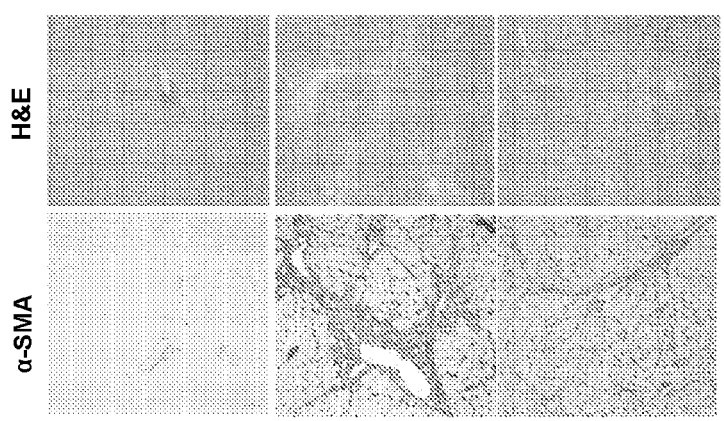
Figure 4D:
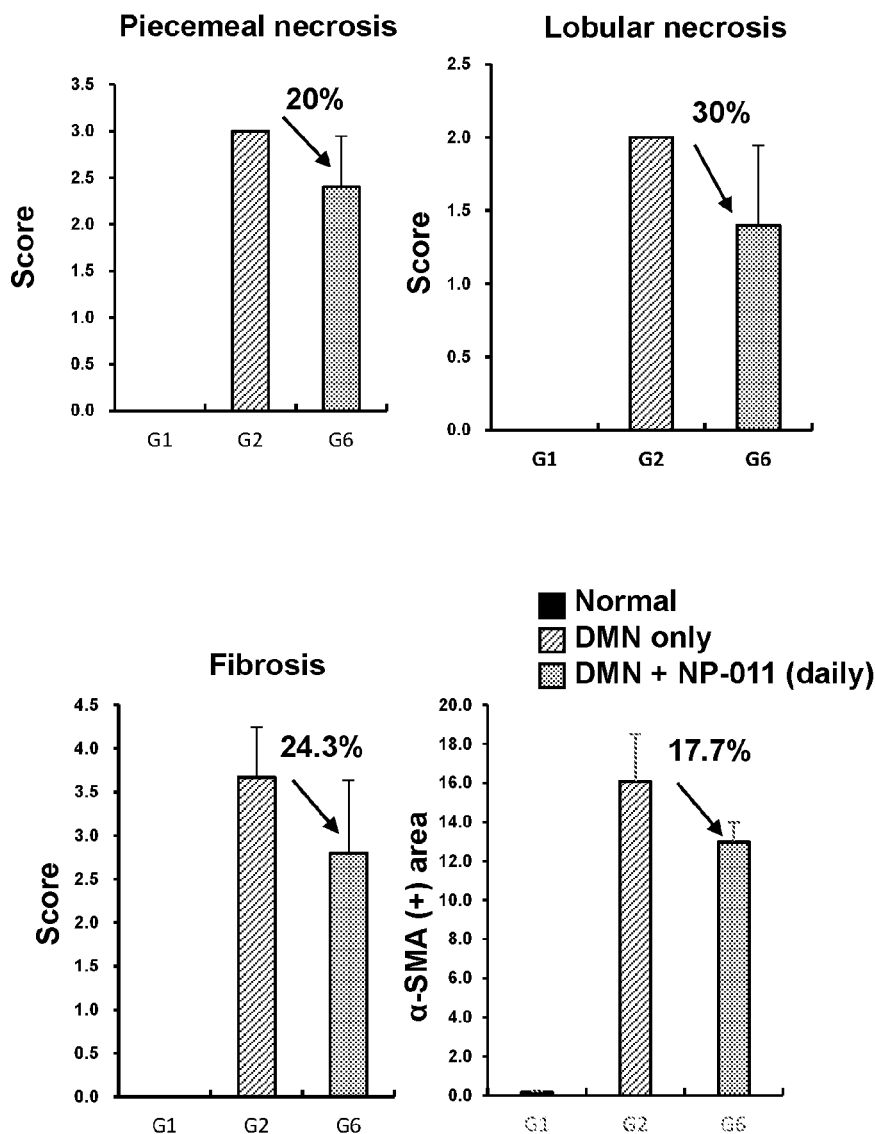

The efficacy of NP-011 was further tested in dimethylnitrosamine (DMN)-induced liver cirrhosis model (FIG. 4A) (16). The DMN injection for 6 weeks in rats resulted the 75% lethality with severe fibrosis in the liver (FIG. 4B and FIG. 4C). Histopathological analysis showed that significant necrotic (piecemeal and lobular) and fibrotic events occurred in the liver of DMN-induced cirrhosis model (FIG. 4D). Importantly, daily administrations of NP-011 reduced the lethality of animals down to 50% with profound attenuation of the liver fibrosis (FIG. 4B and FIG. 4C), and also reduced piecemeal necrosis (~20%), lobular necrosis (~30%), fibrosis score (~24.3%) and HSC activation (~17.7%) (FIG. 4D).

Figure 5A:
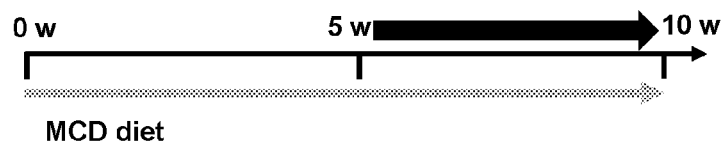
FIG. 5A-FIG. 5D show that NP-011 inhibits and prevents NASH. Efficacy test in MCD diet NASH model.
Figure 5B:
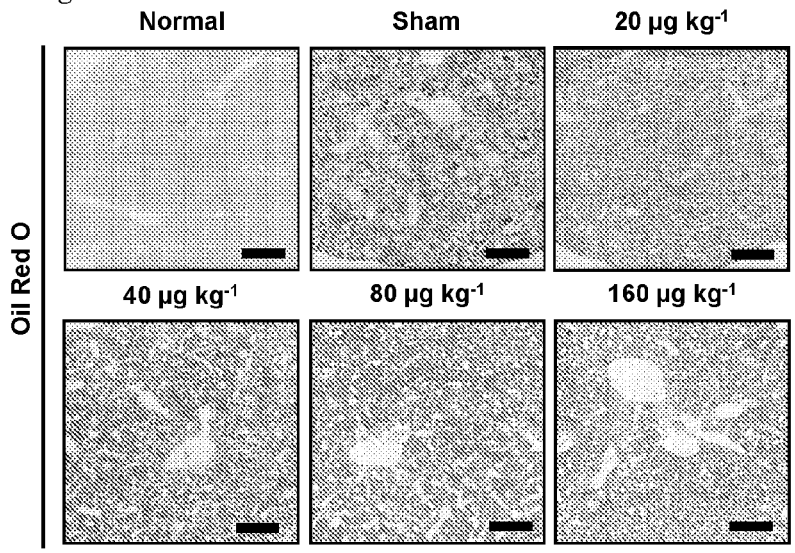
Figure 5C:
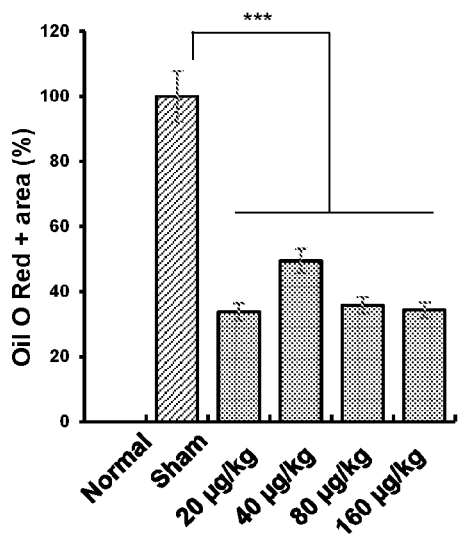
Figure 5D:
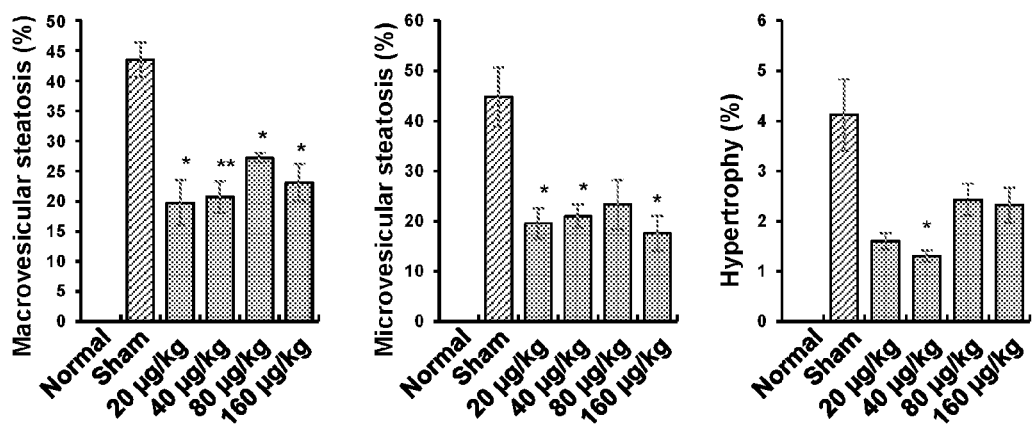

Finally, the efficacy of NP-011 was assessed in methionine-choline deficient (MCD) diet-induced NASH model (FIG. 5A). As reported in various research, MCD diet resulted fat accumulation in the liver, but administrations of NP-011 significantly reduced the fat accumulations in all tested doses (FIGS. 5B and C). Furthermore, significant decreases in the macro-/micro-vesicular steatosis and hypertrophy were observed following NP-011 administration (FIG. 5D). Taken together, NP-011 showed therapeutic efficacies, not only in the severe liver fibrosis but also in NASH at minimum dose.

Figure 6:
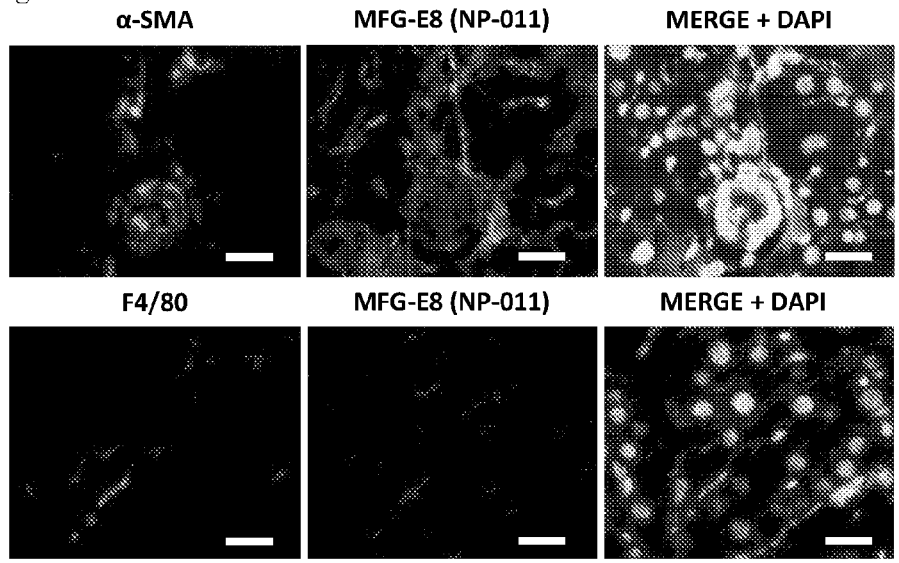
FIG. 6 shows the interaction of NP-011 with activated HSCs and macrophages. Representative images of immunostaining for human MFG-E8 (NP-011), mouse α-SMA, and mouse F4/80 (a marker for macrophages) in the liver tissues of NP-011 administrated TAA-induced liver fibrosis model. Scale bar=20 µm.
Figure 7C:
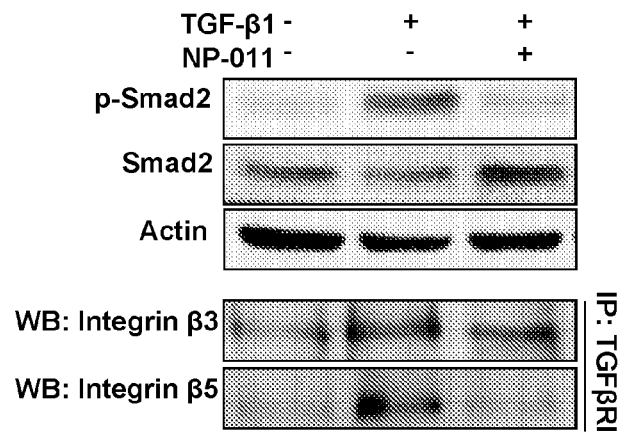
Figure 7D:
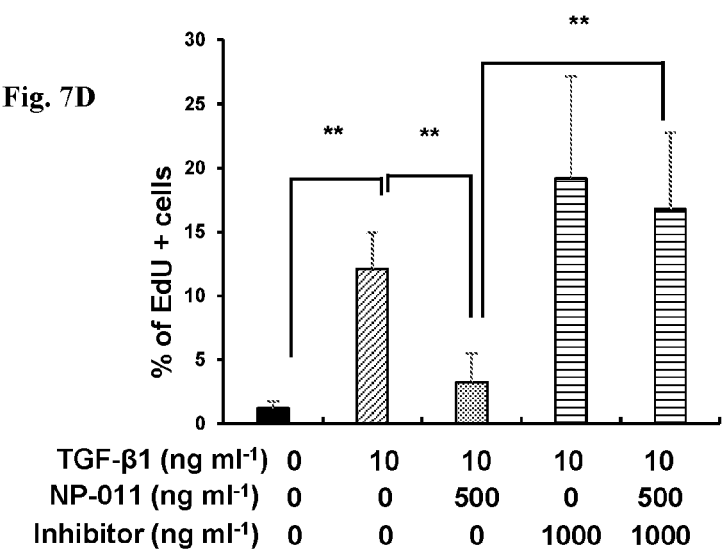

Example 5: NP-011 Resolves Liver Fibrosis by Interaction with Hepatic Stellate Cells (HSCS) and Macrophages in Injured Liver It was investigated herein the mechanism of action for NP-011's rapid and effective suppression TGF-$\beta$ signaling observed in diseased liver (FIGS. 1E and 2F). One day after administration of NP-011 in TAA-induced fibrotic liver, NP-011 preferentially bound to $\alpha$-SMA-positive HSCs, and some of NP-011 interacted with macrophages in the liver (FIG. 6). Integrin $\alpha v \beta 3$ and $\alpha v \beta 5$ on the surface of HSCs have been previously implicated in regulating fibrosis. Additionally, the crosstalk between integrin and TGF-$\beta$ signaling may be important in the regulation of pathological epithelial to mesenchymal transition (EMT) and myofibroblast differentiation. Proximity Ligation Assay (PLA) revealed direct physical interactions between TGFBRI and integrin $\beta 3/\beta 5$, and the interactions became stronger upon TGF-$\beta 1$ treatment in HSCs (FIG. 7A and FIG. 7B). However, NP-011 treatment in TGF-$\beta 1$-treated HSCs significantly decreased the interactions between TGFBRI and integrin $\beta 3/\beta 5$ (FIG. 7A and FIG. 7B). Western blot analysis showed that NP-011 treatment significantly attenuated the phosphorylation of a downstream molecule of TGF-$\beta$ signaling, Smad2, in TGF-$\beta 1$-treated HSCs, and the interactions between TGFBRI and integrin $\beta 3/\beta 5$ were further confirmed by immunoprecipitation assay (FIG. 7C). As a consequences of NP-011 treatment in TGF-$\beta 1$-treated HSCs, the proliferative HSCs returned to quiescent status (FIG. 7D). However, treatment of integrin $\beta 3/\beta 5$ inhibitor in the presence of NP-011 abrogated the suppressive role of NP-011 in the proliferation of TGF-$\beta 1$-treated HSCs (FIG. 7D). Therefore, these results indicate that NP-011 directly binds to integrin $\beta 3/\beta 5$ and interferes with its interaction with TGF$\beta$RI, resulting in suppression of the TGF-$\beta$ cascade and decrease in HSC proliferation.

Figure 8A:
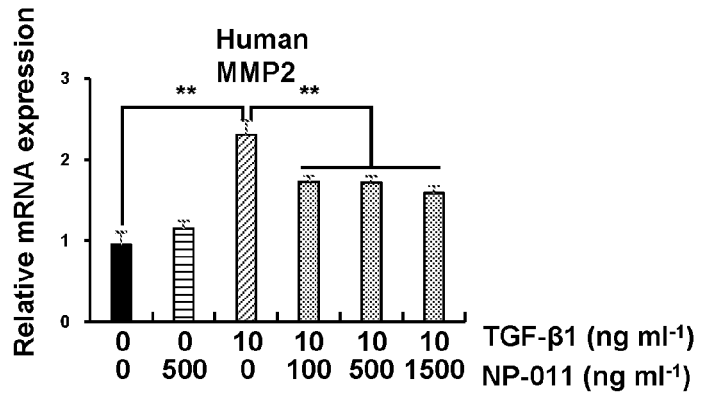
FIG. 8A-FIG. 8C show that NP-011 decreases MMP2 expression and increases collagenase activity. Regulating pro-fobrotic MMP2 and collagenase activity in HSCs.
Figure 8B:
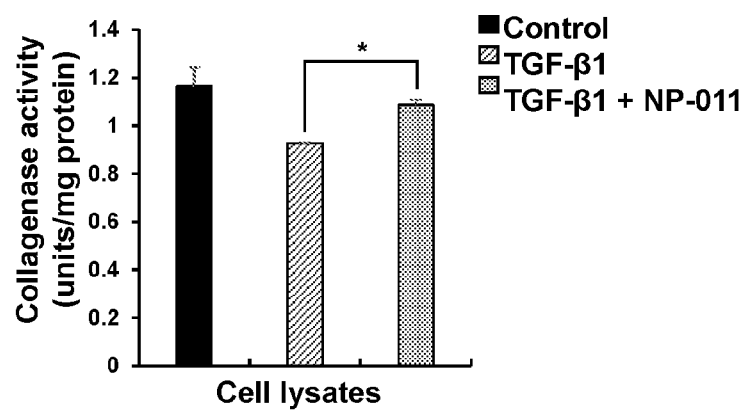
Figure 8C:
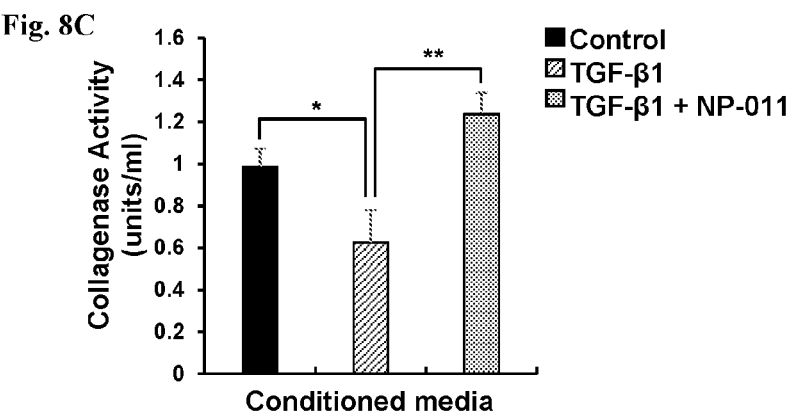

Effects of NP-011 in the expression of pro-fibrotic MMP2 and collagenase activity in HSCs were further tested based on the previous finding that showed secretion of pro-fibrotic MMP2 and expression of collagenase mRNA in rat HSCs. Expression of MMP2 mRNA in HSCs was increased in HSCs after TGF-$\beta 1$ treatment. However, NP-011 treatment in TGF-$\beta 1$-treated HSCs significantly down-regulated the increased expression of MMP2 (FIG. 8A). In contrast, the collagenase activity was down-regulated in HSCs after TGF-$\beta 1$ treatment, and the decreased collagenase activity was recovered in TGF-$\beta 1$-treated HSCs after NP-011 treatment both in cell lysates and conditioned media (FIGS. 8B and C).

Figure 9A:
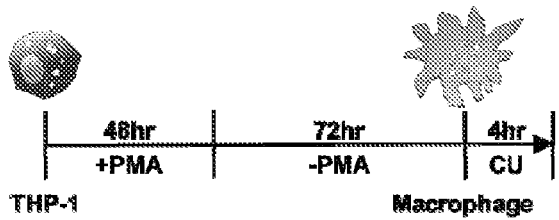
FIG. 9A-FIG. 9E show that NP-011 increases macrophage-mediated collagen uptake.
Figure 9B:
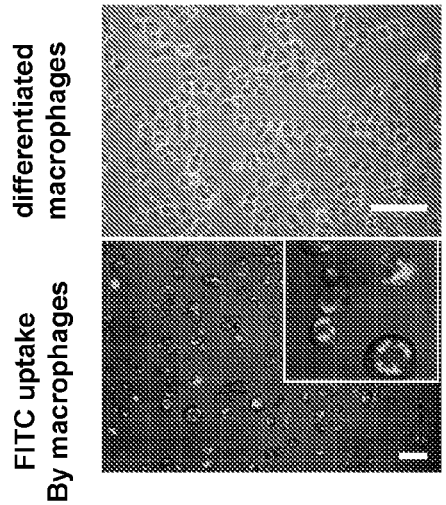
Figure 9C:
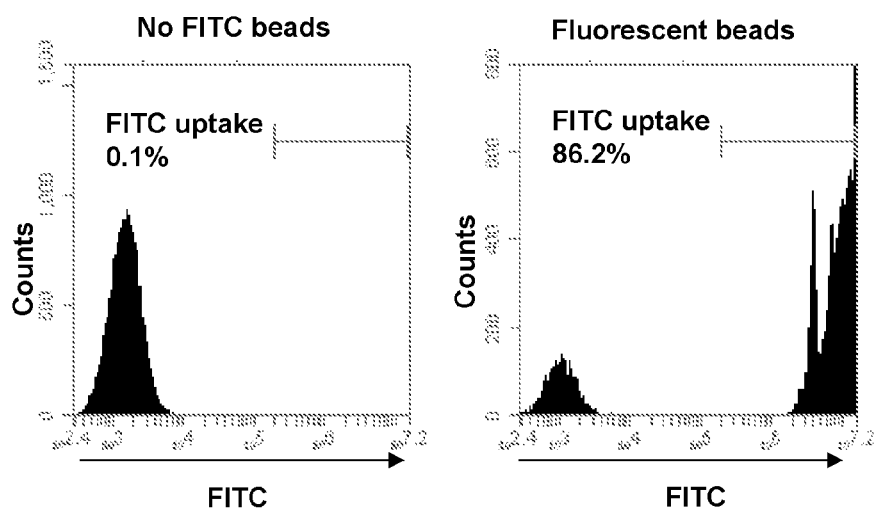
Figure 9D:
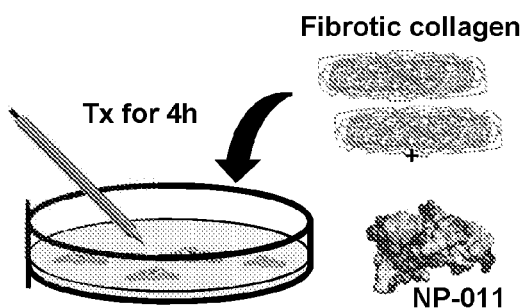
Figure 9E:
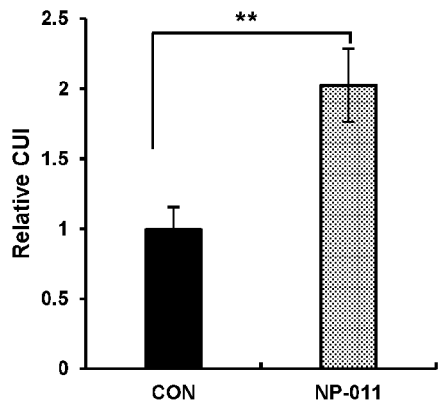
Figure 10:
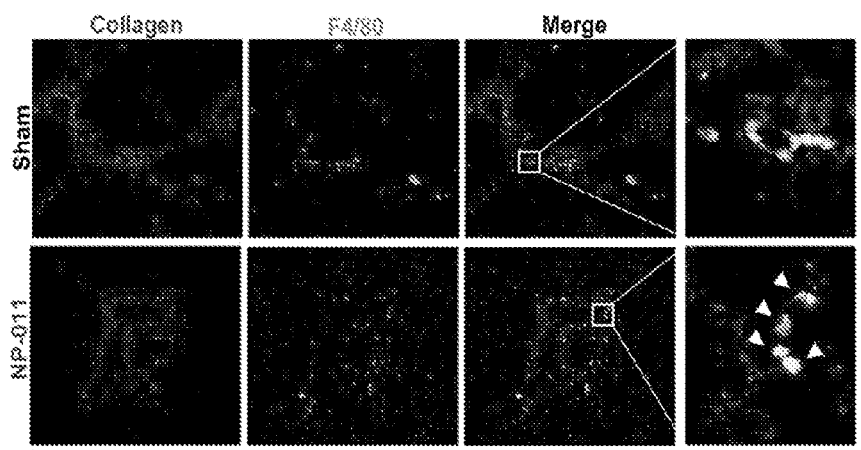
FIG. 10 shows that NP-011 interacts with activated HSCs and macrophages. Representative images of immunostaining for mouse collagen and mouse F4/80 (a marker for macrophages) in the liver tissues of TAA-induced liver fibrosis model and NP-011 administrated TAA-induced liver fibrosis model. Arrow heads indicates the engulfment of collagen by macrophage (F4/80-positive cells).

Elimination of accumulated collagen by immune response is another key factor for resolving fibrosis as seen in lung fibrosis model. In order to assess this, THP-1 monocytes were differentiated into macrophages by PMA treatment (FIG. 9A), and the phagocytic capability of differentiated macrophages was confirmed by fluorescence and flow cytometry analysis (FIGS. 9B and C). Collagen uptake assay revealed that green fluorescence-labelled collagen was significantly up-taken by differentiated macrophages in the presence of NP-011 unlike the control culture (FIGS. 9D and E). In fact, engulfment of collagen by macrophages was demonstrated by immunostaining for collagen and F4/80 after NP-011 administration in TAA-induced liver fibrosis model (FIG. 10, arrow heads in lower panel). Taken together, these results indicate that that NP-011 suppresses TGF-β signaling in injured liver, and then inhibits and resolves liver fibrosis by deactivating active HSCs and interacting with macrophages.

Example 6: Bio-Distribution and Safety Profiles of NP-011

Figure 11A:
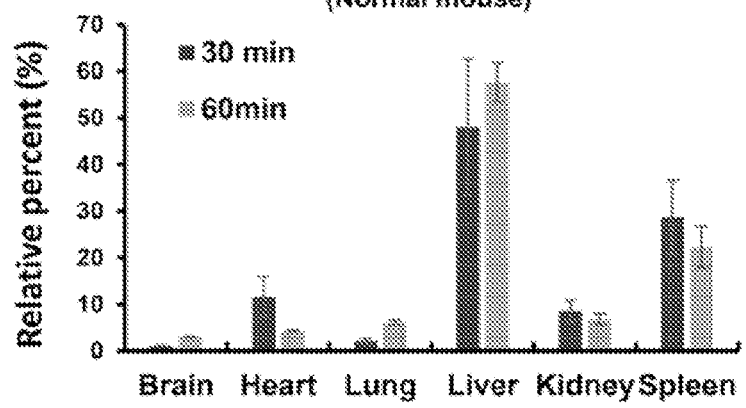
FIG. 11A-FIG. 11C show biodistribution and safety profile of NP-011.
Figure 11B:
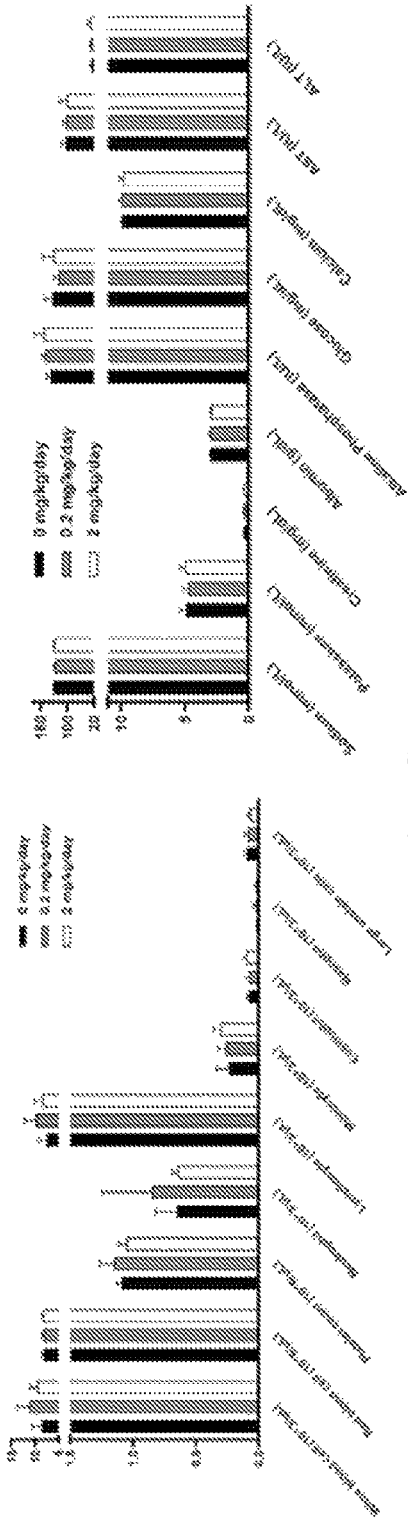
Figure 11C:
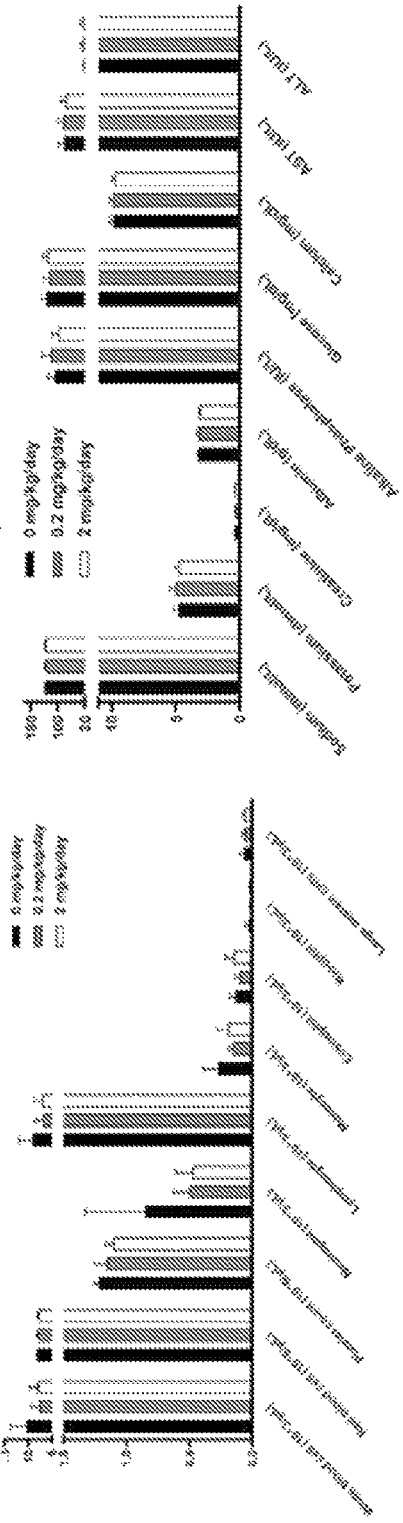
Figure 12:
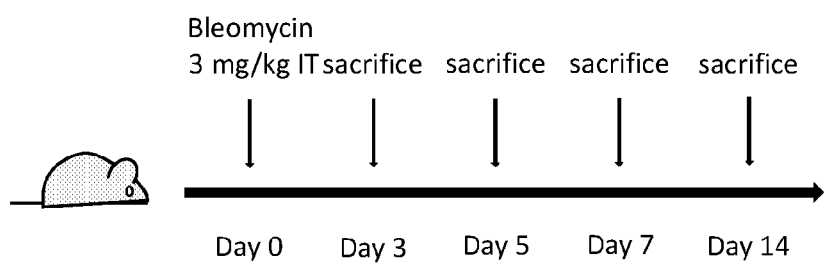
FIG. 12 shows a diagram of a model for idiopathic pulmonary fibrosis (IPF).

Bio-distribution and safety test of NP-011 were further assessed in a rodent model. When the NP-011 was intravenously administered into mice, the administered NP-011 was preferentially delivered into liver, and then about 48% and 58% of administrated NP-011 were detected in the liver within 30 min and 60 min, respectively (FIG. 11). Furthermore, no adverse effects were observed in hematology and biochemistry analysis of blood serum both in male and female rat when 0.2 mg/kg and 2 mg/kg of NP-011 was intravenously administered into rats for 4 weeks daily (FIG. 11). Thus, these results indicate that NP-011 preferentially targets liver after its administration and has excellent safety profiles.

NP-011 shows a powerful anti-fibrotic effect for inhibiting, preventing, and reversing liver fibrosis. NP-011 is superior for clinical application over the full length MFG-E8 (lactadherin) by truncation of the C2 domain for the following reasons: 1) Medin site is eliminated in NP-011 by structural truncation of MFG-E8. Medin is aortic medial amyloid that occurs in people older than 60 years, and accumulated medin is engaged in Alzheimer's disease and type 2 diabetes. MFG-E8 (Lactadherin) has the medin in its component, and it is positioned within C2 domain. Therefore, through the structural truncation of C2 domain from MFG-E8, NP-011 eliminates the concern for inducing amyloid formation in patients upon administration, and the concern for side effects that may cause Alzheimer's disease and diabetes upon repeated administrations into patients. Because the most common liver disease, non-alcoholic fatty liver disease (NAFLD), is closely related with type 2 diabetes, it is a crucial factor for treating liver disease. 2) NP-011 exhibits better binding affinity against collagen by removing the glycosylation sites of MFG-E8. MFG-E8 contains glycosylation sites in the C2 domain. By removing the C2 domain, NP-011 has no glycosylation that might interfere with the binding of the discoidin domain (C1 domain) of MFG-E8 to the accumulated collagen in liver fibrosis. The well-known discoidin domain receptor (DDR) has discoidin domain, stalk region, and transmembrane domain in its structure. Although the mechanism of collagen binding of DDR has not been identified, binding of discoidin domain of DDR to collagen has been reported. Interestingly, the discoidin domain of DDR has no glycosylation (glycosylation sites are only located at stalk region of DDR), therefore, discoidin domain of NP-011 might be similar to the discoidin domain of DDR, and may facilitate binding of NP-011 to accumulated collagen in the liver.

NP-011 has therapeutic efficacy in various liver disease models including nonalcoholic steatohepatitis (NASH). Clinically, nonalcoholic steatohepatitis (NASH) is frequently found in the patient of liver fibrosis because patients with NASH are likely to progress to fibrosis and cirrhosis, and patients with NASH have an almost 10-fold more risk of liver disease-related death than patients with simple steatosis. Thus, the therapeutic capacity of NP-011 in both NASH and fibrosis represent a novel therapy for inhibiting and reversing complex and progressive liver diseases.

High manufacturability is another advantage of NP-011 for clinical application. NP-011 was produced using a yeast system, and this system has several advantages including facile genetic manipulation and rapid growth, as well as eukaryotic features including a secretory pathway for correct protein processing and post-translational modification. Currently, the production yield of NP-011 from yeast resulted 40 mg/L, and this yield provides reliable manufacturing for clinical applications. For example, the production of NP-011 at a general Good Manufacturing Practice (GMP) run scale of 200 L would provide about 3,400 injections for 60-kg adults with the 40 µg/kg of efficacious dosage. Furthermore, NP-011 is produced as a secreted protein (authentic NP-011) without a methionine at the N-terminus of the protein, any tag (e.g., FLAG-tag or his-tag), or random glycosylations, which could induce significant problems upon administration of medications. Thus, in conclusion, NP-011 provides a highly effective and reliable new protein therapy for treating, inhibiting, preventing, and reversing liver fibrosis as well as other liver diseases disclosed herein.

Example 7: NP-011 Reverses, Inhibits, and Prevents Idiopathic Pulmonary Fibrosis (IPF)

Figure 13:
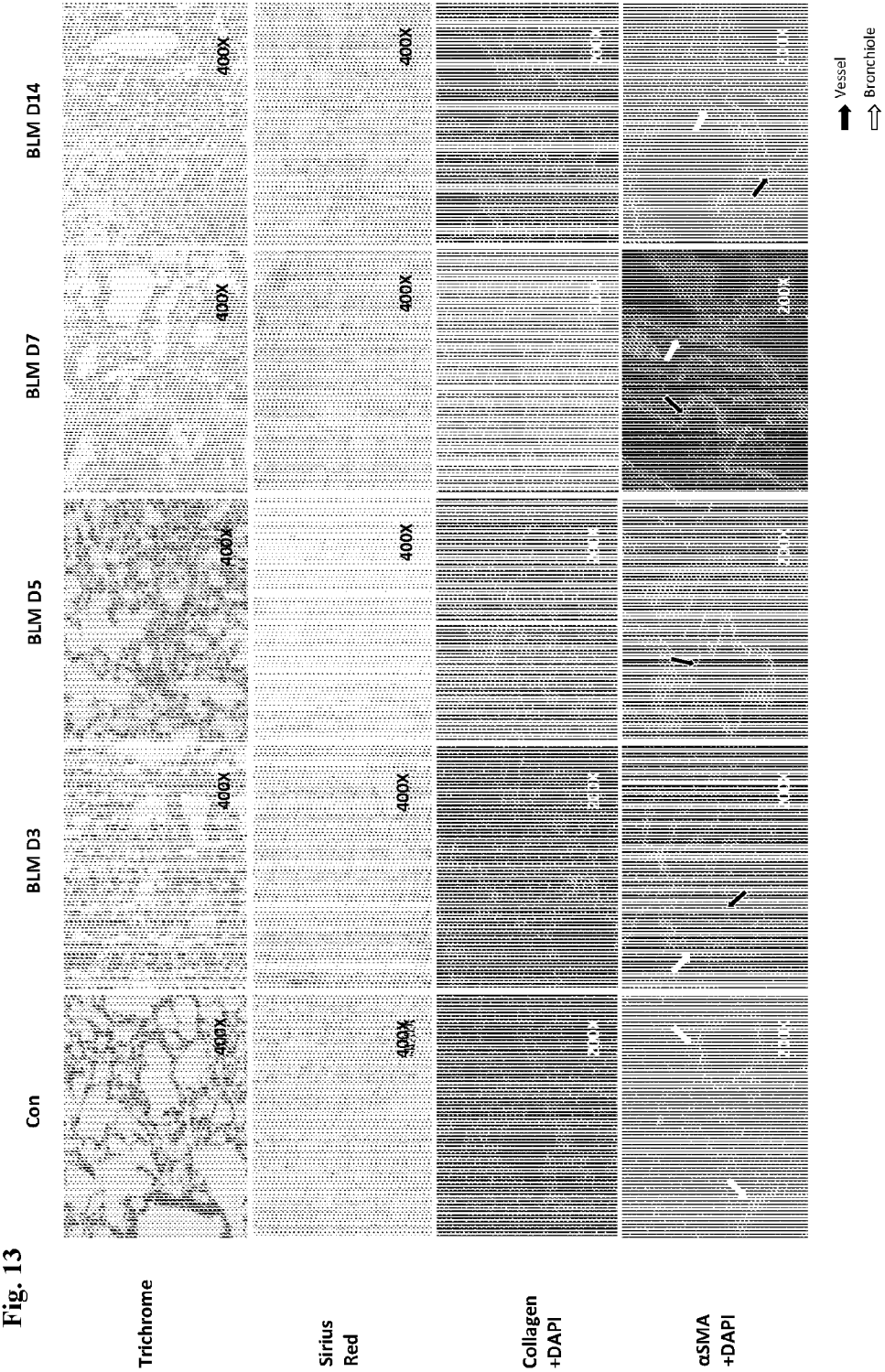
FIG. 13 shows the images of lung tissues that were stained to show distribution of collagen and αSMA at day 3 (D3), day 5 (D5), day 7 (D7), and day 14 (D14) after treatment with bleomycin.
Figure 14:
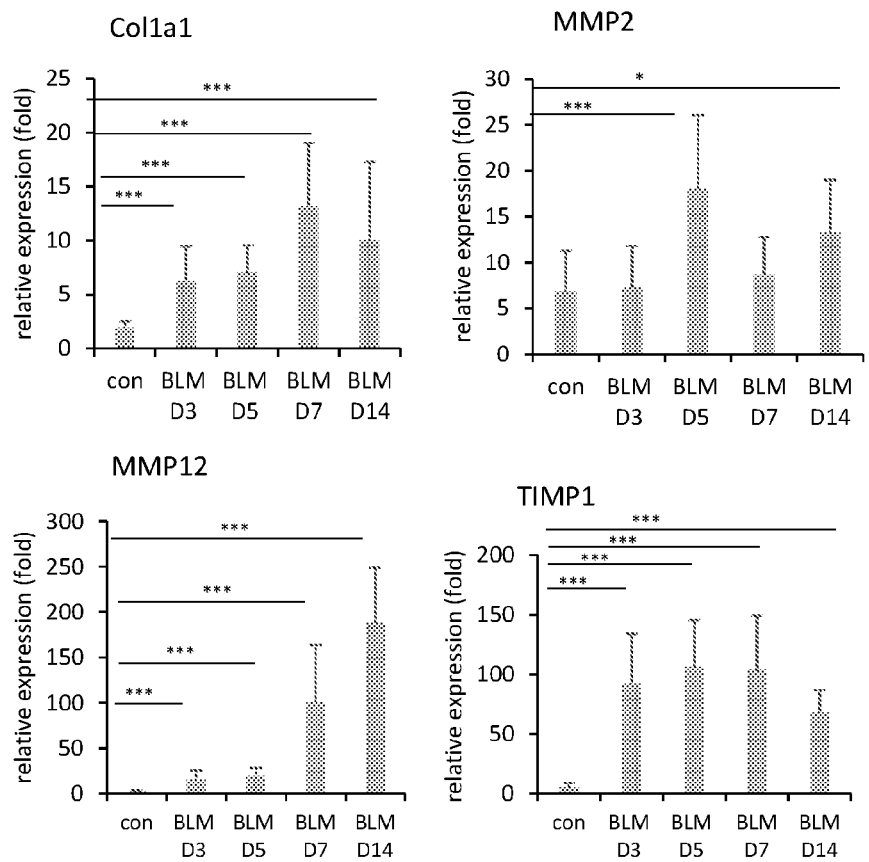
FIG. 14 shows the changes in expression levels of IPF biomarkers (Col1a1, MMP2, MMP12, and TIMP1) at day 3 (D3), day 5 (D5), day 7 (D7), and day 14 (D14) after treatment with bleomycin.
Figure 15:
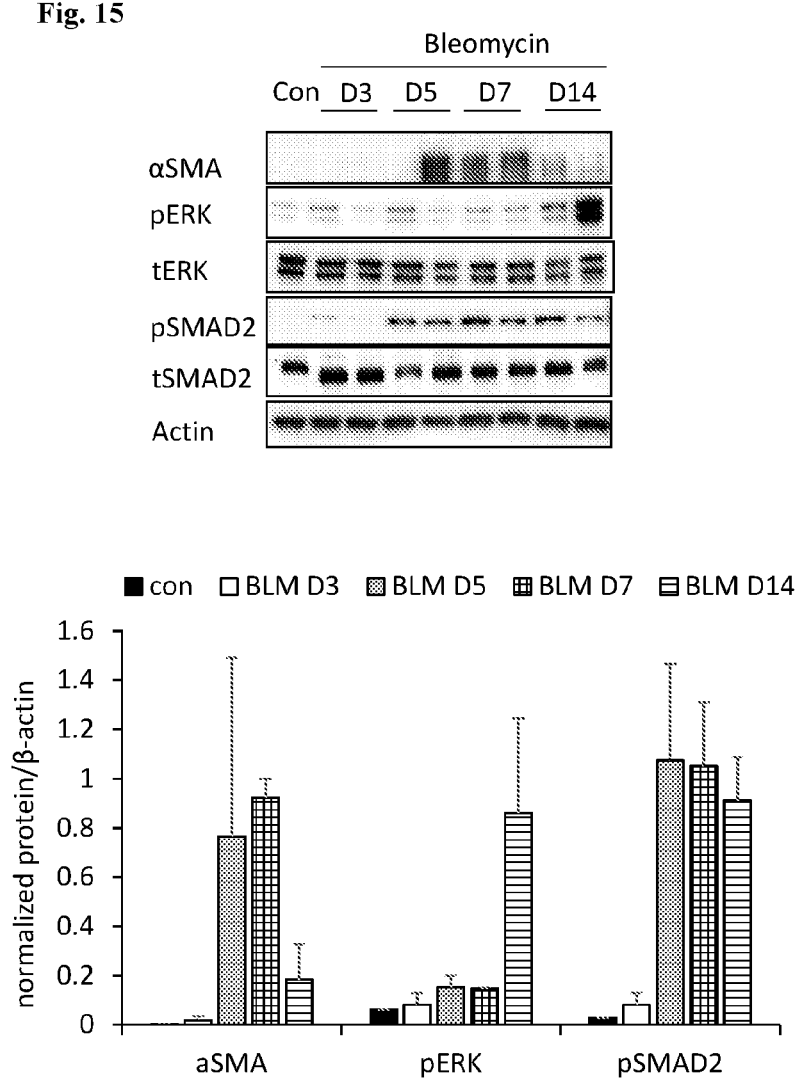
FIG. 15 shows the changes in expression levels of the subfactors of the signaling pathway related to IPF at day 3 (D3), day 5 (D5), day 7 (D7), and day 14 (D14) after treatment with bleomycin. The subfactors include αSMA, pERK, tERK, pSMAD2 (phosphorylated SMAD2), and tSMAD2 (total SMAD2). Actin is shown as a loading control.
Figure 16A:
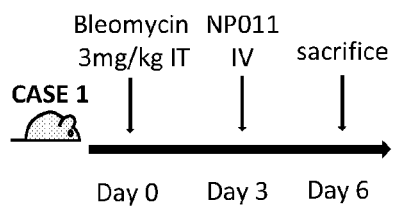
FIG. 16A-FIG. 16B show diagrams of a model for IPF for testing in vivo efficacy of NP-011. Two cases with different time points are presented: Case 1 (FIG. 16A) and Case 2 (FIG. 16B).
Figure 16B:
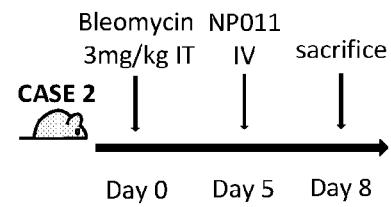
Figure 17:
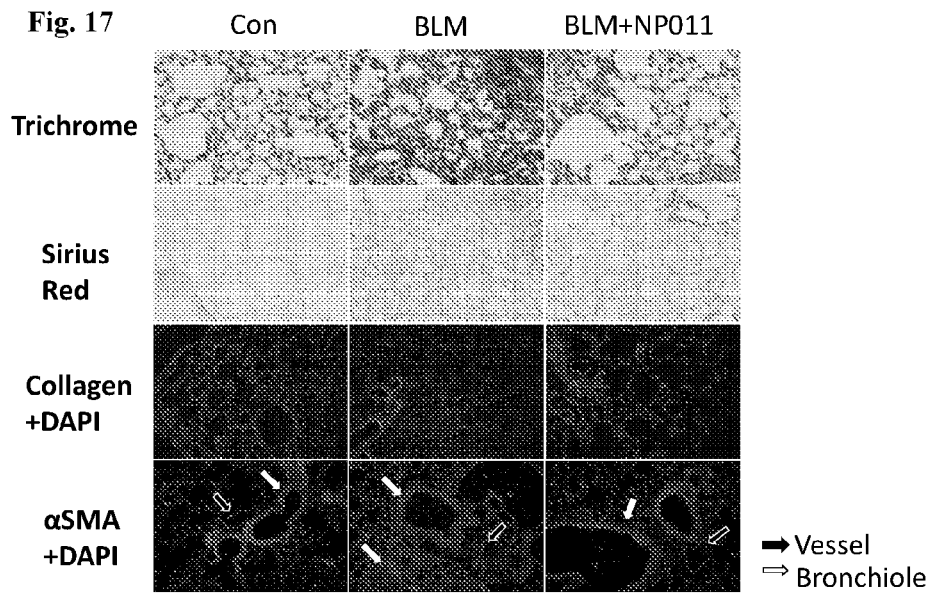
FIG. 17 shows that NP-011 is efficacious against IPF. The lung tissues were stained to show distribution of collagen and αSMA after injection of NP-011. Mice were injected with NP-011 at day 3 (Case 1 of FIG. 16A).
Figure 18:
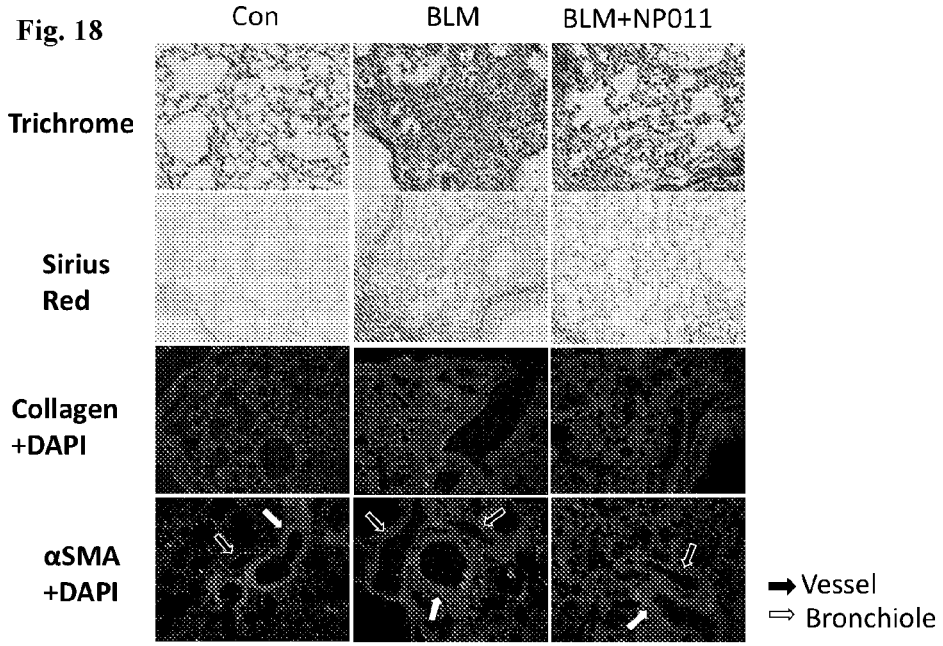
FIG. 18 shows that NP-011 is efficacious against IPF. The lung tissues were stained to show distribution of collagen and αSMA after injection of NP-011. Mice were injected with NP-011 at day 5 (Case 2 of FIG. 16B).
Figure 19:
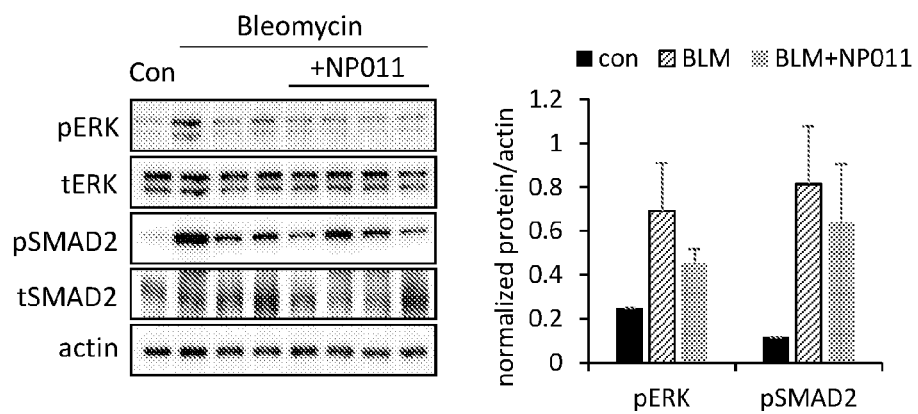
FIG. 19 shows that NP-011 is efficacious against IPF. NP-011 reverses the bleomycin-induced changes in expression levels of the subfactors of the signaling pathway related to IPF. Mice were injected with NP-011 at day 3 (Case 1 of FIG. 16A). The subfactors include pERK, tERK, pSMAD2, and tSMAD2. Actin is shown as a loading control. The histogram in the right panel shows quantification of the expression level of pSMAD2 normalized to the actin level.
Figure 20:
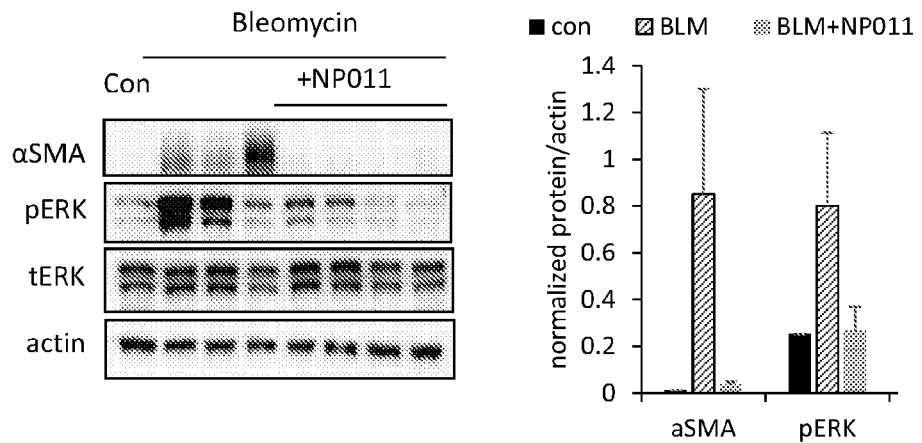
FIG. 20 shows that NP-011 is efficacious against IPF. NP-011 completely reverses the bleomycin-induced changes in expression levels of the subfactors of the signaling pathway related to IPF. Mice were injected with NP-011 at day 5 (Case 1 of FIG. 16B). The subfactors include αSMA, pERK, and tERK. Actin is shown as a loading control. The histogram in the right panel shows quantification of the expression level of pERK normalized to the actin level.
Figure 21:
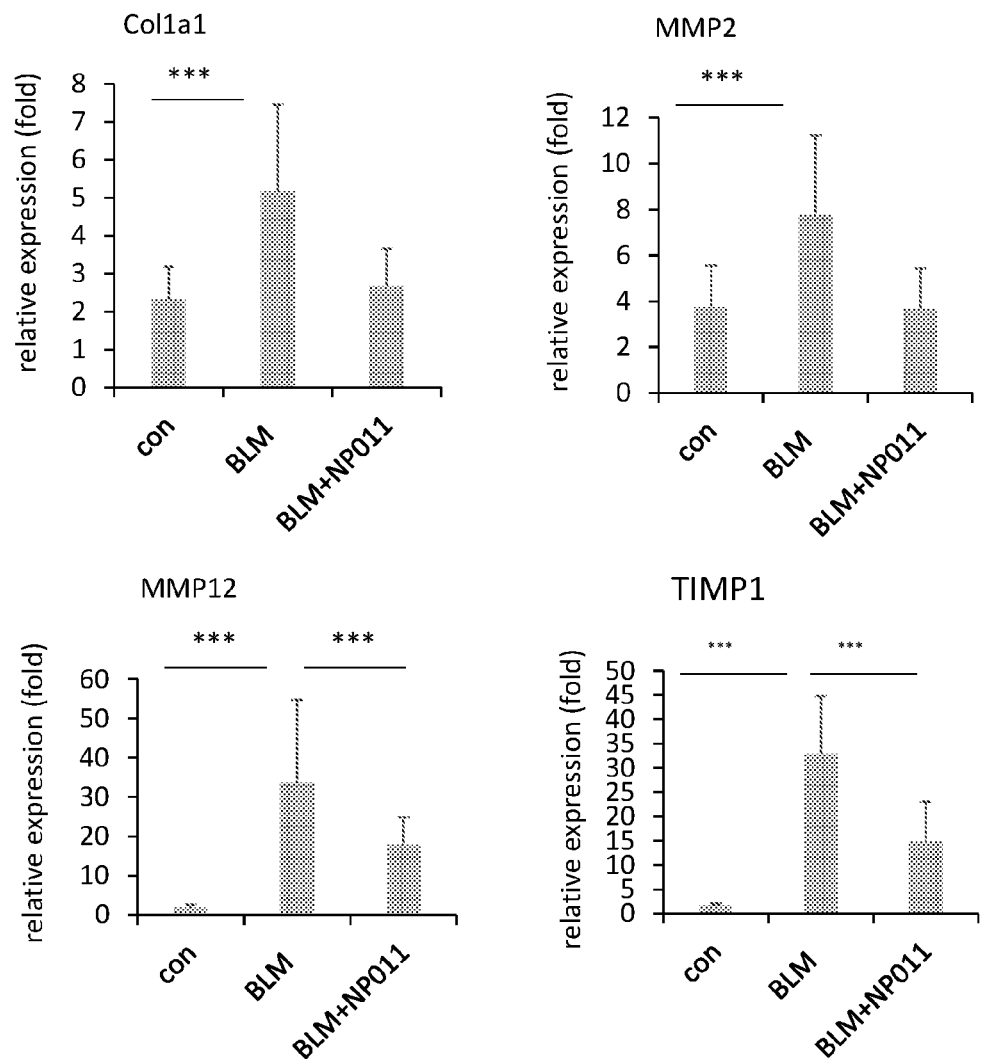
FIG. 21 shows that NP-011 is efficacious against IPF. NP-011 alters the expression levels of IPF biomarkers (e.g., as shown herein collagen (Cola1), MMP2, MMP12, and TIMP1). Specifically, NP-011 reverses the bleomycin-induced increase in expression levels of IPF biomarks.
Figure 22:
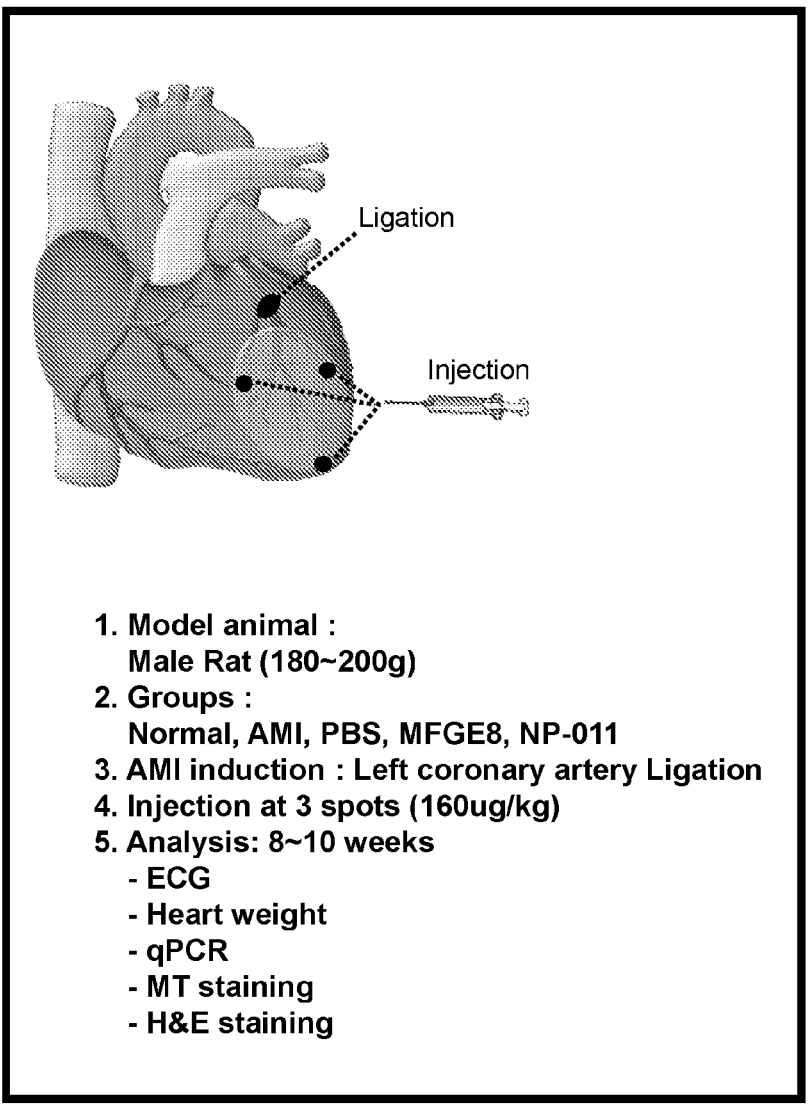
FIG. 22 shows a diagram of LAD-ligation model for myocardial infarction. The left anterior descending artery (LAD) of a rat is ligated with one single stitch, forming an ischemia that can be seen almost immediately. By closing the LAD, no further blood flow is permitted in that area, while the surrounding myocardial tissue is nearly not affected. This surgical procedure imitates the pathobiological and pathophysiological aspects occurring in infarction-related myocardial ischemia (e.g., Kolk et al. (2009) *J Vis Exp*, 21:pii 1438). In addition to the LAD-ligation model, FIG. 22 also presents details of the studies presented in FIG. 23-FIG. 26.
Figure 23B:
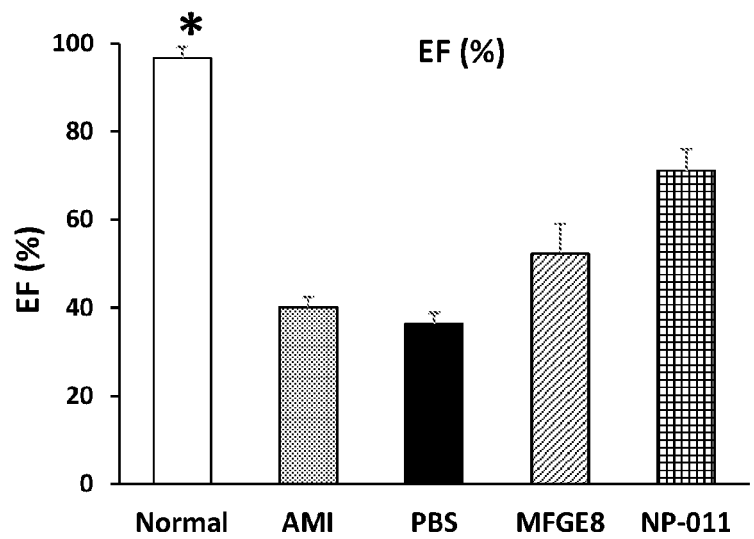
Figure 23B:
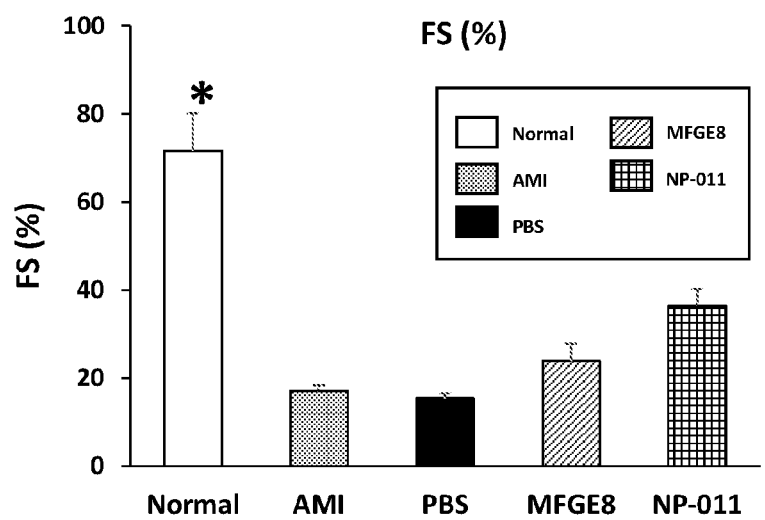
Figure 23C:
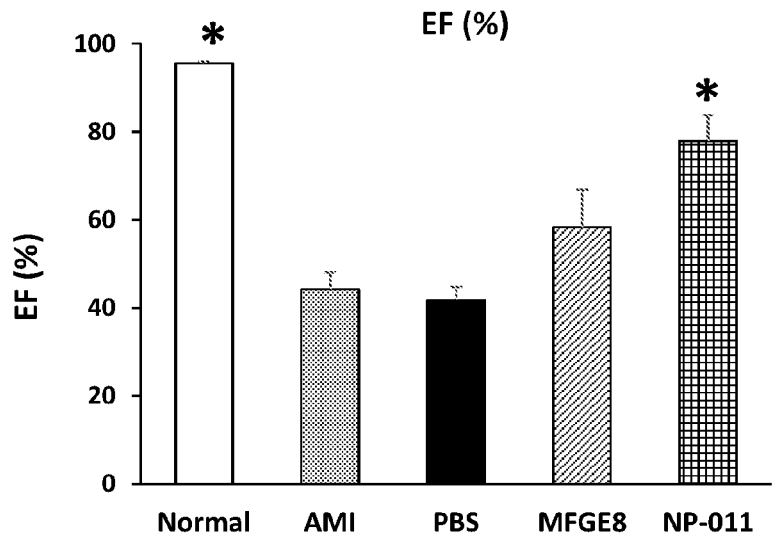
Figure 23C:
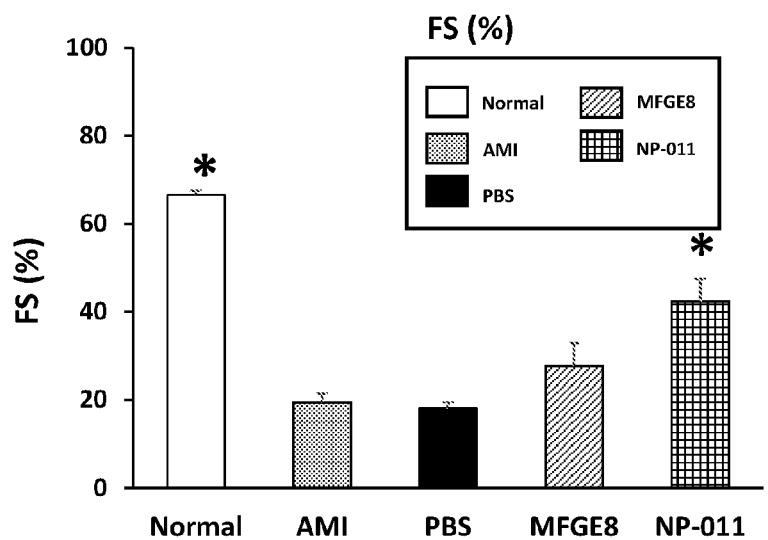
Figure 24A:
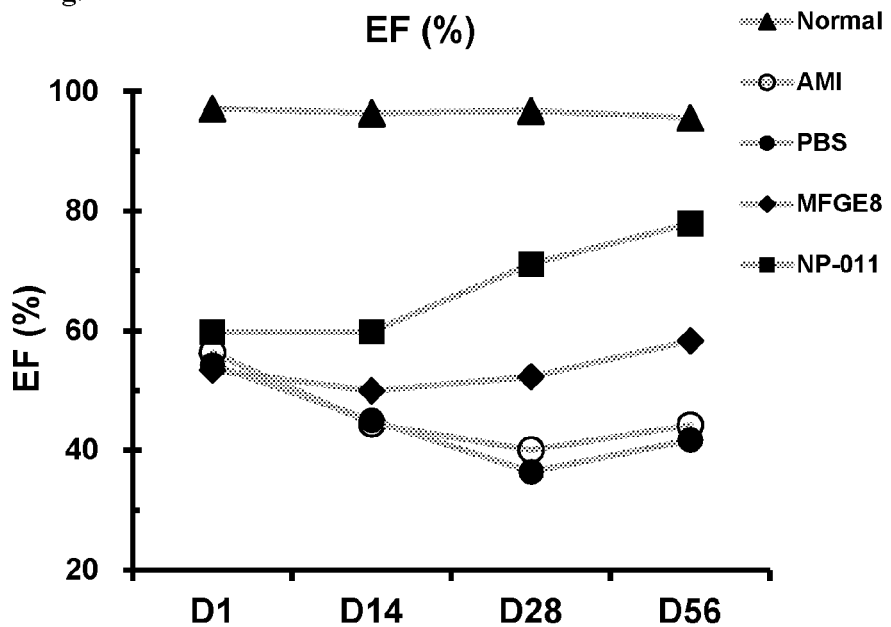
FIG. 24A-FIG. 24B shows that NP-011 reverses symptoms of myocardial infarction, and increases the heart function. Time course analysis of the heart from day 1 to day 56 after LAD ligation is shown. Specifically, functional improvement of heart is assessed by measuring left ventricular ejection fraction (EF.
Figure 24B:
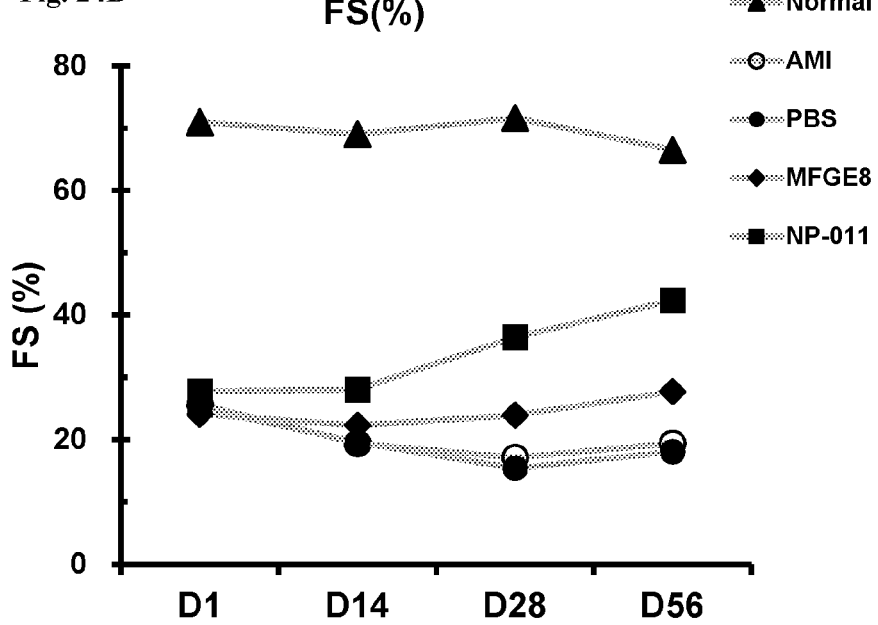

As demonstrated in FIG. 12-FIG. 21, NP-011 is highly efficacious against IPF, and reverses and inhibits IPF in vivo. A model for IPF was induced by injection of bleomycin. Reversal of IPF by NP-011 is evident in histological studies of the lung tissues (FIG. 17 and FIG. 18, as compared to FIG. 13). In addition, NP-011 reverses the bleomycin-induced changes in the expression level of IPF biomarkers such as αSMA, collagen (Col1a1), TMP2, MMP2, MMP12, pERK, tERK, pSMAD2 (phosphorylated SMAD2), and tSMAD2 (total SMAD2) (FIG. 12-FIG. 21). Thus, NP-011 provides a highly effective therapy for treating, inhibiting, preventing, and reversing IPF.

Figure 25:
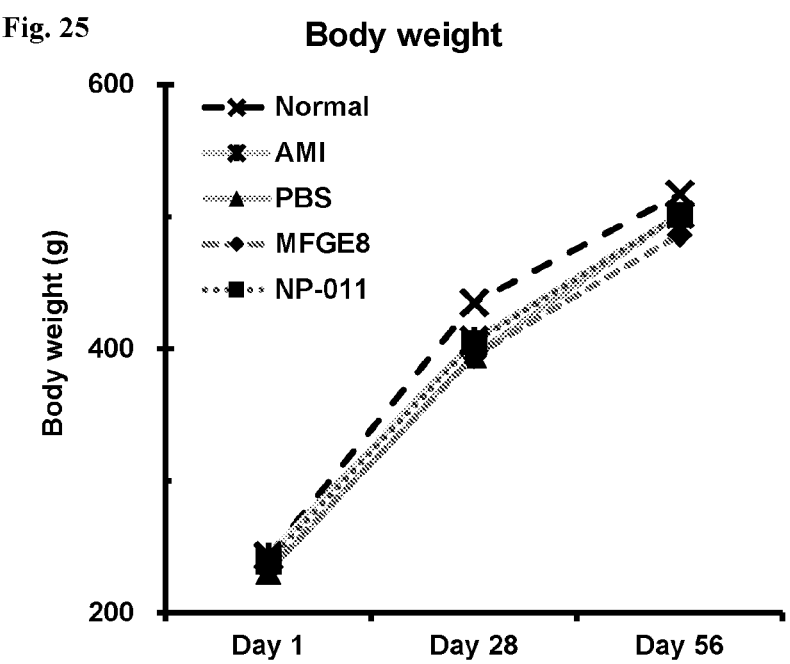
FIG. 25 shows a change in body weight after time. No significant change in body weight is observed from day 1 to day 56.
Figure 26A:
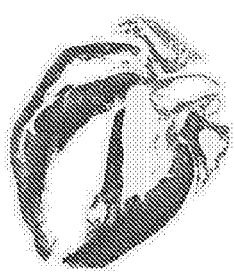
FIG. 26A-FIG. 26B show that NP-011 reverses symptoms of myocardial infarction. NP-011 reverses the fibrosis associated with myocardial infarction.
Figure 26A:
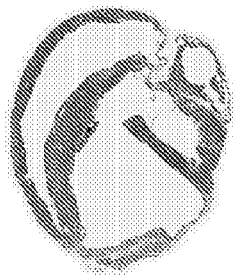
Figure 26A:
Figure 26A:
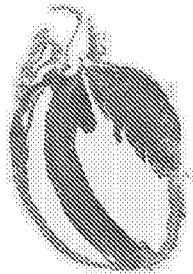
Figure 26A:
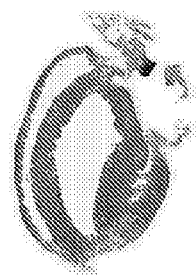
Figure 26B:
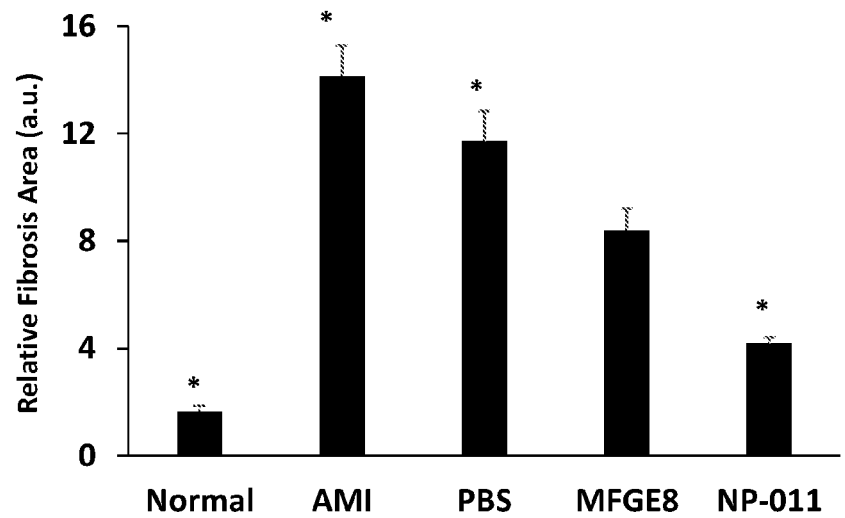
Figure 27A:
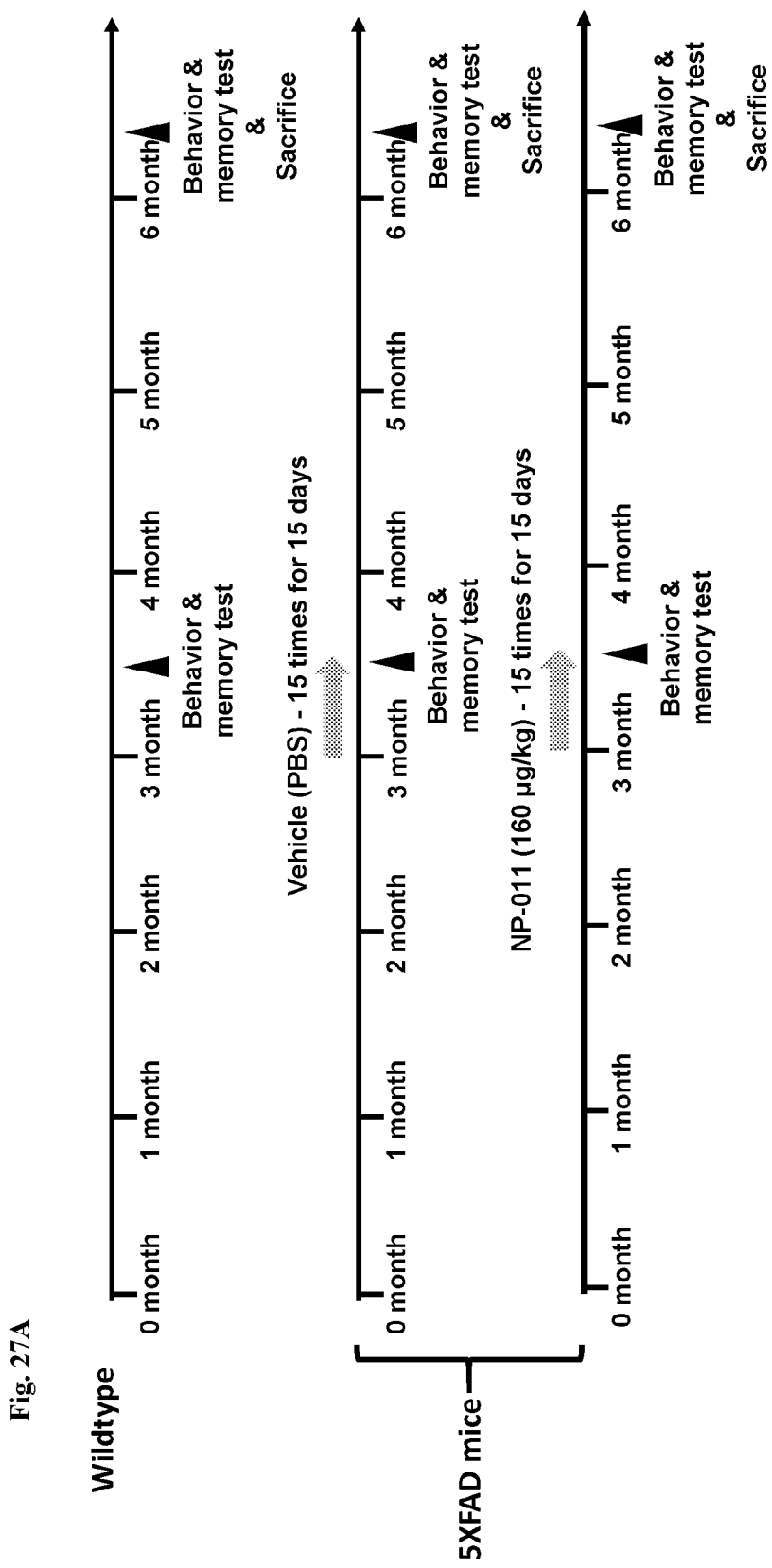
Figure 27B:
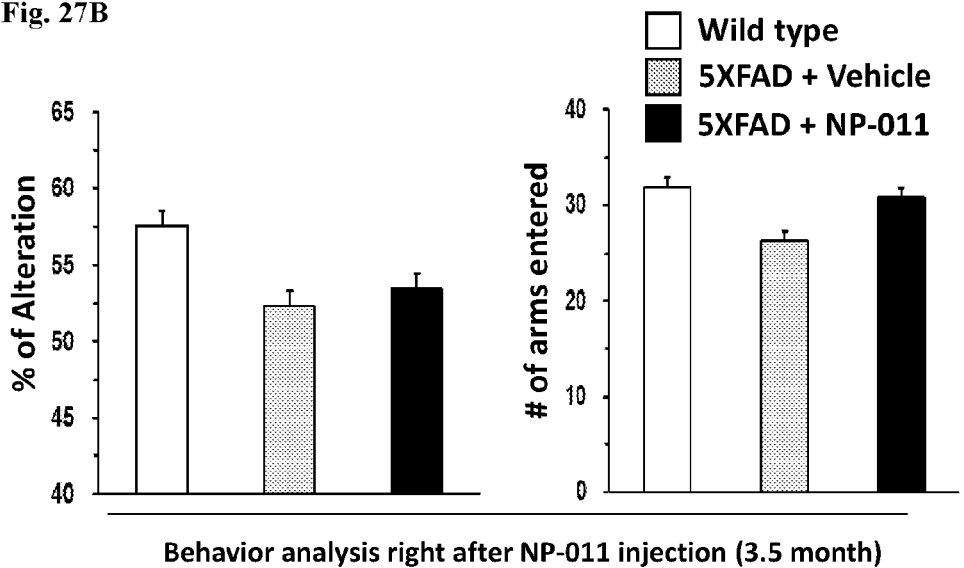
Figure 27C:
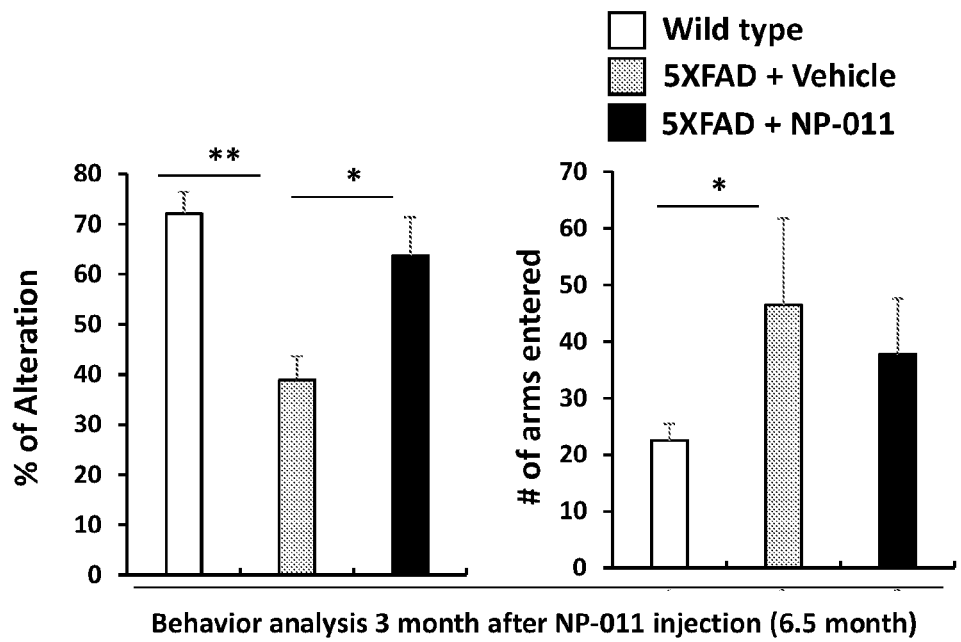
Figure 28A:
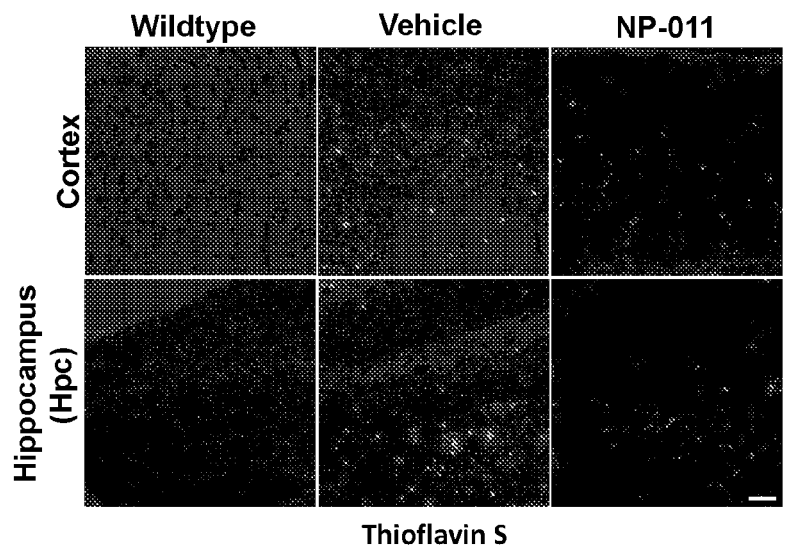
FIG. 28A-FIG. 28B show that NP-011 reverses the neuropathological alterations in the brains of Alzheimer's Disease. Specifically, NP-011 decreases the amount of amyloid plaques in AD.
Figure 28B:
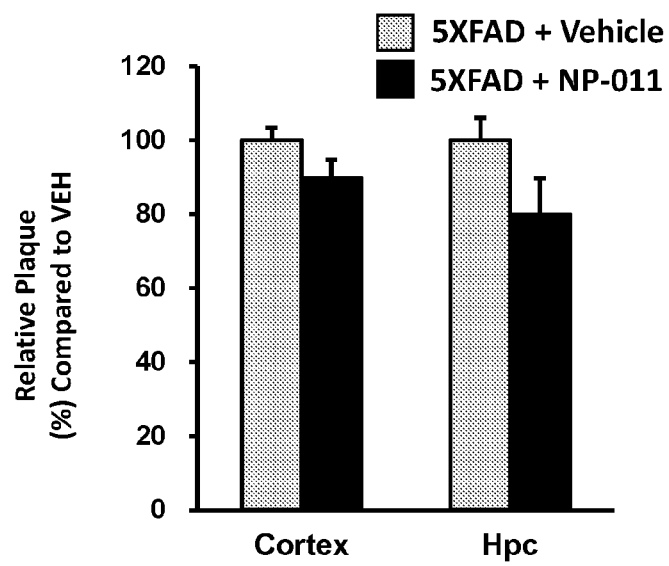
Figure 29A:
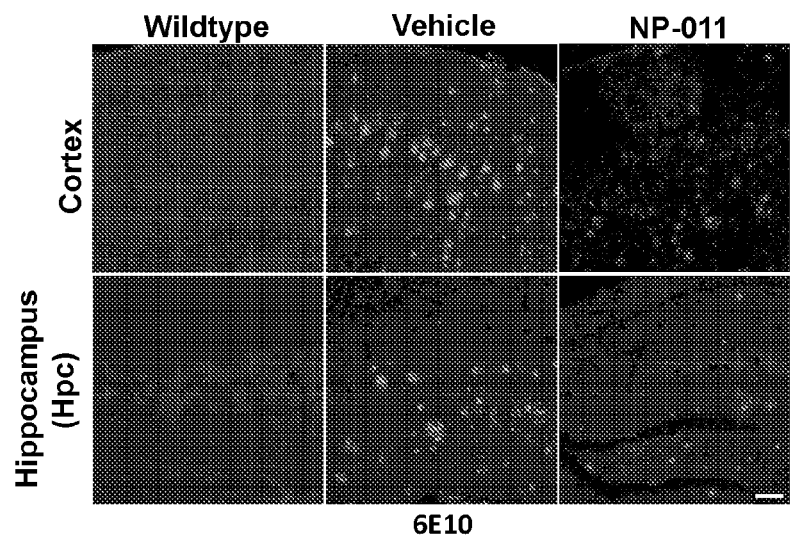
FIG. 29A-FIG. 29B show that NP-011 decreases the amount of amyloid beta in Alzheimer's Disease.
Figure 29B:
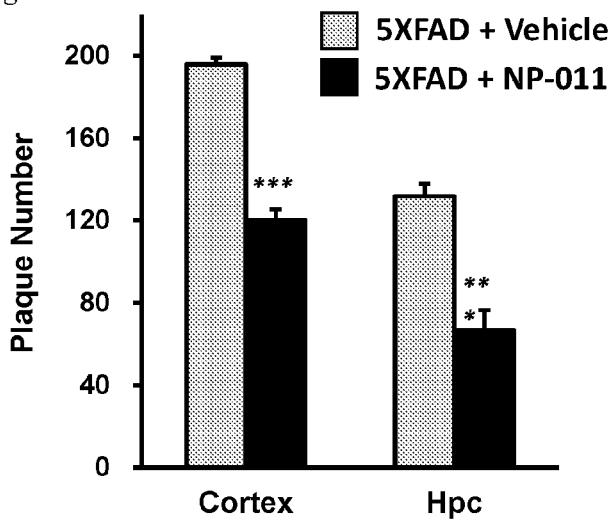
Figure 30A:
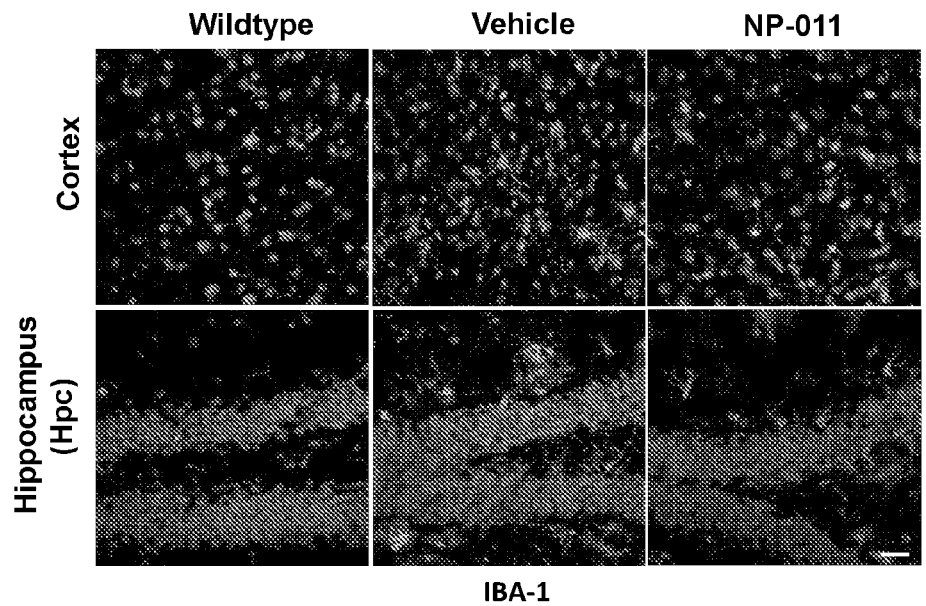
FIG. 30A-FIG. 30B show that NP-011 decreases the number of microglial cells in Alzheimer's Disease.
Figure 30B:
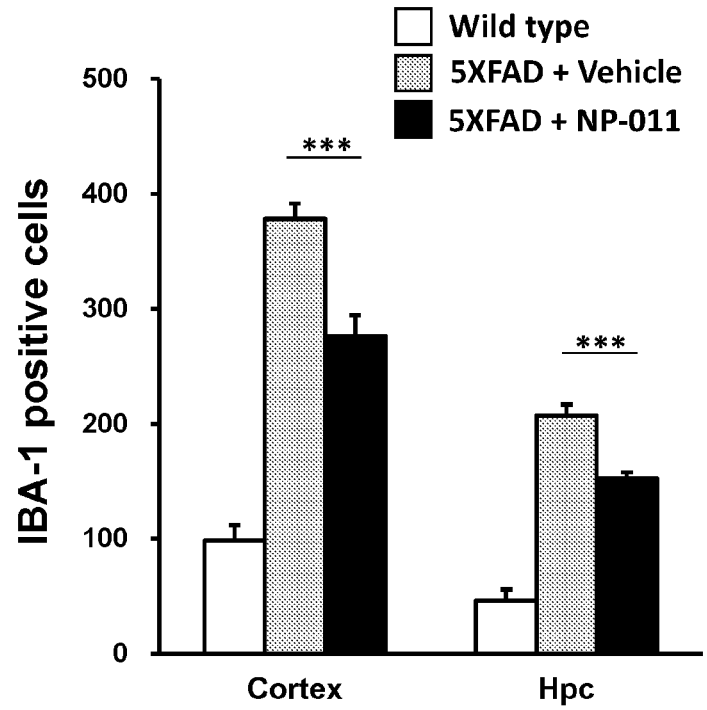
Figure 31A:
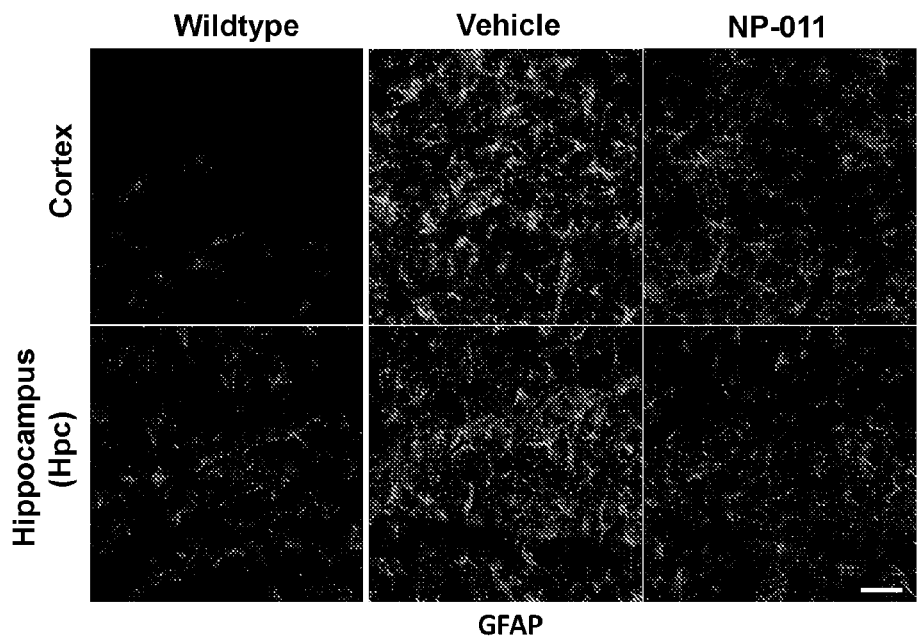
FIG. 31A-FIG. 31B show that NP-011 decreases the amount of glial fibrillary acidic protein (GFAP) that is upregulated in astrocytes of Alzheimer's Disease.
Figure 31B:
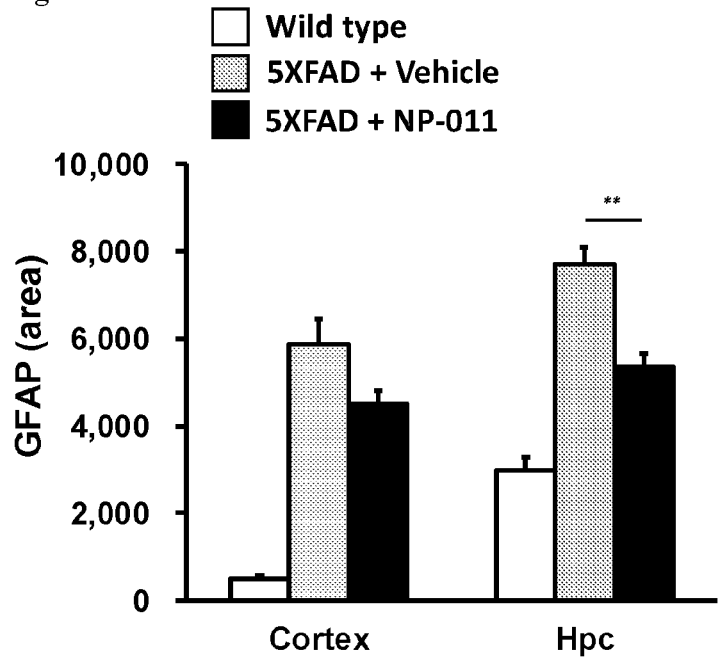

Example 8: NP-011 Reverses, Inhibits, and Prevents Symptoms of Myocardial Infarction and Improves Heart Function As demonstrated in FIG. 22-FIG. 26, NP-011 is highly efficacious against myocardial infarction in vivo. A rat model for myocardial infarction was induced by LAD ligation. Injection of NP-011 increases the heart function as evidenced by increased left ventricular ejection fraction (EF) and fraction shortening (FS) in rats suffering from myocardial infarction (FIG. 23A-24B). Similar body weight for rats injected with NP-011 compared with control rats demonstrate the safety of NP-011 (FIG. 25). Histological studies of cross-sectioned hearts demonstrate that NP-011 also reverses and inhibits the fibrosis associated with myocardial infarction (FIG. 26A-FIG. 26B). Thus, NP-011 provides a highly effective therapy for treating, inhibiting, preventing, and reversing myocardial infarction.

Example 9: NP-011 Reverses, Inhibits, and Prevents Alzheimer's Disease

As demonstrated in FIG. 27-FIG. 31, NP-011 is highly efficacious against Alzheimer's Disease in vivo. 5XFAD mice expressing human APP and PSEN1 transgenes with a total of five AD-linked mutations: the Swedish (K670N/M671L), Florida (I716V), and London (V717I) mutations in APP, and the M146L and L286V mutations in PSEN1, were used as a model for Alzheimer's Disease. NP-011 reverses the behaviors and memory loss associated with Alzheimer's Disease (FIG. 27A-FIG. 27E). NP-011 also reverses and inhibits the neuropathological alteration in AD brains. For example, NP-011 specifically decreases the amount of amyloid plaques (FIG. 28A-FIG. 28B) and amyloid beta (FIG. 29A-FIG. 29B). In addition, NP-011 decreases the number of microglial cells, the brain's innate immune system, the presence of which implies neuroinflammation (FIG. 30A-FIG. 30B). Furthermore, NP-011 decreases the amount of glial fibrillary acidic protein (GFAP) that is upregulated in astrocytes of Alzeheimer's Disease (FIG. 31A-FIG. 31B). Accordingly, NP-011 provides a highly effective therapy for treating, inhibiting, preventing, and reversing Alzheimer's Disease.

REFERENCES

1. Bataller R, Brenner D A. Liver fibrosis. J Clin Invest 2005; 115:209-218.
2. Chung W, Jo C, Chung W J, Kim D J. Liver cirrhosis and cancer: comparison of mortality. Hepatol Int 2018; 12:269-276.
3. Wynn T A, Ramalingam T R. Mechanisms of fibrosis: therapeutic translation for fibrotic disease. Nat Med 2012; 18:1028-1040.
4. Dooley S, ten Dijke P. TGF-β in progression of liver disease. Cell Tissue Res 2012; 347:245-256.
5. Gabbiani G. The myofibroblast in wound healing and fibrocontractive diseases. J Pathol 2003; 200:500-503.
6. Kalluri R, Zeisberg M. Fibroblasts in cancer. Nat Rev Cancer 2006; 6:392-401.
7. Troeger J S, Mederacke I, Gwak G Y, Dapito D H, Mu X, Hsu C C, Pradere J P, Friedman R A, Schwabe R F. Deactivation of hepatic stellate cells during liver fibrosis resolution in mice. Gastroenterology 2012; 143:1073-1083.
8. Uchiyama A, Yamada K, Ogino S, Yokoyama Y, Takeuchi Y, Udey M C, Ishikawa O, Motegi S. MFG-E8 regulates angiogenesis in cutaneous wound healing. Am J Pathol 2014; 184:1981-1990.
9. Yoshida H, Kawane K, Koike M, Mori Y, Uchiyama Y, Nagata S. Phosphatidylserine-dependent engulfment by macrophages of nuclei from erythroid precursor cells. Nature 2005; 437:754-758.
10. Hanayama R, Tanaka M, Miwa K, Shinohara A, Iwamatsu A, Nagata S. Identification of a factor that links apoptotic cells to phagocytes. Nature 2002; 417:182-187.
11. Yi Y S. Functional Role of Milk Fat Globule-Epidermal Growth Factor VIII in Macrophage-Mediated Inflammatory Responses and Inflammatory/Autoimmune Diseases. Mediators Inflamm 2016; 2016:5628486.
12. An S Y, Jang Y J, Lim H J, Han J, Lee J, Lee G, Park J Y, Park S Y, Kim J H, Do B R, Han C, Park H K, Kim O H, Song M J, Kim S J, Kim J H. Milk Fat Globule-EGF Factor 8, Secreted by Mesenchymal Stem Cells, Protects Against Liver Fibrosis in Mice. Gastroenterology 2017; 152:1174-1186.
13. Atabai K, Jame S, Azhar N, Kuo A, Lam M, McKleroy W, Dehart G, Rahman S, Xia D D, Melton A C, Wolters P, Emson C L, Turner S M, Werb Z, Sheppard D. Mfge8 diminishes the severity of tissue fibrosis in mice by binding and targeting collagen for uptake by macrophages. J Clin Invest 2009; 119:3713-3722.
14. Ye H, Li B, Subramanian V, Choi B H, Liang Y, Harikishore A, Chakraborty G, Baek K, Yoon H S. NMR solution structure of C2 domain of MFG-E8 and insights into its molecular recognition with phosphatidylserine. Biochim Biophys Acta 2013; 1828:1083-1093.
15. Köhler C, Bell A W, Bowen W C, Monga S P, Fleig W, Michalopoulos G K. Expression of Notch-1 and its ligand Jagged-1 in rat liver during liver regeneration. Hepatology 2004; 39:1056-1065.
16. Ahmad R, Ahmed S, Khan N U, Hasnain A U. *Operculina turpethum* attenuates N-nitrosodimethylamine induced toxic liver injury and clastogenicity in rats. Chem Biol Interact 2009; 181:145-153.
17. Sarrazy V, Koehler A, Chow M L, Zimina E, Li C X, Kato H, Caldarone C A, Hinz B. Integrins αvβ5 and αvβ3 promote latent TGF-β1 activation by human cardiac fibroblast contraction. Cardiovasc Res 2014; 102:407-417.
18. Théret N, Musso O, L'Helgoualc'h A, Clément B. Activation of matrix metalloproteinase-2 from hepatic stellate cells requires interactions with hepatocytes. *Am J Pathol* 1997; 150:51-58.
19. Iredale J P, Benyon R C, Arthur M J, Ferris W F, Alcolado R, Winwood P J, Clark N, Murphy G. Tissue inhibitor of metalloproteinase-1 messenger RNA expression is enhanced relative to interstitial collagenase messenger RNA in experimental liver injury and fibrosis. Hepatology 1996; 24:176-184.
20. Liu B, Shi D, Chang S, Gong X, Yu Y, Sun Z, Wu J. Characterization and immunological activity of different forms of recombinant secreted Hc of botulinum neurotoxin serotype B products expressed in yeast. Sci Rep 2015; 5:7678.
21. Westermark P, Johnson K H, O'Brien T D, Betsholtz C. Islet amyloid polypeptide—a novel controversy in diabetes research. Diabetologia 1992; 35:297-303.
22. Westermark P, Mucchiano G, Marthin T, Johnson K H, Sletten K. Apolipoprotein A1-derived amyloid in human aortic atherosclerotic plaques. Am J Pathol 1995; 147:1186-1192.
23. Häggqvist B, Näslund J, Sletten K, Westermark G T, Mucchiano G, Tjernberg L O, Nordstedt C, Engström U, Westermark P. Medin: an integral fragment of aortic smooth muscle cell-produced lactadherin forms the most common human amyloid. Proc Natl Acad Sci USA 1999; 96:8669-8674.
24. Ong J P, Younossi Z M. Epidemiology and natural history of NAFLD and NASH. Clin Liver Dis 2007; 11:1-16, vii.
25. Assy N, Kaita K, Mymin D, Levy C, Rosser B, Minuk G. Fatty infiltration of liver in hyperlipidemic patients. Dig Dis Sci 2000; 45:1929-1934.
26. Dorison A, Dussaule J C, Chatziantoniou C. The Role of Discoidin Domain Receptor 1 in Inflammation, Fibrosis and Renal Disease. Nephron 2017; 137:212-220.
27. Borza C M, Pozzi A. Discoidin domain receptors in disease. Matrix Biol 2014; 34:185-192.
28. Anstee Q M, Targher G, Day C P. Progression of NAFLD to diabetes mellitus, cardiovascular disease or cirrhosis. Nat Rev Gastroenterol Hepatol 2013; 10:330-344.
29. Solá R J, Griebenow K. Effects of glycosylation on the stability of protein pharmaceuticals. J Pharm Sci 2009; 98:1223-1245.

What is claimed is:

1. A pharmaceutical composition comprising a recombinant polypeptide that (a) lacks a medin polypeptide of MFG-E8, and (b) comprises an MFG-E8 polypeptide that has at least 90% sequence identity to:
   (i) the amino acid residues 1-225 of SEQ ID NO: 10 or SEQ ID NO: 12; or
   (ii) the amino acid residues 24-225 of SEQ ID NO: 10 or SEQ ID NO: 12,
   wherein the MFG-E8 polypeptide is not glycosylated.

2. The pharmaceutical composition of claim 1, wherein
   (a) the recombinant polypeptide lacks at least 55, 60, 65, 70, 75, 80, 85, 90, 95, 100, or 105 amino acids within the C-terminal domain comprising amino acid residues 226-335 of SEQ ID NO: 10 or SEQ ID NO: 12; and/or
   (b) the recombinant polypeptide comprises at least 210, 215, 220, 225, 230, 235, 240, 245, 250, 255, 260, 265, 270, 275, or 280 amino acid residues of SEQ ID NO: 10 or SEQ ID NO: 12.

3. The pharmaceutical composition of claim 1,
   (a) wherein the recombinant polypeptide further comprises a heterologous sequence;
   (b) wherein the recombinant polypeptide further comprises polyethylene glycol (PEG), lipid, or PEG-modified lipid; and/or
   (c) wherein the recombinant polypeptide is not glycosylated.

4. The pharmaceutical composition of claim 1, wherein the recombinant polypeptide is capable of:
   (a) decreasing the expression level of TGF-β 1;
   (b) decreasing TGF-β signaling;
   (c) decreasing phosphorylation of SMAD2, and/or ERK;
   (d) decreasing fibrosis-related gene expression, optionally wherein the fibrosis-related genes comprise Col1a1, Col1a2, and/or Acta2;
   (e) decreasing interaction between TGF-β receptor 1 (TGFBR1) and one or more integrins, optionally wherein the integrins comprise integrin β3 and/or integrin β5;

(f) decreasing proliferation of hepatic stellate cells (HSC);
(g) decreasing the expression level of matrix metallopeptidase 2 (MMP2), matrix metallopeptidase 12 (MMP12), TMP2, ERK, SMAD2;
(h) increasing collagenase activity; and/or
(i) increasing collagen or apoptotic cell uptake by macrophages.

5. The pharmaceutical composition of claim 1, further comprising one or more pharmaceutically acceptable carriers and/or diluents.

6. A method of increasing the activity of a macrophage, the method comprising contacting a macrophage with the pharmaceutical composition of claim 1, optionally wherein the activity comprises uptake of collagens, apoptotic cells, or fibrotic tissues.

7. A method of decreasing or inhibiting proliferation of hepatic stellate cells (HSC), the method comprising contacting the HSC with the pharmaceutical composition of claim 1.

8. A method of decreasing or inhibiting fibrosis or steatosis in a subject, the method comprising contacting a cell of the subject with the pharmaceutical composition of claim 1.

9. A method of treating or preventing a disorder in a subject in need thereof, the method comprising administering to the subject the pharmaceutical composition of claim 1.

10. The method of claim 9, wherein the disorder is
(a) chronic or acute fibrosis (chronic or acute), cirrhosis, steatosis, nonalcoholic steatohepatitis (NASH), and/or lung fibrosis;
(b) idiopathic pulmonary fibrosis (IPF), optionally where the polypeptide alters the expression level of IPF biomarkers, optionally where the polypeptide decreases the expression level of at least one biomarker selected from αSMA, collagen (Col1a1), TMP2, MMP2, MMP12, phosphorylated ERK, ERK, phosphorylated SMAD2, and SMAD2;
(c) myocardial infarction; or
(d) Alzheimer's Disease.

11. The method of claim 10, wherein the disorder is myocardial infarction, and
(a) the pharmaceutical composition increases the function of a heart, optionally wherein the recombinant polypeptide increases left ventricular ejection fraction and/or fraction shortening; and/or
(b) the pharmaceutical composition inhibits or decreases the fibrosis associated with myocardial infarction.

12. The method of claim 10, wherein the disorder is Alzheimer's Disease, and
(a) the subject has (i) at least one mutation in amyloid precursor protein (APP) selected from K670N/M671L, I716V, and V717I; and/or (ii) at least one mutation in PSEN1 selected from M146L and L286V;
(b) the pharmaceutical composition improves memory loss and/or behaviors associated with Alzheimer's disease; and/or
(c) the pharmaceutical composition decreases:
(i) the amount of amyloid plaques;
(ii) the amount of amyloid beta;
(iii) the number of microglia;
(iv) neuroinflammation; and/or
(v) the amount of glial fibrillary acidic protein (GFAP) in the brain of the subject, optionally in hippocampus and/or cortex of the brain of the subject.

13. The method of claim 8,
(a) wherein the pharmaceutical composition is administered via an intravenous, subcutaneous, intra-arterial, intraperitoneal, or intramuscular route;
(b) wherein the subject is a mammal, optionally wherein the mammal is a human, a mouse, or a rat;
(c) further comprising administering to the subject an additional agent that treats the disorder; and/or
(d) wherein the method does not induce amyloid formation in the subject.

14. The method of claim 9,
(a) wherein the pharmaceutical composition is administered via an intravenous, subcutaneous, intra-arterial, intraperitoneal, or intramuscular route;
(b) wherein the subject is a mammal, optionally wherein the mammal is a human, a mouse, or a rat;
(c) further comprising administering to the subject an additional agent that treats the disorder; and/or
(d) wherein the method does not induce amyloid formation in the subject.

15. A kit comprising the pharmaceutical composition of claim 1.

16. The pharmaceutical composition of claim 1, wherein the recombinant polypeptide lacks the amino acid residues 226-387 of SEQ ID NO: 10 or SEQ ID NO: 12.

17. The pharmaceutical composition of claim 1, wherein the recombinant polypeptide
(a) lacks the amino acid residues 226-387 of SEQ ID NO: 10 or SEQ ID NO: 12; and
(b) comprises:
(i) the amino acid residues 1-225 of SEQ ID NO: 10 or SEQ ID NO: 12; or
(ii) the amino acid residues 24-225 of SEQ ID NO: 10 or SEQ ID NO: 12.

18. The pharmaceutical composition of claim 3, wherein the heterologous sequence comprises a FLAG tag, a HIS tag, and/or GST.

19. The pharmaceutical composition of claim 3, wherein the heterologous sequence increases the half life of the polypeptide in vivo.

20. The pharmaceutical composition of claim 19, wherein the heterologous sequence comprises an Fc portion of an immunoglobulin.

21. The pharmaceutical composition of claim 1, wherein the pharmaceutical composition is suitable for parenteral administration.

* * * * *

UNITED STATES PATENT AND TRADEMARK OFFICE
CERTIFICATE OF CORRECTION

PATENT NO. : 12,139,518 B2
APPLICATION NO. : 17/285040
DATED : November 12, 2024
INVENTOR(S) : Choongseong Han et al.

Page 1 of 1

It is certified that error appears in the above-identified patent and that said Letters Patent is hereby corrected as shown below:

In the Claims

In subsection of (a) in Claim 10, at Column 107, Line 29, replace --chronic or acute fibrosis (chronic or acute), cirrhosis-- with "chronic or acute fibrosis, cirrhosis".

Signed and Sealed this
Sixteenth Day of September, 2025

Coke Morgan Stewart
*Acting Director of the United States Patent and Trademark Office*